United States Patent
van Walsum et al.

(10) Patent No.: US 11,707,242 B2
(45) Date of Patent: Jul. 25, 2023

(54) METHODS AND SYSTEMS FOR DYNAMIC CORONARY ROADMAPPING

(71) Applicant: Pie Medical Imaging B.V., Maastricht (NL)

(72) Inventors: Theo van Walsum, Houten (NL); Hua Ma, Rotterdam (NL); Jean-Paul Aben, Limbricht (NL); Dennis Koehn, Voerendaal (NL)

(73) Assignee: Pie Medical Imaging B.V., Maastricht (NL)

( * ) Notice: Subject to any disclaimer, the term of this patent is extended or adjusted under 35 U.S.C. 154(b) by 588 days.

(21) Appl. No.: 16/739,718

(22) Filed: Jan. 10, 2020

(65) Prior Publication Data

US 2020/0222018 A1    Jul. 16, 2020

Related U.S. Application Data

(60) Provisional application No. 62/791,286, filed on Jan. 11, 2019.

(51) Int. Cl.
*A61B 6/00* (2006.01)
*G06T 7/73* (2017.01)
(Continued)

(52) U.S. Cl.
CPC .......... *A61B 6/5205* (2013.01); *A61B 5/0044* (2013.01); *A61B 5/349* (2021.01);
(Continued)

(58) Field of Classification Search
CPC ..... A61B 6/5205; A61B 5/0044; A61B 5/349; A61B 6/032; A61B 6/461; A61B 6/481;
(Continued)

(56) References Cited

U.S. PATENT DOCUMENTS

| 4,878,115 A | 10/1989 | Elion |
|---|---|---|
| 9,256,936 B2 | 2/2016 | Jacobs et al. |

(Continued)

FOREIGN PATENT DOCUMENTS

| EP | 0193712 A1 | 9/1986 |
|---|---|---|
| EP | 3206183 A1 | 8/2017 |

OTHER PUBLICATIONS

Chen et al. 2003 IEEE Transactions on Medical Imaging 22 710-721 (Year: 2003).*

(Continued)

*Primary Examiner* — Keith M Raymond
*Assistant Examiner* — Patrick M Mehl
(74) *Attorney, Agent, or Firm* — Gordon & Jacobson, P.C.

(57) ABSTRACT

Methods are provided for dynamically visualizing information in image data of an object of interest of a patient, which include an offline phase and an online phase. In the offline phase, first image data of the object of interest acquired with a contrast agent is obtained with an interventional device is present in the first image data. The first image data is used to generate a plurality of roadmaps of the object of interest. A plurality of reference locations of the device in the first image data is determined, wherein the plurality of reference locations correspond to the plurality of roadmaps. In the online phase, live image data of the object of interest acquired without a contrast agent is obtained with the device present in the live image data, and a roadmap is selected from the plurality of roadmaps. A location of the device in the live image data is determined. The reference location of the device corresponding to the selected roadmap and the location of the device in the live image data is used to transform the selected roadmap to generate a dynamic roadmap of the object of interest. A visual representation of (Continued)

the dynamic roadmap is overlaid on the live image data for display. In embodiments, the first image data of the offline phase covers different of phases of the cardiac cycle of the patient, and the plurality of roadmaps generated in the offline phase covers the different phases of the patient's cardiac cycle. Related systems and program storage devices are also described and claimed.

39 Claims, 39 Drawing Sheets

(51) Int. Cl.
    *A61B 6/03*     (2006.01)
    *G06T 7/00*     (2017.01)
    *A61B 5/00*     (2006.01)
    *A61B 5/349*     (2021.01)
    *G16H 30/20*     (2018.01)
    *G16H 30/40*     (2018.01)

(52) U.S. Cl.
    CPC .............. *A61B 6/032* (2013.01); *A61B 6/461* (2013.01); *A61B 6/481* (2013.01); *A61B 6/503* (2013.01); *A61B 6/504* (2013.01); *A61B 6/5264* (2013.01); *G06T 7/0014* (2013.01); *G06T 7/74* (2017.01); *G16H 30/20* (2018.01); *G16H 30/40* (2018.01); *G06T 2207/20081* (2013.01); *G06T 2207/30048* (2013.01)

(58) Field of Classification Search
    CPC ....... A61B 6/503; A61B 6/504; A61B 6/5264; A61B 6/03; A61B 6/4441; A61B 6/5288; A61B 8/0891; A61B 8/483; A61B 6/12; A61B 6/463; A61B 6/464; A61B 6/5235; A61B 6/5247; A61B 6/485–487; G06T 7/0014; G06T 7/74; G06T 2207/20081; G06T 2207/30048; G06T 7/20; G06T 2207/10121; G06T 2207/20076; G06T 2207/20084; G06T 2207/30021; G06T 2207/30101; G06T 10/82; G16H 30/20; G16H 30/40; G16H 50/20; G16H 50/50
    See application file for complete search history.

(56) References Cited

U.S. PATENT DOCUMENTS

| | | | |
|---|---|---|---|
| 9,576,360 B2 | 2/2017 | Schormans et al. | |
| 10,192,352 B2 | 1/2019 | de Vaan et al. | |
| 10,229,516 B2 | 3/2019 | Aben | |
| 10,699,407 B2 | 6/2020 | Isgum et al. | |
| 10,733,792 B2 | 8/2020 | Aben et al. | |
| 2009/0257554 A1* | 10/2009 | Parks .................... | A61B 6/481 378/62 |
| 2010/0049038 A1* | 2/2010 | Florent ................. | A61B 6/481 382/128 |
| 2011/0110488 A1* | 5/2011 | Lardo .................... | A61B 6/504 378/12 |
| 2015/0087972 A1* | 3/2015 | Dumont ................ | A61B 5/318 600/431 |
| 2018/0263522 A1* | 9/2018 | Ghosh .................. | A61N 1/3704 |

OTHER PUBLICATIONS

Kim 2017 PhD thesis Electrical and Computer Engineering Seoul National University South Korea 125 pages (Year: 2017).*
Piayda etal 2018 Eur J Med Res 23 7 pages (Year: 2018).*
Wang etal 2009 IEEE Conf Computer Vision and Pattern Recognition 691-698 (Year: 2009).*
Wu 2014 PhD Thesis Computing of the University of London 191 pages (Year: 2014).*
Ambrosini et al. 2017 IEEE Trans. Med. Imaging 36:757-768. (Year: 2017).*
"3D/3D registration of coronary CTA and biplane XA reconstructions for improved image guidance", Dibildox et al., Med Phys. Sep. 2014;41(9).
"3D+t/2D+t CTA-XA registration using population-based motion estimates", Baka et al, Demirci, Lee, Radeva, Unal (eds): MICCAISTENT 2012, pp. 64-71.
"A Hidden Markov Model for 3D Catheter Tip Tracking With 2D X-ray Catheterization Sequence and 3D Rotational Angiography", Ambrosini et al., IEEE Trans Med Imaging. Mar. 2017;36(3):757-768.
"A tutorial on particle filters for online nonlinear/non-Gaussian Bayesian tracking", Arulampalam et al., IEEE Transactions on signal processing 2002:50, 174-188.
"Adam: a Method for Stochastic Optimization", Kingsma et al., International Conference on Learning Representations, ICLR 2015.
"Advanced three-dimensional quantitative coronary angiographic assessment of bifurcation lesions: methodology and phantom validation", Girasis et al., EuroIntervention. Apr. 22, 2013;8(12):1451-60.
"Advances in two-dimensional quantitative coronary angiographic assessment of bifurcation lesions: improved small lumen diameter detection and automatic reference vessel diameter derivation", Girasis et al., EuroIntervention Mar. 2012;7(11):1326-35.
"An overview of Medical Image registration Methods", Maintz et al., in symposium of the Belgian hospital physicists association, 1996.
"Automated 3-dimensional quantification of noncalcified and calcified coronary plaque from coronary CT angiography", Dey et al., Cardiovasc Comput Tomogr. 2009;3(6):372-382.
"Automatic online layer separation for vessel enhancement in X-ray angiograms for percutaneous coronary interventions", Ma et al., Med Image Anal. Jul. 2017;39:145-161.
"Automatic segmentation and plaque characterization in atherosclerotic carotid artery MR images", Adame et al., Magnetic Resonance Materials in Physics, Biology and Medicine 2004;16 (5): 227-234.
"Bayesian Maximal Paths for Coronary Artery Segmentation from 3D CT Angiograms", Lesage et al., MICCAI 2009, Part 1, LNCS 5761, pp. 222-229.
"Cascade Attention Machine for Occluded Landmark Detection in 2D X-Ray Angiography", Zang et al., Jan. 2019 IEEE Winter Conference on Applications of Computer Vision (WACV).
"Concurrent Segmentation and Localization for Tracking of Surgical Instruments", Laina et al., 2017 International conference on medical image computing and computer-assisted.
"Deep residual learning for image recognition", He et al., 2016 Proceedings of the IEEE conference on computer vision and pattern recognition, pp. 770- 778.
"Fast prospective detection of contrast inflow in x-ray angiograms with convolutional neural network and recurrent neural network", Ma, et al., International Conference on Medical Image Computing and Computer-Assisted Intervention, Springer (2017) 453-461.
"Fully automatic and real-time catheter segmentation in X-ray fluoroscopy", Ambrosini et al., International Conference on Medical Image Computing and Computer-Assisted Intervention 2017, Springer, pp. 577-585.
"Geometry guided data averaging enables the interpretation of shear stress related plaque development in human coronary arteries", Wentzel et al., Journal of Biomechanics 2005, 1551-1555.
"Kinematic and Deformation Analysis of 4-D Coronary Arterial Trees Reconstructed From Cine Angiograms", Chen et al., IEEE Transactions on medical imaging, vol. 22, No. 6, Jun. 2003 pp. 710-721.
"Landmark-based elastic registration using approximating thin-plate splines", Rohr et al., IEEE Trans Med Imaging. Jun. 2001;20(6):526-34.
"Layer separation for vessel enhancement in interventional X-ray angiograms using morphological filtering and robust PCA", Ma et al., Workshop on Augmented Environments for Computer-Assisted Interventions 2017, Springer, pp. 104 113.

(56) References Cited

OTHER PUBLICATIONS

"Linear algebra and its applications", LAY, 2012, 4th edition, p. 142-143, Addison-Wesley Longman.
"Multiscale Vessel Enhancement Filtering", Frangi et al., Medical Image Computing and ComputerAssisted Intervention—MICCAI 1998 Lecture Notes in Computer Science 1496/1998:130.
"Oriented Gaussian mixture models for nonrigid 2D/3D coronary artery registration", Baka et al., IEEE Trans Med Imaging. May 2014;33(5):1023-34.
"Patient Specific 4D Coronary Models from ECG-gated CTA Data for Intraoperative Dynamic Alignment of CTA with X-ray Images", Metz et al., Med Image Comput Assist Interv. 2009;12(Pt 1 ):369-76.
"PCA-derived respiratory motion surrogates from X-ray angiograms for percutaneous coronary interventions", Ma et al., Int J Comput Assist Radiol Surg. Jun. 2015;10(6):695-705.
"Prospective motion correction of X-ray images for coronary interventions", Schechter et al., IEEE Transactions on Medical Imaging 2005:24, 441-450.
"Registration of angiographic image on real-time fluoroscopic image for imageguided percutaneous coronary intervention", Kim et al., International journal of computer assisted radiology and surgery 2018:13, 203-213.
"Sequential reconstruction of vessel skeletons from X-ray coronary angiographic sequences", Zheng et al., Computerized Medical Imaging and Graphics 34 (2010) 333-345.
"Skeletonization of gray-scale image from incomplete boundaries", Li et al., Proceedings of the International Conference on Image Processing, ICIP 2008, Oct. 12-15.
"Standardized evaluation framework for evaluating coronary artery stenosis detection, stenosis quantification and lumen segmentation algorithms in computed tomography angiography", Kirissli et al., Medical Image Analysis, vol. 17, No. 8, pp. 859-876, 2013.
"Statistical coronary motion models for 2D + t/3D registration of X-ray coronary angiography and CTA", Baka et al., Medical Image Analysis, vol. 17, Issue 6, Aug. 2013, pp. 698-709.
"Two-frame motion estimation based on polynomial expansion", Farneback et al., Scandinavian conference on Image analysis 2003, Springer, pp. 363-370.
"U-net: Convolutional networks for biomedical image segmentation", Ronneberger et al., International Conference on Medical image computing and computer-assisted intervention 2015, Springer, pp. 234-241.
"Vessel extraction in coronary X-ray Angiography", Wang et al., Conf Proc IEEE Eng Med Biol Soc. 2005; 2: 1584-1587.
"Vessel extraction in X-ray angiograms using deep learning", Nasr-Esfahani et al., Conf Proc IEEE Eng Med Biol Soc. Aug. 2016;2016:643-646.
"Vessel Layer Separation in Xray Angiograms with Fully Convolutional Network", Hao et al., Proc. SPIE 10576, Medical Imaging 2018: Image-Guided Procedures, Robotic Interventions, and Modeling.
"Visualization of coronary wall atherosclerosis in asymptomatic subjects and patients with coronary artery disease using magnetic resonance imaging", Gerretsen et al., PLoS One. Sep. 29, 2010;5(9).
"V-net: Fully convolutional neural networks for volumetric medical image segmentation", Milletari et al., 2016 Fourth International Conference on 3D Vision (3DV), IEEE. pp. 565-571.

\* cited by examiner

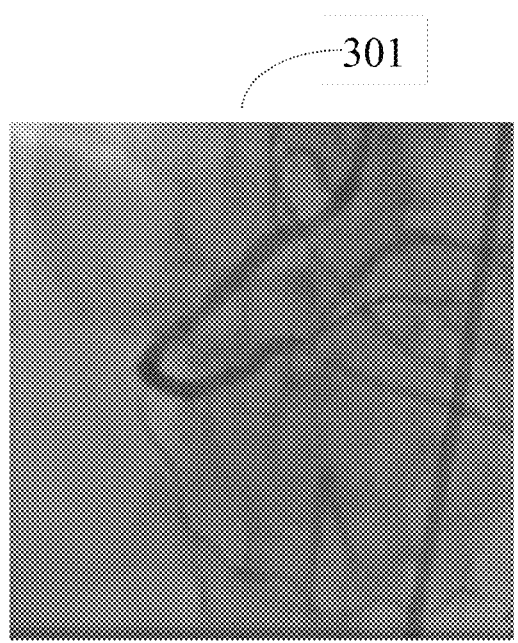 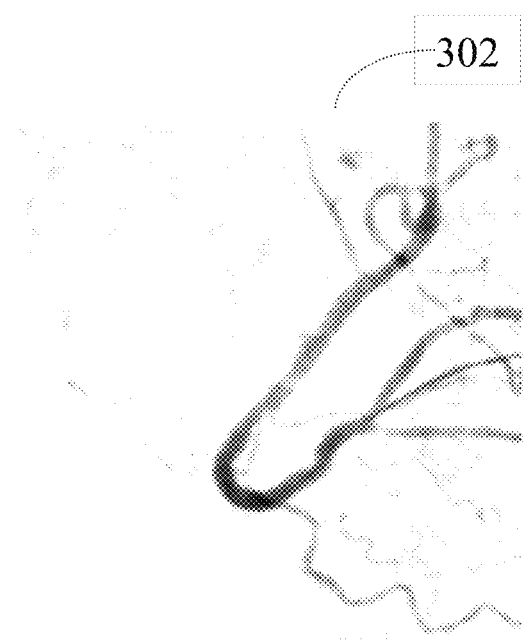 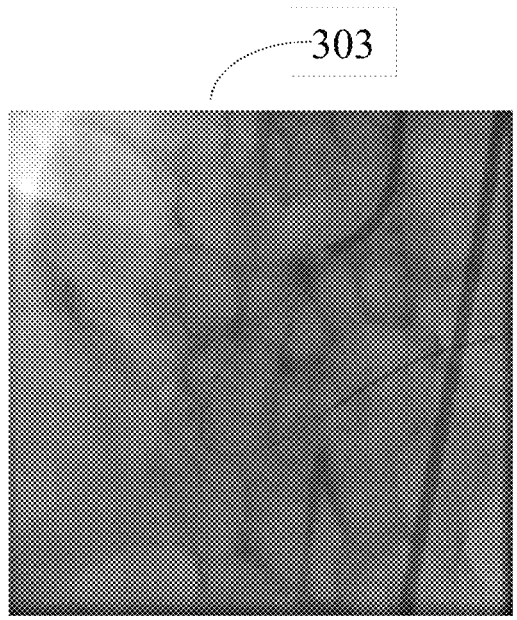 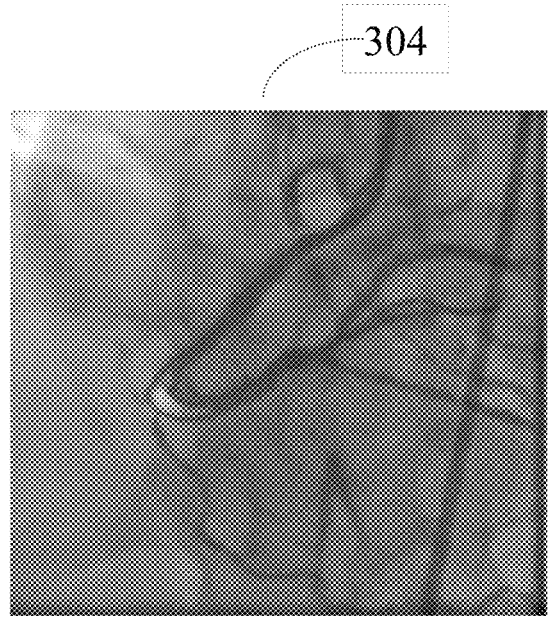
Fig. 3

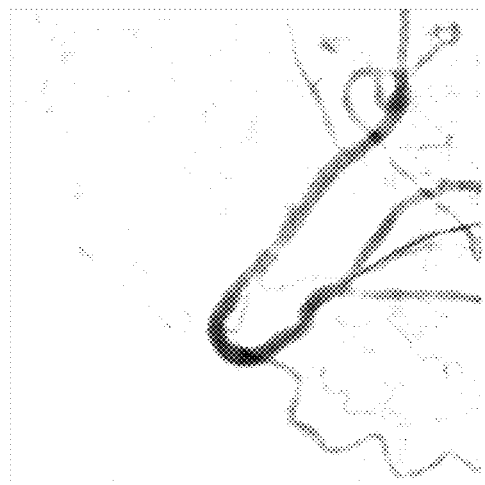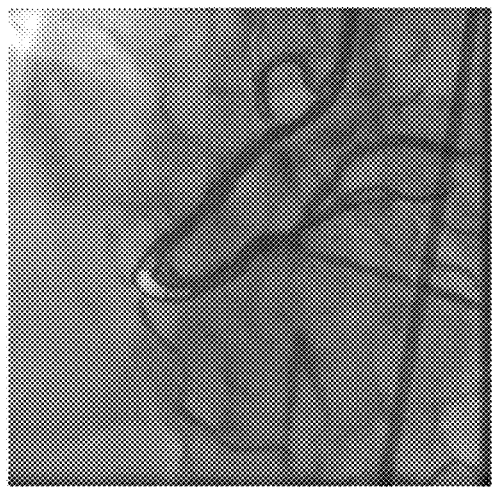
Fig. 10a
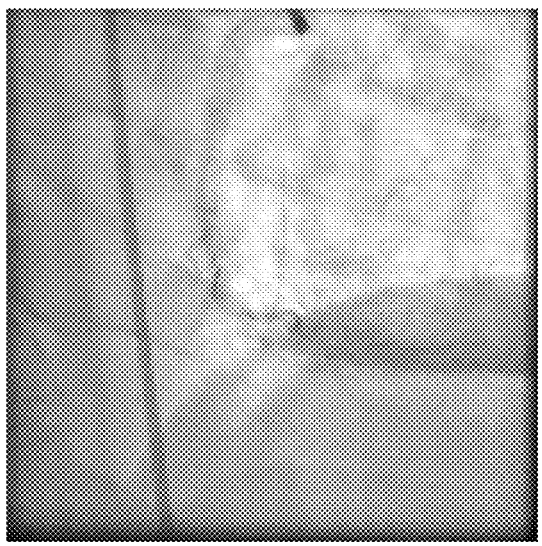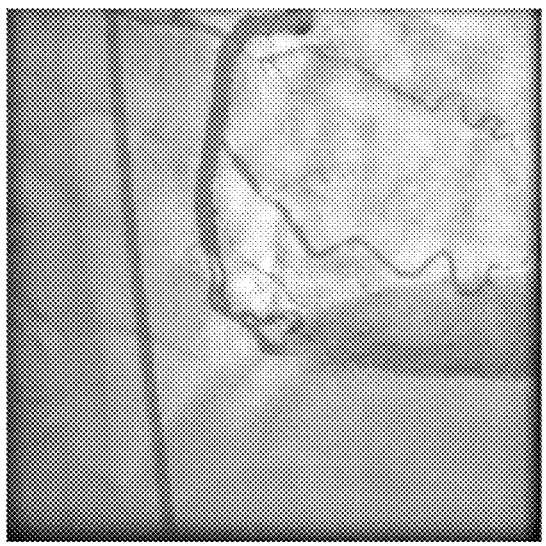
Fig. 10b

Algorithm 1 Deep learning based Bayesian filtering for online tracking of catheter tip in X-ray fluoroscopy

Require: $\{z_0, \ldots, z_T\}$ (sequentially observed frames), $\mathcal{D}$ (A trained network), $p(\mathbf{x}_0)$ (the initial PDF), $\sigma_v^2$ (the variance of $\mathbf{v}_{k-1}$), $k = 1, \ldots, T$), $T$ (number of frames for tracking), $N_s$ (number of samples)

1: Draw $\mathbf{x}_0^i \sim p(\mathbf{x}_0)$, set $w_0^i = 1/N_s$, $\forall i = 1, \ldots, N_s$
2: for $k = 1$ to $T$ do
3:    Compute $\mathbf{u}_{k-1}$ from $\mathbf{z}_{k-1}$ to $\mathbf{z}_k$ using the optical flow method
4:    for $i = 1$ to $N_s$ do
5:       Draw $\mathbf{v}_{k-1}^i \sim \mathcal{N}(\mathbf{0}, \sigma_v^2 I)$
6:       Compute the motion of $\mathbf{x}_{k-1}^i$: $\mathbf{u}_{k-1}^i = \mathbf{u}_{k-1}(\mathbf{x}_{k-1}^i)$
7:       Draw $\mathbf{x}_k^i \sim p(\mathbf{x}_k|\mathbf{x}_{k-1}^i)$: $\mathbf{x}_k^i = \mathbf{x}_{k-1}^i + \mathbf{u}_{k-1}^i + \mathbf{v}_{k-1}^i$
8:       Update weight $w_k^i = p(\mathbf{z}_k|\mathbf{x}_k^i) = \mathcal{D}_{\mathbf{z}_k}(\mathbf{x}_k^i)$
9:    end for
10:   Normalize $w_k^i \leftarrow w_k^i / \sum_{j=1}^{N_s} w_k^j$, $\forall i = 1, \ldots, N_s$
11:   Prediciton in frame $k$: $\hat{\mathbf{x}}_k = \sum_{i=1}^{N_s} w_k^i \mathbf{x}_k^i$
12:   Resample $\{\mathbf{x}_k^i, w_k^i\}_{i=1}^{N_s}$ (so all $w_k^i$ are set to $1/N_s$ again)
13: end for

Fig. 13

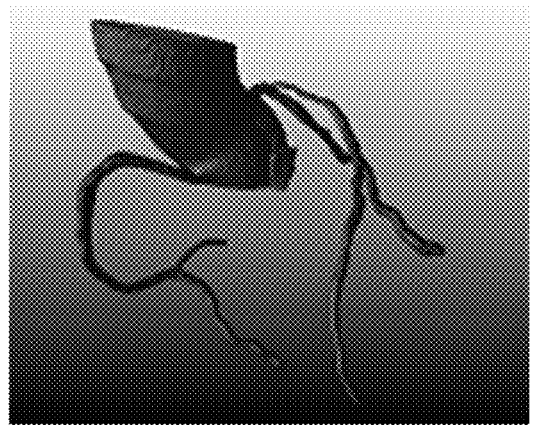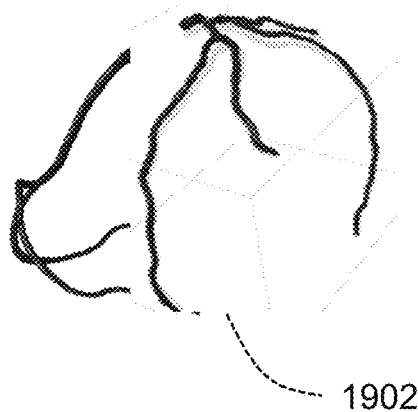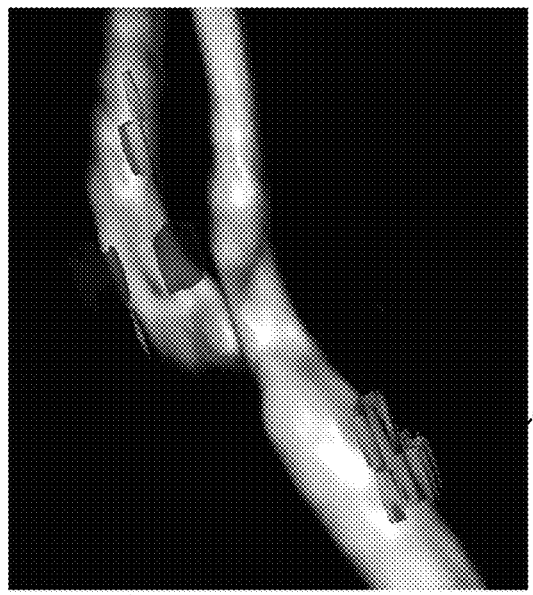
Fig. 19

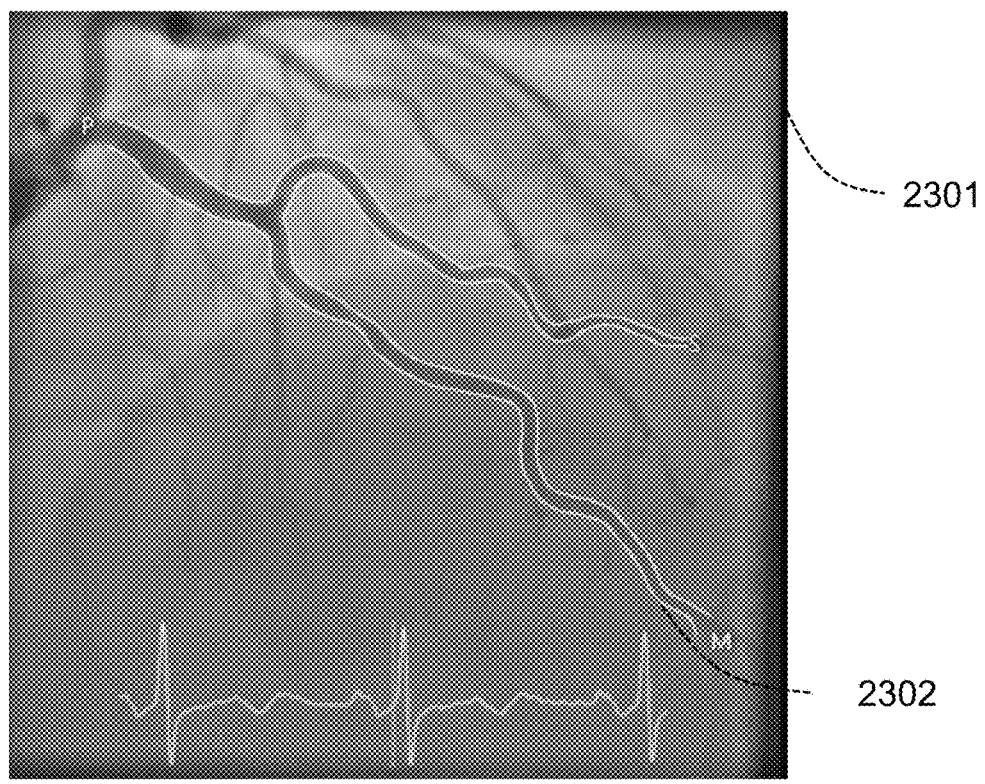
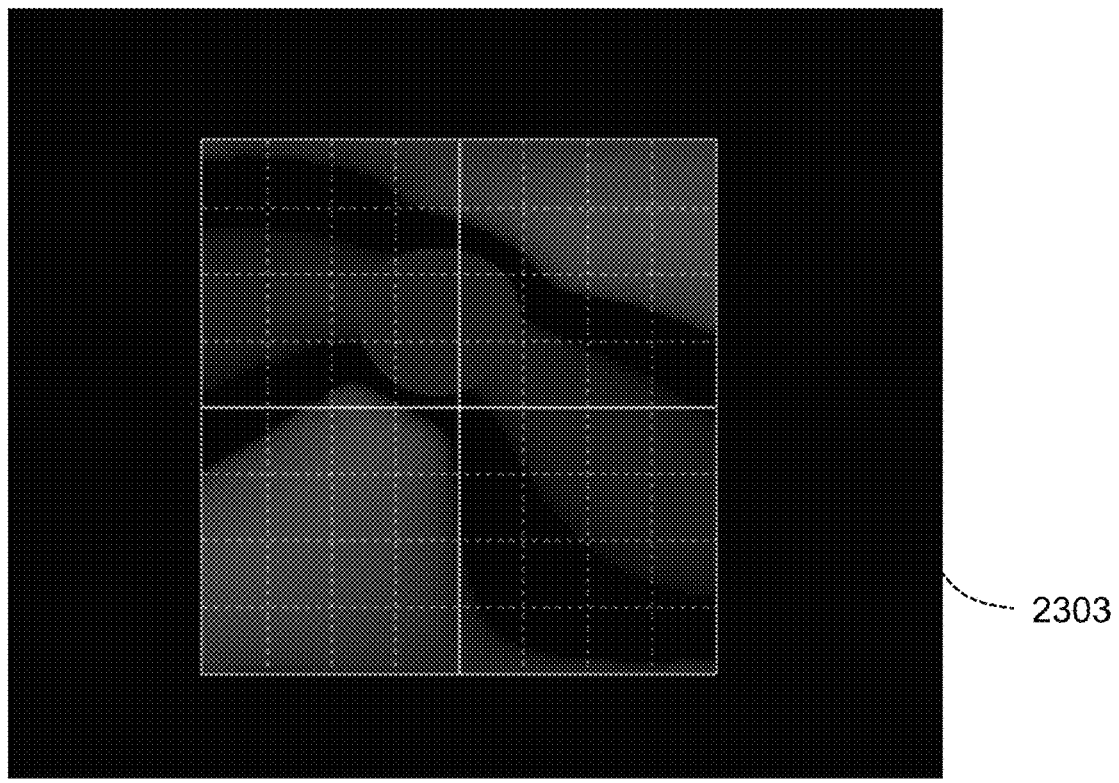
Fig. 23

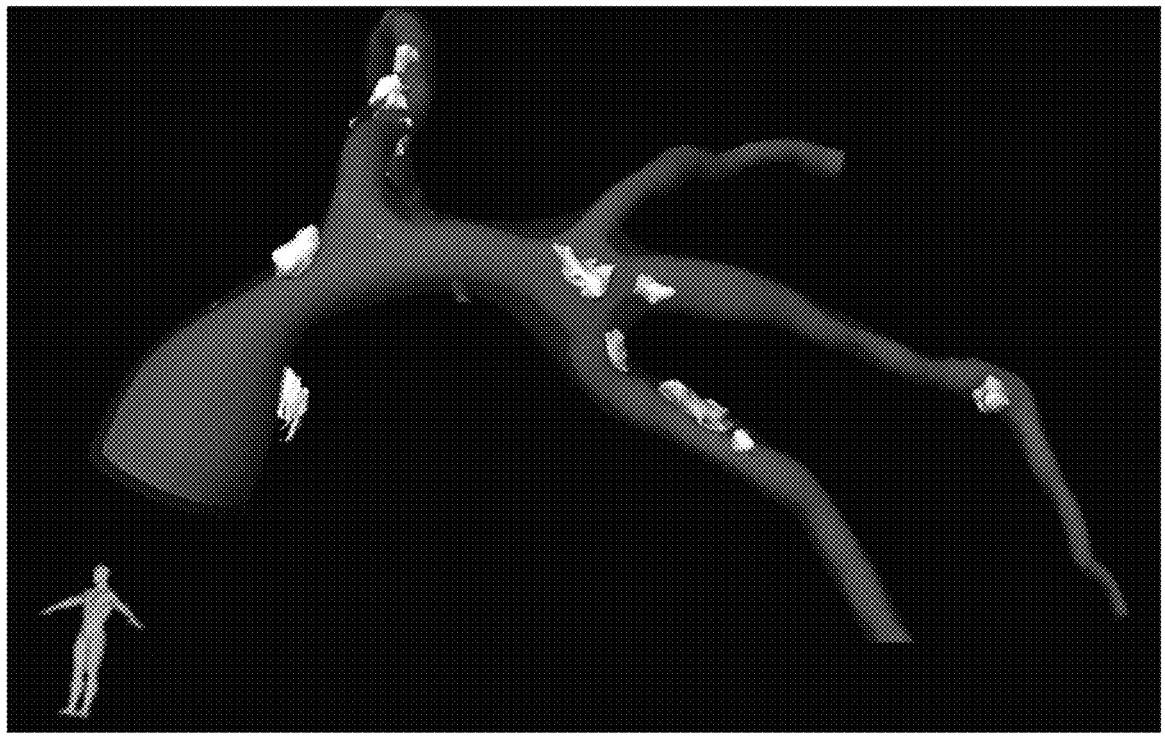
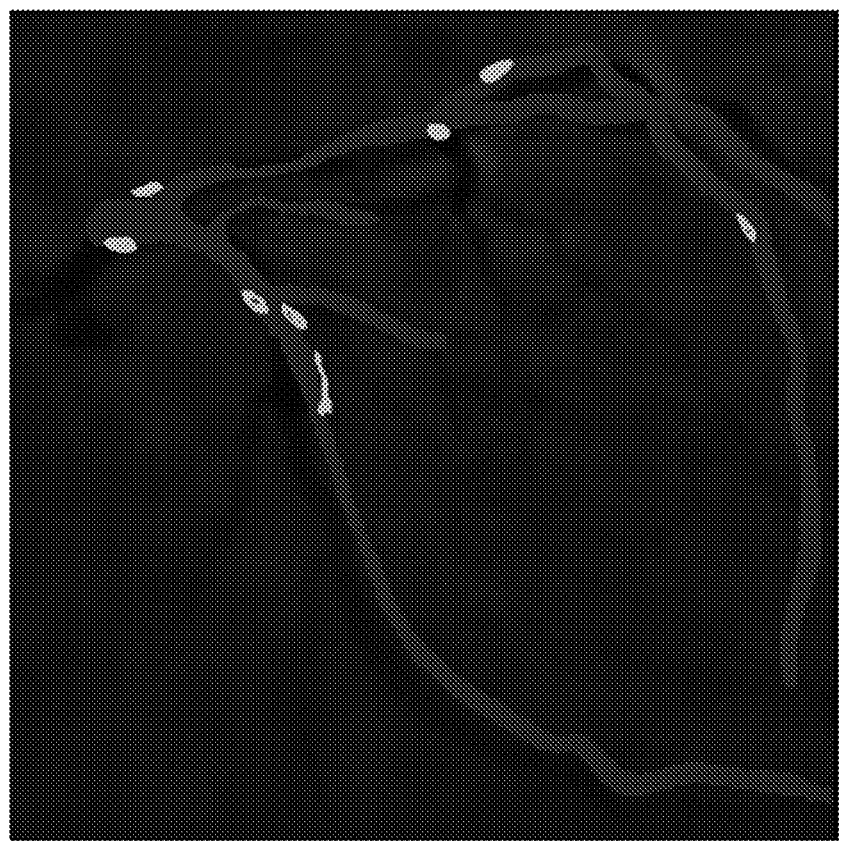
Fig. 25

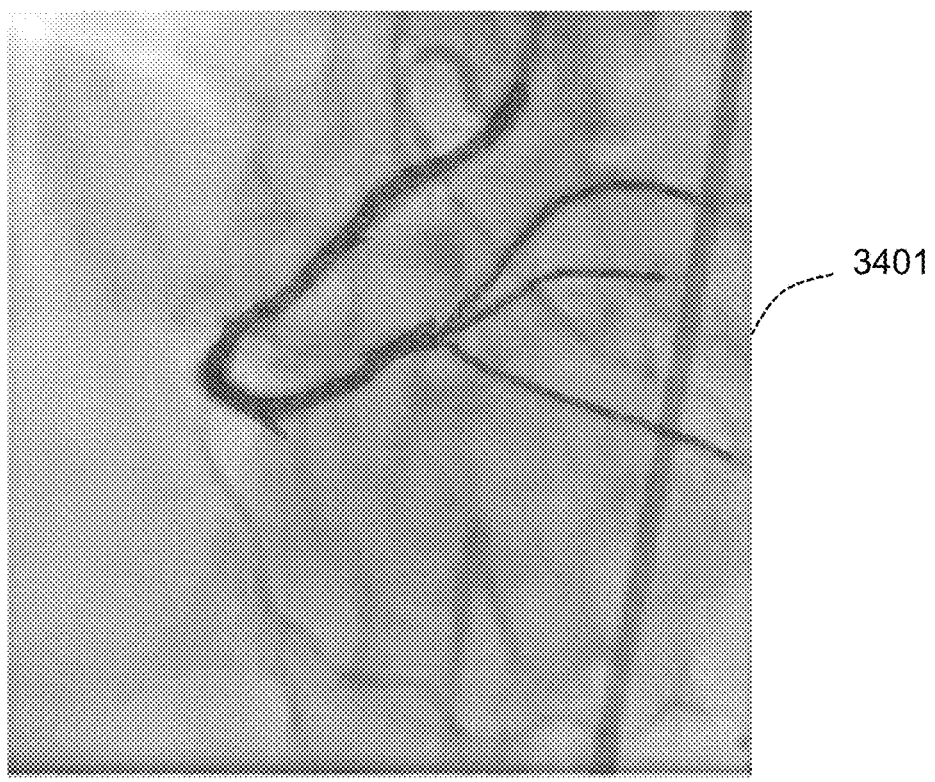
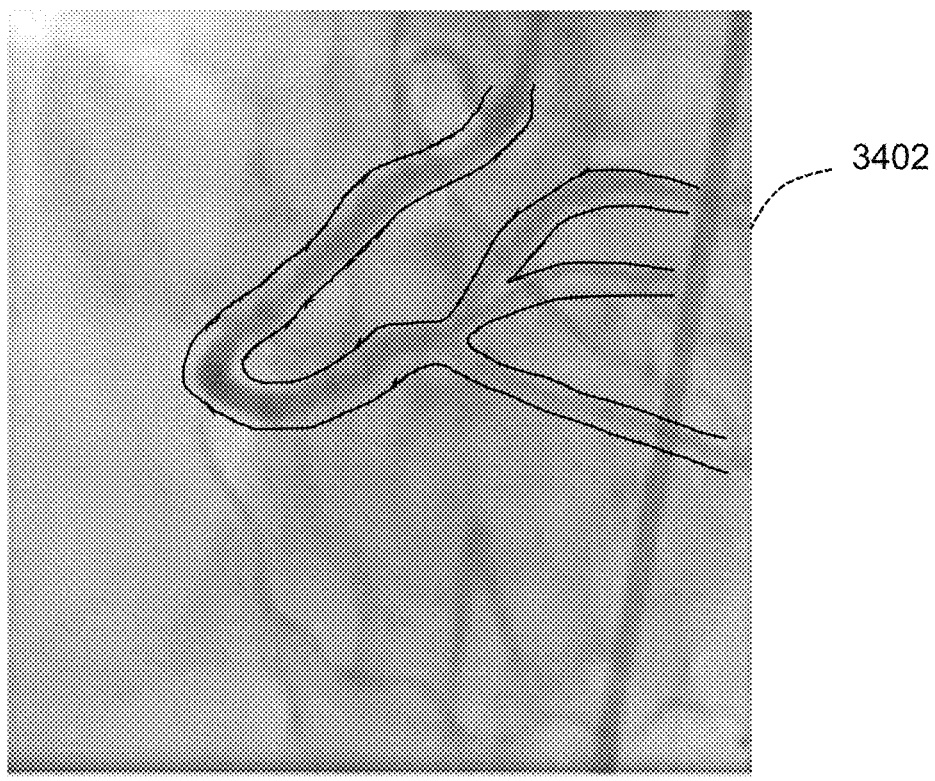
Fig. 34b

METHODS AND SYSTEMS FOR DYNAMIC CORONARY ROADMAPPING

CROSS-REFERENCE TO RELATED APPLICATION(S)

The present disclosure claims priority from U.S. Provisional Patent Appl. No. 62/791,286, filed on Jan. 11, 2019, entitled "METHODS AND SYSTEMS FOR DYNAMIC CORONARY ROADMAPPING," herein incorporated by reference in its entirety.

BACKGROUND

1. Field

The present application relates to the technical field of medical imaging, particularly in percutaneous interventions, although it can find application in any field where there is the need to provide a dynamic roadmap on an image sequence in which the structure of interest is not well visible.

2. State of the Art

The trend of minimal invasiveness has increased the importance of imaging in clinical interventions. Due to the small incisions made for the interventions, clinicians can no longer use direct visual inspect to navigate their tools, and instead have to rely on intra-procedural images generated from real-time imaging modalities such as X-ray angiography and X-ray fluoroscopy, ultrasound echography and intra-procedural magnetic resonance imaging. Presently, X-ray angiography is the main imaging modality used during treatment of cardiovascular diseases by means of a minimally invasive procedure also known as percutaneous coronary intervention (PCI). X-ray angiographic imaging is used to guide the intervention procedure to treat for example atherosclerosis. Atherosclerosis is the build-up of cholesterol and fatty deposits (called plaques) on the inner walls of the arteries. These plaques can restrict blood flow to the heart muscle by physically clogging the artery or by causing abnormal artery tone and function. Without an adequate blood supply, the heart becomes starved of oxygen and the vital nutrients it needs to work properly. This can cause chest pain called angina. If the blood supply to a portion of the heart muscle is cut off entirely, or if the energy demands of the heart become much greater than its blood supply, a heart attack (injury to the heart muscle) may occur or a stroke. Atherosclerosis is treated in arteries of the heart, head, neck and peripheral portions of the body using many different methods. The most popular methods, such as angioplasty, bare metal stenting, drug eluting stenting (permanently implantable and biodegradable), various types of energy delivery and rotational atherectomy, all treat an artery equally around the circumference of a target length of the arterial lumen.

During PCI, a (interventional) cardiologist feeds a deflated balloon or other device on a catheter from the inguinal femoral artery or radial artery up through blood vessels until they reach the site of blockage in the artery. PCI usually involves inflating a balloon to open the artery with the aim to restore unimpeded blood flow. Stents or scaffolds may be placed at the site of the blockage to hold the artery open. During these procedures, medical instruments inserted through a guiding catheter are advanced to treat for instance coronary stenosis. A guiding catheter is firstly positioned into the ostium of the coronary artery. Through the guiding catheter, a balloon catheter carrying a stent is introduced over a guidewire to the stenosis location. PCI is typically performed with image-guidance using X-ray angiography. Coronary arteries are visualized with an X-ray opaque contrast agent. During the procedure, interventional cardiologists may repeatedly inject contrast agent to visualize the vessels, as the opacification of coronary arteries only lasts for a short period. The amount of periprocedural contrast use has been correlated to operator experience, procedural complexity, renal function and imaging setup. Furthermore, the risk for contrast induced nephropathy has been associated to contrast volume. Maneuvering guidewires and material, however, typically occurs without continuous contrast injections. In these situations, the navigation of devices is guided with "vessel-free" fluoroscopic images. Cardiologists have to mentally reconstruct the position of vessels and stenosis based on previous angiograms.

In minimally invasive interventions, such as for example PCI, image guidance and visualization can cause bottlenecks in the feedback loop of physician, instrument and patient. Image guided navigation driven by visual inspection of the intra-procedural images inherently suffers from limited accuracy and operator bias due to the subjective evaluation by the operator. This effect is more prominent when navigating in moving areas, such as the thoracic region. Furthermore, the intra-procedural images generated by the real-time imaging modalities typically have reduced image quality, and may not always reveal anatomical structures relevant for the clinical procedure. Contrast liquid can be used to visualize the anatomical structures. However, intra-procedural administration of contrast liquid, including additional X-ray exposure should be limited to prevent patient harm. For example, it is desirable to reduce the times of X-ray exposure to and the amount of the potentially toxic contrast agent that is injected into a patient's bloodstream. Most of such contrast in used to highlight the aorta and coronaries in fluoroscopic images in order to visually guide physicians. For example, when contrast is injected during a PCI, the coronary tree of the will be visible and when there is no contrast injected, the coronary tree will not be visible. Dynamic coronary roadmapping is a promising solution towards improving visual feedback and reducing usage of contrast medium during PCI. To develop a dynamic coronary roadmapping system, it is important but yet a challenge to accurately overlay a roadmap of coronary arteries onto an X-ray fluoroscopic image, as limited information of vessels is present in the target fluoroscopic image for inferring the compensation of the vessel motion resulting from patient respiration and heartbeat. The methods that have been proposed on motion compensation for dynamic coronary roadmapping can be generally grouped into two categories: direct roadmapping and model-based approaches.

Direct roadmapping methods use information from X-ray images and electrocardiogram signals to directly correct the motion caused by respiration and heartbeat. For instance, U.S. Pat. No. 4,878,115 used digital subtraction of a contrast sequence and a mask sequence to create a full cardiac cycle of coronary roadmaps. The roadmaps are stored and later synchronized with the live fluoroscopic sequence by aligning the R waves of their corresponding electrocardiogram signals. This system compensates the cardiac motion of vessels, yet does not correct the respiratory motion and patient motion during interventions. Furthermore, it requires to be run on cardiac-gated frames. European Patent No. 0,193,712 discloses an X-ray diagnostic device for subtraction angiography. It utilizes a single mask frame and integrates it over a full cycle. By integrating the mask over the full cardiac cycle, the misregistration error is simply distributed and not minimized.

Unlike direct roadmapping, the model-based approach builds a model to predict motion in fluoroscopic frames. The motion model is often one or more functions that relate the motion of roadmaps to surrogate signals derived from images or electrocardiogram, so that once the surrogates for fluoroscopic frames are obtained, the motion can be computed by the motion model. For cardiac interventions including PCI, the organ motion is mainly affected by respiratory and cardiac motion. Previous works built a motion model parameterized by a cardiac signal derived from ECG and a respiratory signal obtained from diaphragm tracking as for instance taught by Shechter et al., *"Prospective motion correction of X-ray images for coronary interventions"*, IEEE Transactions on Medical Imaging 2005:24, 441-450. Limitation of the model-based approaches is that the motion models are patient specific, which requires training the model every time for a new subject. Additionally, once the surrogate values during inference are out of the surrogate range for building the model, e.g. for abnormal motion, extrapolation is needed, which hamper accurate motion compensation.

SUMMARY

Accordingly, it is desirable to track the motion of the coronary tree in non-contrast enhanced fluoroscopic images in order to reduce the shortcomings as described above. Use of this method would better assist cardiologists during PCI and reduce the exposure of patients to the contrast agent as well as exposure to X-ray radiation.

It is thus an object of embodiments herein to provide computer implemented methods for dynamically visualizing information from first image data of an object of interest along with second image data of the object of interest, the methods comprising:

i) using the first image data to generate a plurality of roadmaps of the object of interest;

ii) determining a plurality of reference locations of a device in the first image data, wherein the plurality of reference locations correspond to the plurality of roadmaps of the object of interest of i);

iii) selecting a roadmap from the plurality of roadmaps;

iv) determining a location of the device in the second image data;

v) using the reference location of the device corresponding to the roadmap selected in iii) and the location of the device determined in iv) to transform the roadmap selected in iii) to generate a dynamic roadmap of the object of interest; and vi) overlaying a visual representation of the dynamic roadmap of the object of interest as generated in v) on the second image data for display.

Related systems and program storage devices are also described and claimed.

In embodiments, the device can be a guiding catheter, a guide wire or other intraluminal device or instrument which is present in the first image data and in the second image data.

In embodiments, the first image data can be acquired with a contrast agent, and the second image data can be acquired without a contrast agent.

In embodiments, the first image data covers at least one cardiac cycle of a patient, and the plurality of roadmaps of the object of interest covers different phases of the cardiac cycle of the patient.

In embodiments, the phases of the cardiac cycle of the patient are offset in time relative to a predefined part of the cardiac cycle of the patient.

In embodiments, the method(s) can further involve processing an ECG signal synchronous with the second image data, for example acquired together with the second image data, to determine a phase of the cardiac cycle of the patient that corresponds to the second image data. The roadmap can be selected in iii) by matching the phase of the cardiac cycle of the patient for the second image data to the phase of the cardiac cycle of the patient for the selected roadmap.

In embodiments, the method(s) can further involve processing the first image data to determine a phase of the cardiac cycle of the patient for an image frame and associating the phase of the cardiac cycle to a roadmap corresponding to the image frame.

In embodiments, the plurality of roadmaps of the object of interest can be a plurality of two-dimensional roadmaps or a plurality of three-dimensional roadmaps. For example, the plurality of three-dimensional roadmaps can be derived from a three-dimensional model of the object of interest. In another example, the plurality of three-dimensional roadmaps can be derived from two X-ray angiographic image sequences of the object of interest acquired with a contrast agent. In still another example, the plurality of three-dimensional roadmaps can be derived from a three-dimensional model of the object of interest and an X-ray angiographic image sequence of the object of interest acquired with a contrast agent.

In embodiments, the plurality of roadmaps can include information that characterizes properties (such as centerlines, contours and/or image mask) of the object of interest.

In embodiments, the plurality of roadmaps can include at least one measurement for the object of interest. For example, the at least one measurement can be selected from the group consisting of location and extent of vessel obstruction, diameter and area, pressure, blood velocity, fractional flow reserve, wall shear stress, vessel curvature, amount of foreshortening, location and extent and type of coronary plaque, location and extent of coronary total occlusion, or location and extent of coronary obstruction for the object of interest.

In embodiments, the location of the device in the second image data can be determined using a Bayesian filtering method. In one example, the Bayesian filtering method can employ a deep learning network to estimate the likelihood of the location of the device in the second image data. In another example, the Bayesian filtering method can be configured to equate location of the device in the second image data to the weighted arithmetic mean of a plurality of positions and their associated weights. In other examples, the Bayesian filtering method can be configured to resample points around a position with a high weight value.

In embodiments, the operations of v) apply a transformation to the roadmap selected in iii) in order to compensate for motion between the first image data and the second image data. For example, the motion can include breathing motion and/or cardiac motion and/or patient motion and/or table motion.

In embodiments, the transformation applied to the roadmap selected in iii) can be a rigid transformation or a non-rigid transformation that is based on a displacement obtained from the reference location of the device corresponding to the selected roadmap and the location of the device within the second image data.

In embodiments, the visual representation of the dynamic roadmap can be generating by projecting the overlay of the dynamic roadmap onto the second image data using a transparent mode, and/or dilating the dynamic roadmap and projecting the boundaries of the resultant dynamic roadmap onto the second image data, whereby the visual representation of the dynamic roadmap is configured to not obscure an interventional device or instrument used to treat the object of interest.

In embodiments, the plurality of reference points can be stored as part of the plurality of roadmaps of the object of interest.

In embodiments, the roadmap selected in iii) can be a three-dimensional roadmap that is transformed to generate at least one dynamic roadmap for overlay on the second image data. For example, the three-dimensional roadmap can be transformed according to viewpoint (e.g., viewing angles) used to acquire the second image data. This allows the second image data to be acquired from viewpoints different from the first image data.

In other embodiments, the roadmap selected in iii) can be a two-dimensional roadmap that is transformed to generate at least one two-dimensional dynamic roadmap for overlay on the second image data. In this case, the first image data and the second image data can be acquired from a common viewpoint.

In embodiments, the first image data can be derived by subtraction of a baseline image, and the second image data can be derived by subtraction of the baseline image.

In embodiments, the first image data can be angiographic image data acquired using an X-ray imaging modality with a contrast agent, and the second image data can be fluoroscopic image data acquired using an X-ray imaging modality without a contrast agent.

In embodiments, the operations of iii) to vi) can be repeated for successive frames of a live image sequence acquired without a contrast agent.

In embodiments, a roadmap can be selected for each respective image frame in successive image frames of the second image data for transformation and overlay in the image frames of the second image data for dynamic guidance. In other embodiments, one roadmap (the same roadmap) can be selected for successive image frames of the second image data for transformation and overlay in the image frames of the second image data for static guidance.

In embodiments, the device is selected from the group consisting of a guiding catheter, a guide wire, or other intraluminal device or instrument.

In embodiments, the location of the device corresponds to an end or tip of the device.

In embodiments, the object of interest is the heart, a part of the coronary tree, blood vessels or other part of the vasculature.

In embodiments, the method(s) can further involve displaying the overlay of the visual representation of the dynamic roadmap of the object of interest on the second image data.

Embodiments herein also relate to methods for visualizing information in image data of an object of interest of a patient, which involve:
i) obtaining first image data of the object of interest, wherein the first image data is acquired with a contrast agent and a device (such as a guiding catheter, a guide wire or other intraluminal device or instrument) is present in the first image data;

ii) using the first image data to generate a plurality of roadmaps of the object of interest;

iii) determining a plurality of reference locations of the device in the first image data, wherein the plurality of reference locations correspond to the plurality of roadmaps of the object of interest;

iv) obtaining second image data of the object of interest, wherein the second image data is acquired without a contrast agent and the device is present in the second image data;

v) selecting a roadmap from the plurality of roadmaps of the object of interest;

vi) determining a location of the device in the second image data;

vii) using the reference location of the device corresponding to the roadmap selected in v) and the location of the device determined in vi) to transform the roadmap selected in v) to generate a dynamic roadmap of the object of interest; and viii) overlaying a visual representation of the dynamic roadmap of the object of interest as generated in vii) on the second image data for display.

Embodiments herein also relate to systems for generating an image of an object of interest of a patient, comprising at least one processor that, when executing program instructions stored in memory, is configured to perform the operations of the methods according embodiments herein.

In an embodiment, the at least one processor is configured to:
i) obtain first image data of the object of interest, wherein the first image data is acquired with a contrast agent and a device (such as a guiding catheter, a guide wire or other intraluminal device or instrument) is present in the first image data;

ii) use the first image data to generate a plurality of roadmaps of the object of interest;

iii) determine a plurality of reference locations of the device in the first image data, wherein the plurality of reference locations correspond to the plurality of roadmaps of the object of interest;

iv) obtain second image data of the object of interest, wherein the second image data is acquired without a contrast agent and the device is present in the second image data;

v) select a roadmap from the plurality of roadmaps of the object of interest;

vi) determine a location of the device in the second image data;

vii) use the reference location of the device corresponding to the roadmap selected in v) and the location of the device determined in vi) to transform the roadmap selected in v) to generate a dynamic roadmap of the object of interest; and viii) overlay a visual representation of the dynamic roadmap of the object of interest as generated in vii) on the second image data for display.

In embodiments, the system can further include an imaging acquisition subsystem, typically using an X-ray imaging modality, configured to acquire the first image data and the second image data.

In embodiments, the system can further include a display subsystem configured to display the overlay of the visual representation of the dynamic roadmap of the object of interest as generated in viii) on the second image data.

Further improvements are the object of the dependent claims.

BRIEF DESCRIPTION OF THE DRAWINGS

FIG. 3 shows an illustration of the dynamic roadmap process.

FIG. 10a shows an example of the dynamic roadmapping.

FIG. 10b shows another example of the dynamic roadmapping.

FIG. 13 summarized the algorithm to track the catheter tip uses a deep learning based Bayesian filtering method.

FIG. 19 shows some example of the generation of the 3D model based on 3D angiographic image data.

FIG. 23 shows a guidance map in the selection of an optimal second projection with respect to the first projection.

FIG. 25 shows two example of 3D segmentation of the coronary lumen including segmentation of coronary plaque.

FIG. 34b shows some example of superimposing of the roadmap on X-ray angiographic image data.

DETAILED DESCRIPTION OF ILLUSTRATIVE EMBODIMENT(S)

This present application describes method(s) and system(s) to provide a real time dynamic overlay or dynamic coronary roadmap which can be superimposed on the live X-ray fluoroscopic or angiographic image stream/sequence and thereby providing support for the clinician in improved patient treatment. The approach compensates changes in vessel shapes and cardiac motion by selecting a roadmap of the same cardiac phase through temporal alignment, and corrects the respiratory induced motion and patient motion via tracking a device.

Figure 9:
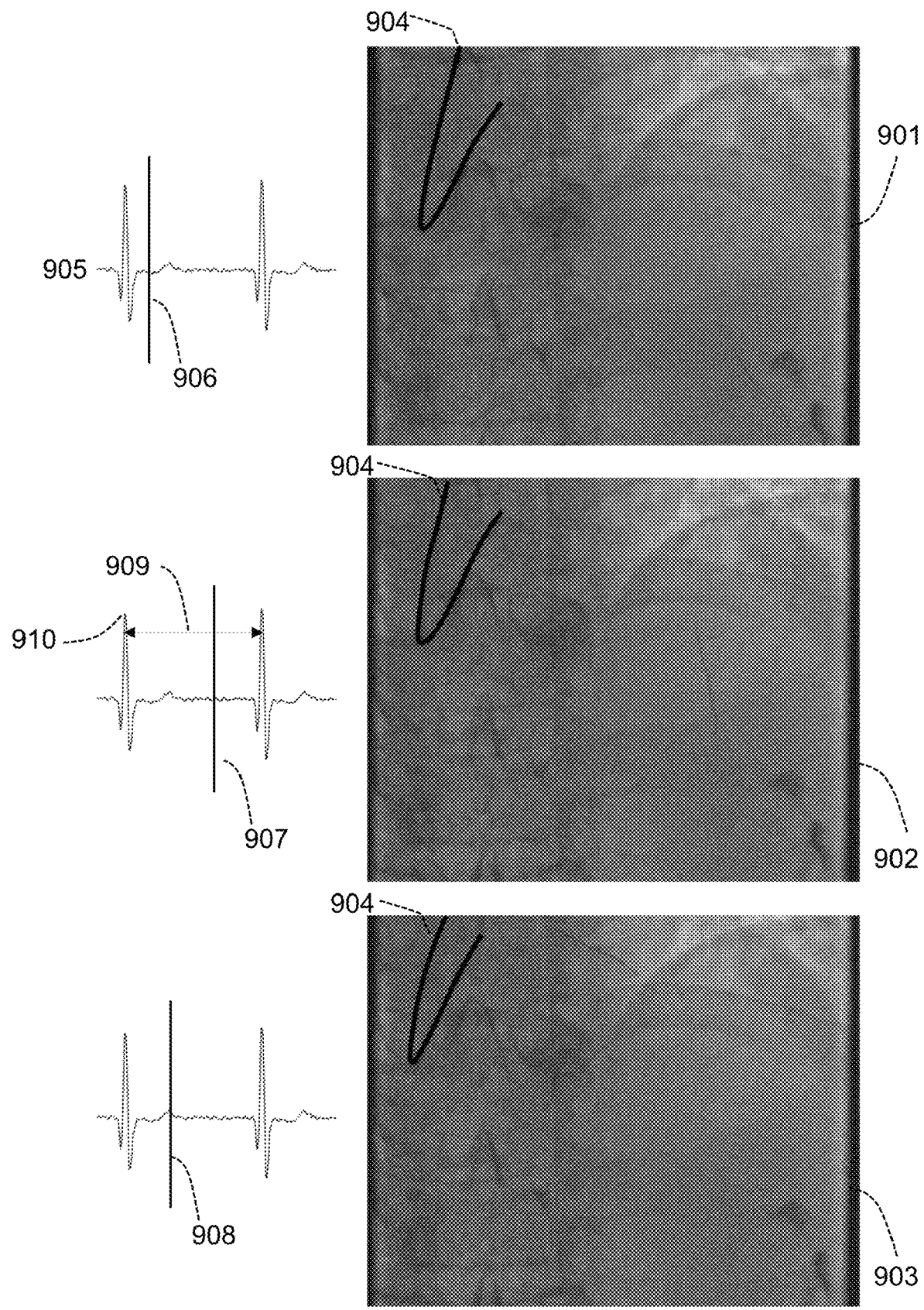
FIG. 9 shows an example of some X-ray fluoroscopic image frames and its acquisition time with respect to the cardiac cycle within an X-ray fluoroscopic image sequence.

In the description of the methodology and systems below, X-ray angiography will be used to refer to an X-ray acquisition of an object of interest (e.g., a part of the vasculature or a coronary vessel tree) after administration of a contrast agent resulting in visualization of the object of interest and other objects which are radiopaque. X-ray fluoroscopy refers to X-ray image acquisition without the use of a contrast agent and therefore contains no enhance visualization of the object of interest. The term image or image frame refers to a single image, and the term image sequence or image stream refers to a multiple images acquired over time. The X-ray angiography image sequence may contain the contrast agent administration, and image frame which precedes the contrast agent administration will contain no contrast agent and thus no enhancement of the vasculature. The X-ray angiography image sequence may comprise multiple frames covering one or more phases of the cardiac cycle. Throughout this patent application, a cardiac cycle is specific to a patent and is defined as the period in which covers one heartbeat of the patient. The cardiac cycle can be defined as the period of time between successive R-tops within the ECG signal of the patient. A phase refers to a moment (or period) of time within the cardiac cycle of the patient. Phase can be measured as an offset from R-top within the ECG signal of the patient as shown in FIG. 9 and its corresponding description.

Within this application a method is proposed to generate and display the dynamic overlay or dynamic roadmap as an overlay on the live X-ray image stream, which consists of the following elements:

Construct a model of the organ of interest (such as a coronary tree) from angiographic image sequence of the organ of interest;

Select a part (or frame) of the model that is aligned with the cardiac phase of the patient using electrocardiogram (ECG) measurements of the patient;

Update or transform the selected model part to compensate for respiratory motion using guiding catheter tracking in live X-ray fluoroscopic or angiographic image stream of the patient;

Render the resulting model part and integrate the rendered view of the model as an overlay on the live X-ray fluoroscopic or angiographic image stream of the patient.

The described dynamic coronary roadmap method runs in real-time with a graphics processing unit (GPU), and thus can be used during PCI in real clinical settings.

Figure 1:
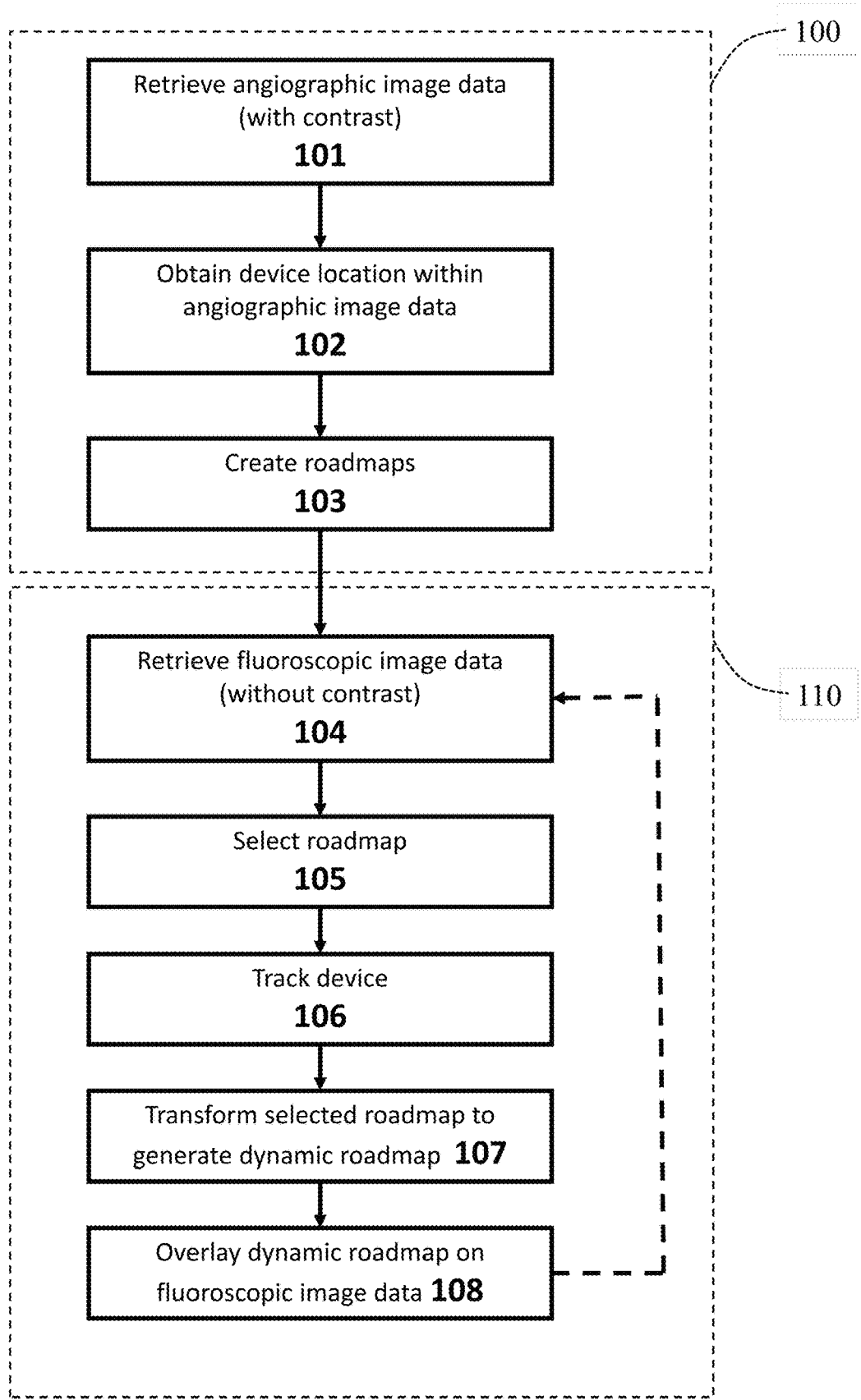
FIG. 1 shows a flow chart of a method for determining a dynamic coronary roadmap in accordance with an embodiment herein.

FIG. 1 shows a flow chart illustrating the operations according to an embodiment of the present application. The operations employ an imaging system capable of acquiring and processing two-dimensional image sequences of a vessel organ (or portion thereof) or other object of interest. For example a single plane or bi-plane angiographic system can be used such as those manufactured, for example, by Siemens (Artis zee Biplane) or Philips (Allura Xper FD).

Figure 2A:
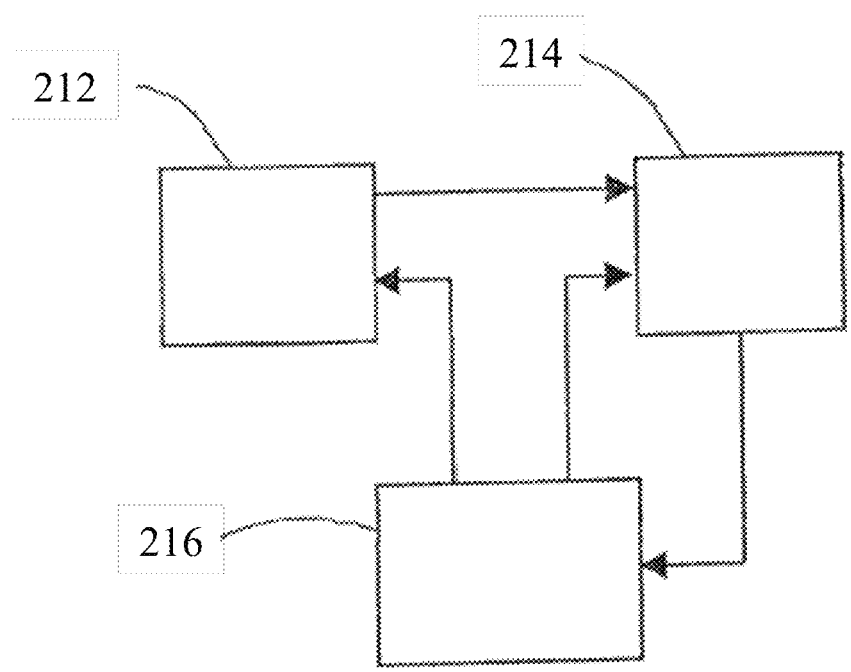
FIG. 2a shows a functional block diagram of an exemplary single plane angiographic system in accordance with embodiments herein.

FIG. 2a is a functional block diagram of an exemplary single plane angiographic system, which includes an angiographic imaging apparatus 212 that operates under commands from user interface module 216 and will provide data to data processing module 214. The single plane angiographic imaging apparatus 212 captures a two-dimensional X-ray image sequence of the vessel organ of interest for example in the postero-anterior direction. The single plane angiographic imaging apparatus 212 typically includes an X-ray source and detector pair mounted on an arm of a supporting gantry. The gantry provides for positioning the arm of the X-ray source and detector at various angles with respect to a patient who is supported on a table between the X-ray source and detector. The data processing module 214 may be realized by a personal computer, workstation or other computer processing system. The data processing module 214 processes the two-dimensional image sequence captured by the single plane angiographic imaging apparatus 212 to generate data as described herein. The user interface module 216 interacts with the user and communicates with the data processing module 214. The user interface module 216 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 214 and the user interface module 216 cooperate to carry out the operations of FIG. 1, FIG. 15, FIG. 18, FIG. 26 or FIG. 28 as described below.

The operations of FIG. 1, FIG. 15, FIG. 18, FIG. 26 or FIG. 28 can also be carried out by software code that is embodied in a computer product (for example, an optical disc or other form of persistent memory such as a USB drive or a network server). The software code can be directly loadable into the memory of a data processing system for carrying out the operations of FIG. 1, FIG. 15, FIG. 18, FIG. 26 or FIG. 28. Such data processing system can also be physically separated from the angiographic system used for acquiring the images making use of any type of data communication for getting such images as input.

In this example it is assumed that the imaging system has acquired and stored at least one two-dimensional image sequence of an object of interest. Any image device capable of providing two-dimensional angiographic image sequences can be used for this purpose. For example a biplane or single plane angiographic system can be used such as those manufactured, for example, by Siemens (Artis zee Biplane) or Philips (Allura Xper FD).

Figure 2B:
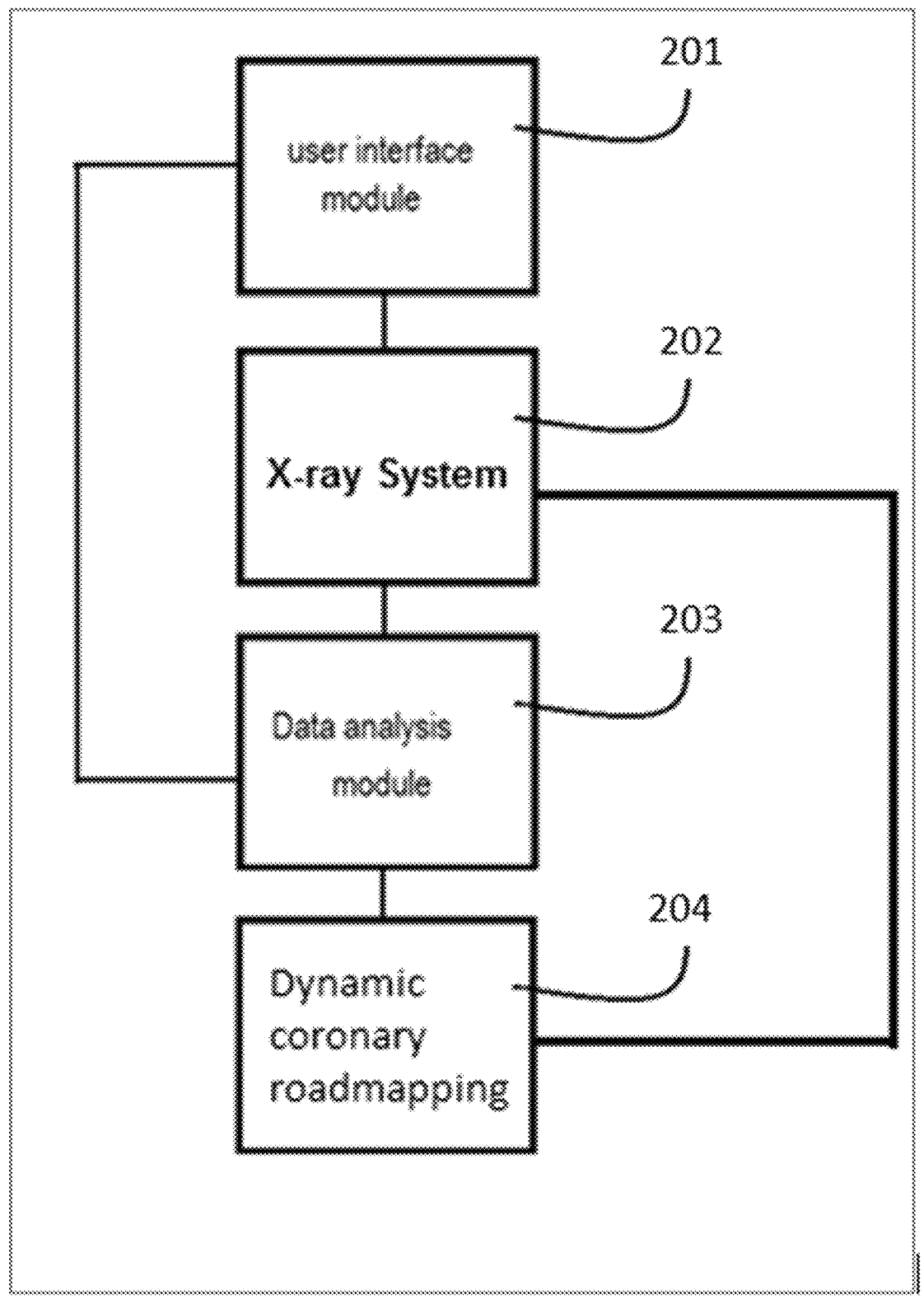
FIG. 2b shows a functional block diagram of an X-ray system connected to a system containing the embodiments herein.

FIG. 2b is an alternative functional block diagram of an exemplary in accordance to an embodiment herein which includes an X-ray system 202 that operates under commands from the user interface module and provide data to the data analysis module 203. The X-ray system 202 acquires X-ray image data of a region of interest for instance the heart. The data analysis module 203 may be realized by a personal computer, workstation or other computer processing system. The data analysis module 203 processes the acquired X-ray image data of the X-ray system 202 to generate, for instance, coronary roadmap or coronary analysis quantification. The user interface module 201 interacts with the user and communicates with the data analysis module 203. The user interface module 201 can include different kinds of input and output devices, such as a display screen for visual output, a touch screen for touch input, a mouse pointer or other pointing device for input, a microphone for speech input, a speaker for audio output, a keyboard and/or keypad for input, etc. Module 204 represent the dynamic coronary roadmap, representing the coronary tree computed from the acquired X-ray image data as described by current application. The dynamic coronary roadmap is real time superimposed on the X-ray image sequence as acquired by the X-ray system module 202. The module 204 may be realized by a personal computer, workstation or other computer processing system and interacts with the X-ray system 202.

An embodiment is now disclosed with reference to FIG. 1. The therein-depicted operations can, obviously, be performed in any logical sequence and can be omitted in parts. As it is an objective of the application to provide a workflow that can be used during the interventions, workflow example steps will also be referenced. In a preferred embodiment, the method of this application assumes a scenario of performing dynamic coronary roadmapping to guide a PCI procedure. As can be seen in FIG. 1, the workflow comprises of number of steps which represents an offline phase and an online phase. The offline phase, represented by block 100 in FIG. 1, creates a set of coronary artery roadmaps using an X-ray angiography sequence obtained with injection of contrast agent over multiple cardiac phases. The online phase, represented by block 110 in FIG. 1, uses the set of roadmaps created in the offline phase in conjunction with an X-ray angiography sequence obtained without injection of contrast agent to create a dynamic roadmap based on tracking the position of a device. A visual representation of the dynamic roadmap is overlaid on the live fluoroscopic image stream of the X-ray fluoroscopic image sequence in order to provide visual guidance to the physician to provide support for placement of one or more medical instruments inserted through a guiding catheter. For example, the medical instrument(s) can be a guidewire, dilation balloon, stent or other suitable intravascular device or instrument.

Before explanation of each step of FIG. 1 in detail a short summary is provided which explains on high level the sub steps within the offline and online phase.

Offline Phase:

The offline phase, represented by block 100 in FIG. 1, is performed before the actual roadmapping is conducted. In the offline phase, roadmaps of coronary arteries over multiple phases of the cardiac cycle are created from an X-ray angiographic image sequence that covers the multiple phases of the cardiac cycle. Typically, at least one cardiac cycle is taken into account. Along with the X-ray angiography sequence, temporal information (e.g. ECG signals) of the cardiac cycle are obtained and stored. A roadmap includes information that characterizes properties of the coronary arteries for a given phase of the cardiac cycle. Such information can include centerlines for the coronary arteries, contours (luminal boundary) of the coronary arteries over respective lengths of the coronary arteries, and/or a mask image that represents the coronary arteries (e.g., an image that covers the space occupied by the coronary arteries). In embodiments, the roadmap can include a vessel model in the form of centerlines, contours, and/or mask image which represents the coronary arteries for a given phase of the cardiac cycle. One or more of the roadmaps may also contain information of clinical interest, e.g. location and percentage of vessel obstruction, diameter and area, pressure, blood velocity, fractional flow reserve, wall shear stress, the curvature of the vessel, amount of foreshortening, the location and amount and type of coronary plaque (e.g. calcified, soft plaque, mixed-plaque), location and extent of coronary total occlusion, or location and extent of coronary obstruction. The creation of the roadmaps will be described in more detail by step 103 of FIG. 1.

A device location (e.g. the catheter tip location) within the X-ray angiography sequence is obtained and associated with the roadmaps to serve as a reference point for roadmap transformation (as described in more detail by step 107 of FIG. 1). This reference point (device location), as described in more detail by step 102 of FIG. 1, can be integrated into the roadmaps.

Online Phase:

During the online phase, represented by block 110 in FIG. 1, the dynamic roadmapping is actually performed. In the online phase, a sequence of X-ray fluoroscopic image data is acquired without the use of contrast agent and preferably at the same view angles (C-arm angulation and C-arm rotation) as the roadmaps were created during the offline phase (see step 104 of FIG. 1). At the same time, ECG signals are obtained along with the X-ray fluoroscopic image data and compared with the stored ECG to select the best matching roadmap (step 105 in FIG. 1) as created in the offline phase. This is to compensate the change of vessel shape and position between frames due to cardiac motion. Simultaneously, the device location (e.g. catheter tip location) in the acquired X-ray fluoroscopic image data is tracked using image processing techniques and in a preferred embodiment using the proposed deep learning based Bayesian filtering method as described in step 106 in FIG. 1. The displacement of device location (e.g., catheter tip) between the current frame of X-ray fluoroscopic image data and the reference point (device location) associated with the selected roadmap is obtained and applied to transform the selected roadmap to generate a dynamic roadmap as described by step 107 of FIG. 1. Finally, a visual representation of the dynamic roadmap is rendered and overlaid on the current frame of the X-ray fluoroscopic image data to guide the PCI procedure (step 108 in FIG. 1).

An illustration of the dynamic roadmap process is presented in FIG. 3. Within FIG. 3, the offline phase is represented by picture 301 and 302, in which 301 illustrates an X-ray angiographic image sequence of the right coronary artery and 302 the generated roadmap from the X-ray angiographic sequence (301). During the online phase, illustrated by picture 303 and 304, the generated roadmap (302) is superimposed on the X-ray fluoroscopic image stream (303) resulting in a dynamic coronary roadmap (304). For illustration, only one frame (representing one moment within the cardiac cycle) is presented within FIG. 3.

In the following sections, the steps describes by FIG. 1 are explained in more detail.

Step 101: Retrieve Angiographic Image Data

In the first step, step 101, the angiographic image data is retrieved. Within a preferred embodiment the angiographic image data represents the acquisition of an object of interest by means of X-ray angiography, resulting in an X-ray angiographic image sequence. For example a single plane or bi-plane angiographic system can be used such as those manufactured, for example, by Siemens (Artis zee Biplane) or Philips (Allura Xper FD). The object of interest is for example the heart, a part of the coronary tree, or blood vessels and by means of a contrast medium the object of interest is visualized during the acquisition. The X-ray angiography image sequence is acquired in such a way that the object of interest is clearly visible. Therefore, the C-arm can be rotated and angulated by the clinician to obtain the best projection. Preferably, the electrocardiogram (ECG) is part of the angiographic image data and is simultaneously recorded during the X-ray angiography acquisition. The ECG enables cardiac phase matching between different X-ray angiography frames or X-ray angiography acquisitions. With cardiac phase matching the object of interest displacement due to cardiac motion between image frames in the same cardiac phase is minimized.

Figure 4:
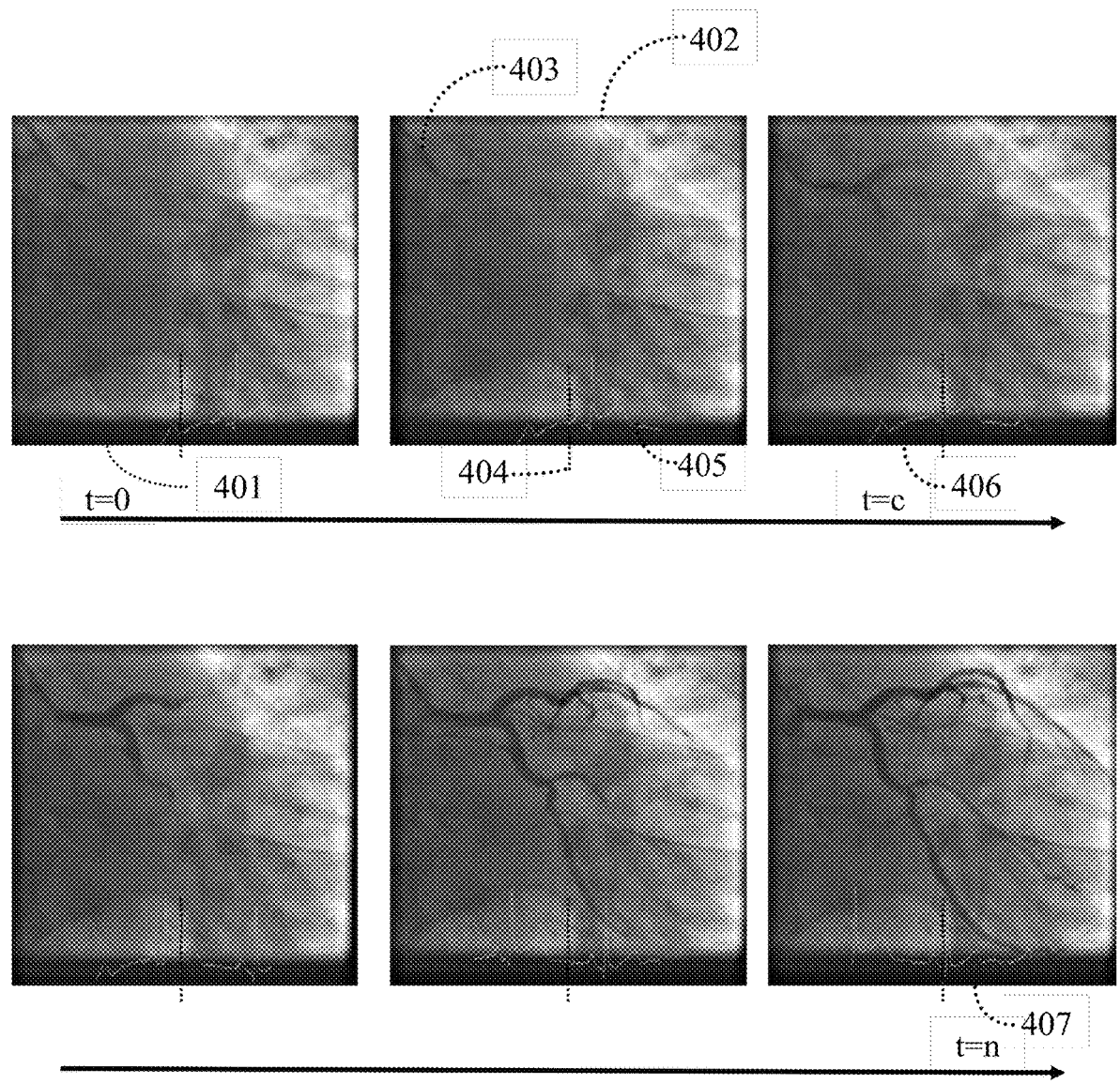
FIG. 4 shows an illustration of a retrieved angiographic image data.

FIG. 4 provides an illustration of a retrieved angiographic image data, which consist of an X-ray angiographic image sequence including the ECG signal. Picture 401 shows the first X-ray image frame as acquired at t=0. Picture 402 shows another X-ray image frame from the x-ray angiographic image sequence at time t>0. Within picture 402, a device is visible and in this example the device represents a guiding catheter (403). Within a PCI procedure, the guiding catheter is used to inject the contrast liquid and the guiding catheter is used to facilitate the placement of lasers, stents, and balloons for angioplasty or other devices or instruments. In general an X-ray angiographic image sequence contains an amount of X-ray image frames before injection of contrast liquid and an amount of X-ray image frame after injection of contrast liquid, both containing preferable at least one cardiac cycle. The ECG signal (405) is visualized in each frame of FIG. 4, and the time with the respect to the ECG signal in which a particular image frame is acquired is represented by 404. Within FIG. 4, picture 406 shows an X-ray image frame at the moment that the contrast liquid enters the coronary artery at time t=c, and picture 407 shows the last X-ray image frame within the X-ray angiographic image sequence at time t=n. The temporal resolution of an X-ray system is typically 15 frames per second. In case the patient's heartrate is 60 beats per minute, an X-ray angiographic image sequence which covers five cardiac cycles will contain 75 X-ray image frames.

Step 102: Obtain Device Location within Angiographic Image Data

There is a number of factors that can cause displacement of the object of interest or the roadmap between successive X-ray image frames within an X-ray angiographic image sequence or between different X-ray angiographic image sequences. These factors are cardiac motion due to contraction of the heart, breathing motion due to respiration of the patient and patient motion due to patient movement. Cardiac motion is compensated by matching the cardiac phase using for example the retrieved ECG signal. Breathing motion, including possible patient motion, can be compensated by identifying a reference point in the image. The reference point (represented by a visible device in the image sequence) will be used for transformation of the object of interest or the roadmap during the online phase. The reference point could be for example be the catheter tip, pacemaker or anatomical landmarks or any other object in which its motion can be correlated to the breathing motion and possible patient motion. Such a reference point can be obtained in every frame of the X-ray angiographic image sequence. Identification of the reference point in a frame might be done manually. Alternatively to a manual identification of the reference point, image processing techniques might be applied to detect objects or landmarks in medical image data for example as described by step 503 of FIG. 5.

Figure 5:
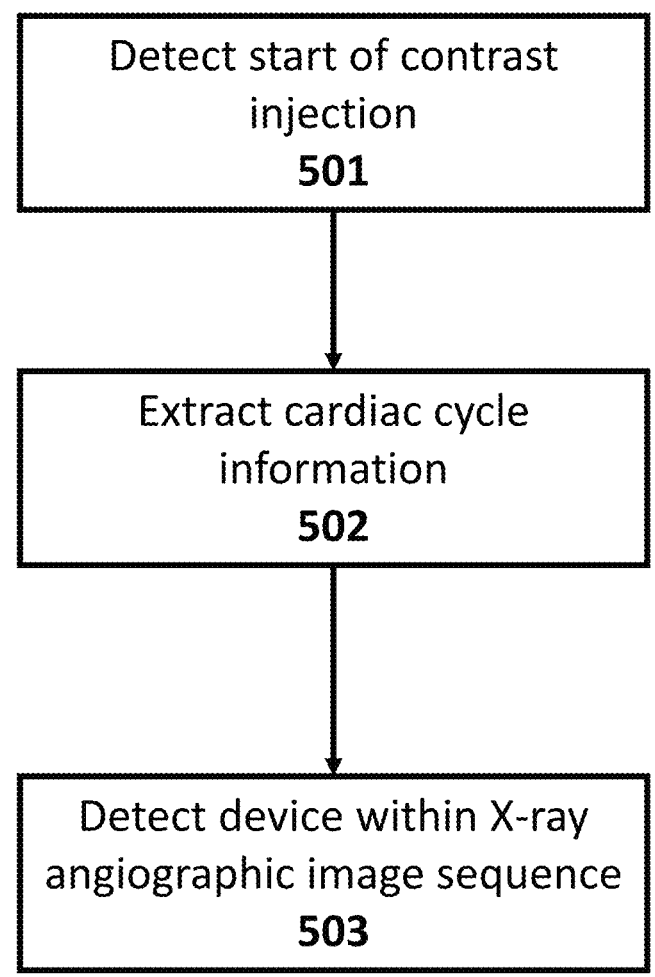
FIG. 5 shows a flow chart of a method to obtain the device location within an X-ray angiographic image sequence.
Figure 6:
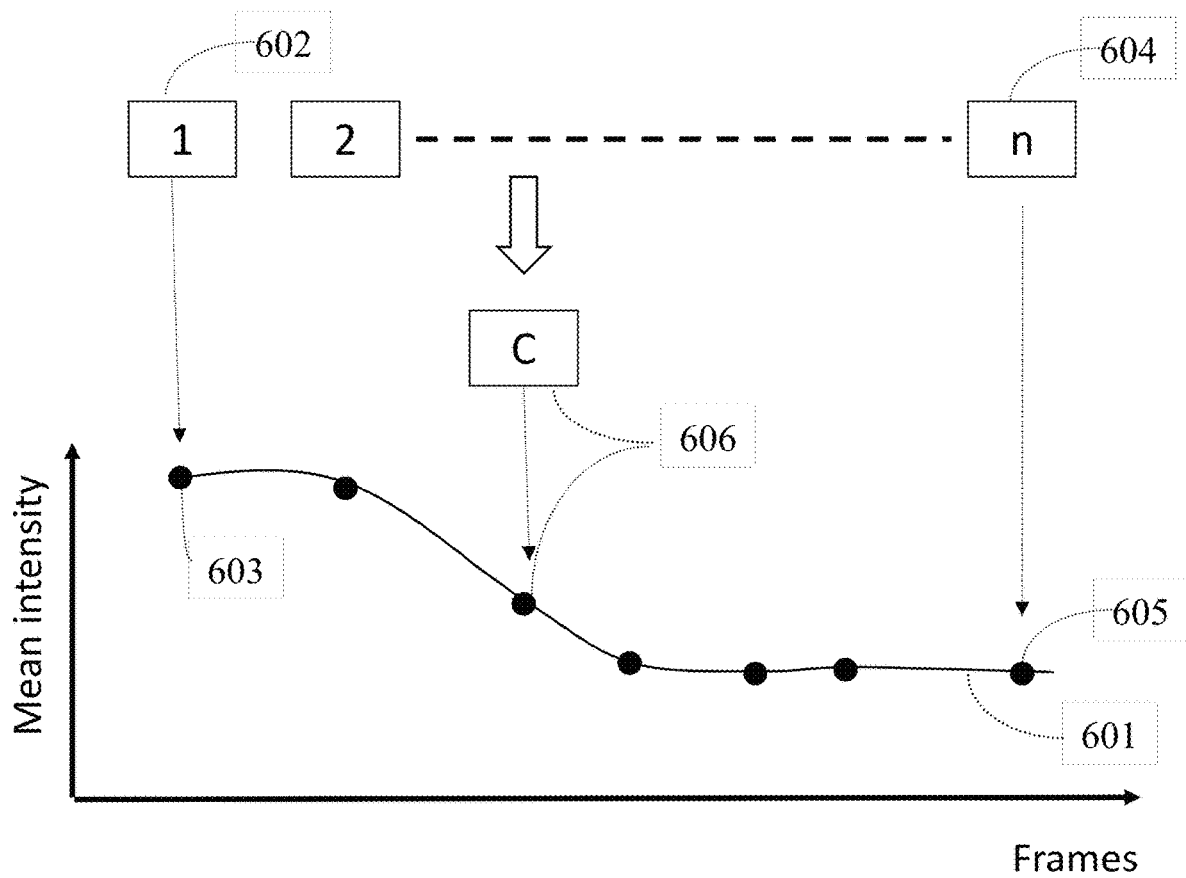
FIG. 6 shows an example of a method to detect the start of contrast injection frame within an X-ray image sequence.

Within a preferred embodiment, the steps to obtain the device location within an X-ray angiographic image sequence are illustrated by the flowchart of FIG. 5. At step 501 of FIG. 5, the frame within the X-ray angiographic image sequence in which the contrast liquid enters the coronary tree (406 of FIG. 4) is detected. FIG. 6, illustrates a method to detect the start of contrast injection frame. For each frame within the X-ray angiographic image sequence, the mean pixel intensity is computed and visualized by graph 601. For instance, the mean pixel intensity of the first frame (602) is represented by 603 and the mean pixel intensity of frame n (604) is represented by 605. Within FIG. 6, the frame in which the contrast liquid enters the coronary artery is represented by 606. Since contrast liquid is radiopaque, it absorbs X-ray radiation, and the vessel will appear darker (black corresponds to a low pixel intensity, and white corresponds to a high pixel intensity) than its surroundings, resulting in a lower mean pixel intensity of the image frame. The frame in which the contrast liquid enters the coronary tree can then be identified as the frame in which the first derivative of curve 601 is minimum and represented by 606 in FIG. 6. Alternatively, the curve 601 can be generated by a method in which pixels that represent tubular structures, such as vessel and catheters, are weighted more pronounced as for example by the equation 1:

$$f(\text{frame}) = \frac{1}{n}\Sigma_1^n(\text{Median}_{(frame)} - I_{(frame)}(n)\,\omega_{(frame)}(n))^c \quad \text{(equation 1)}$$

where $\text{Median}_{(frame)}$ represent the median of an image frame, $I_{(frame)}(n)$ represents a pixel n within an image frame, c represent a constant, and $\omega_{(frame)}$ represents a weighting function of an image frame in which the likelihood of tubular structures are represented; zero means low likelihood of tubular structures and 1.0 represent a high likelihood of tubular structures. The likelihood can be calculated by for instance by applying a Frangi vesselness filter (Frangi et al., "*Multiscale Vessel Enhancement Filtering*", Medical Image Computing and Computer-Assisted Intervention—MICCAI 1998 Lecture Notes in Computer Science 1496/1998:130).

Another approach to detect the frame within the X-ray angiographic image sequence in which the contrast liquid enters the coronary tree is the method as taught by Ma, et al., "*Fast prospective detection of contrast inflow in x-ray angiograms with convolutional neural network and recurrent neural network*", International Conference on Medical Image Computing and Computer-Assisted Intervention, Springer (2017) 453-461. In this work, Ma et al. describes two different approaches for detection of the frame within an image sequence in which the contrast first appears. The first approach trains a convolutional neural network (CNN) to distinguish whether a frame has contrast agent or not. The second approach extracts first contrast features from images with enhanced vessel structures and the contrast frames are then detected based on changes in the feature curve using long short-term memory which is established by a recurrent neural network architecture.

Figure 7:
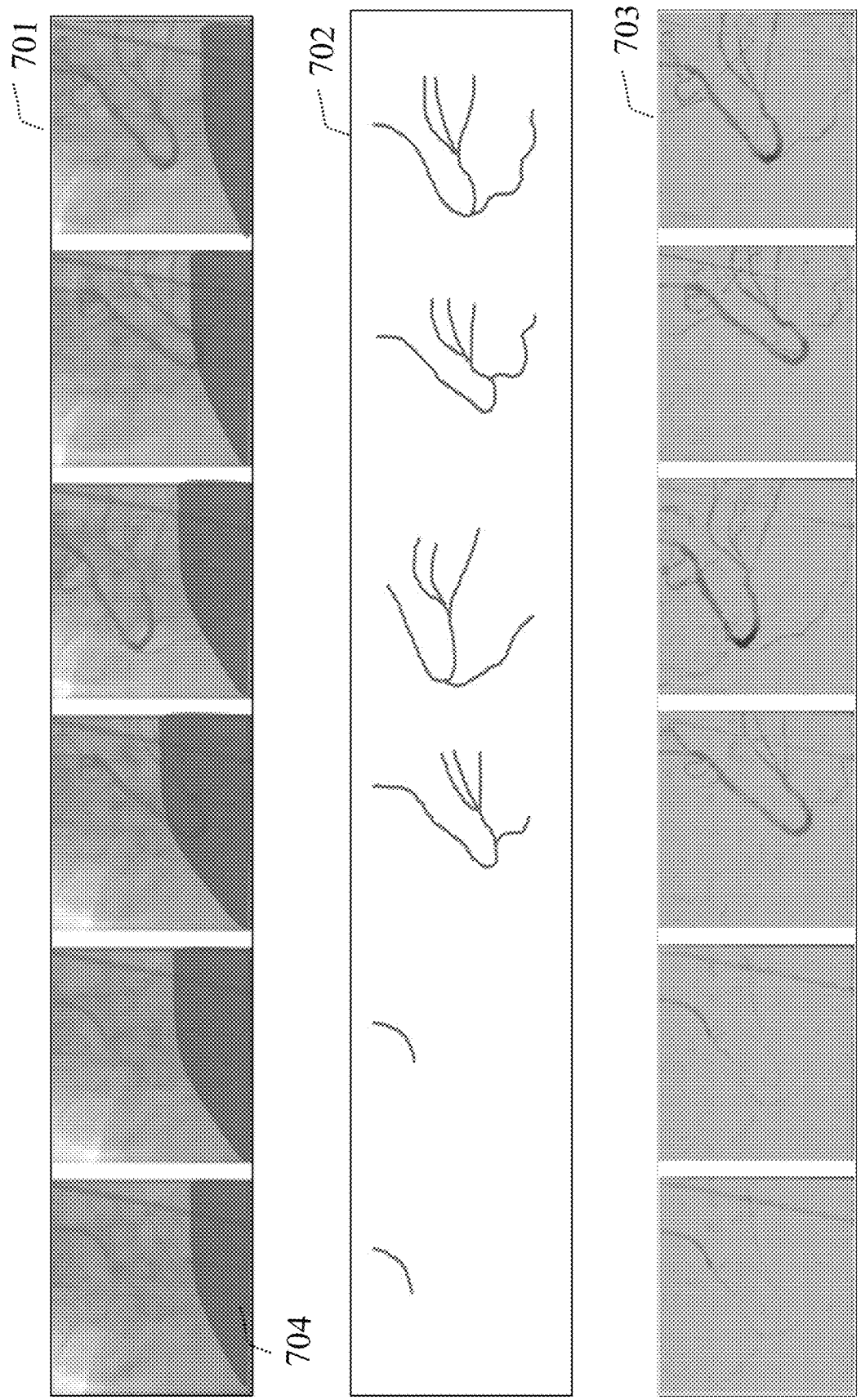
FIG. 7 shows some approaches to extract the cardiac cycle within successive X-ray image frames.

Next, in step 502 the cardiac cycle information is extracted from the X-ray angiographic image sequence. In case the ECG signal is part of the angiographic image data (101 of FIG. 1), this step is omitted. As mentioned before, coronary motion exists of cardiac motion due to contraction of the heart, breathing motion due to respiration of the patient and patient motion due to patient movement. To extract cardiac cycle information, only the motion of the coronary artery and/or the device such as the guiding catheter should be considered. Therefore, cardiac motion surrogate extraction by means of analyzing the motion pattern of objects representing cardiac motion, such as coronary tree and catheter, provides information on the cardiac cycle within an x-ray angiographic image sequence. Within FIG. 7, 701 represent a number of successive X-ray image frames within an X-ray angiographic image sequence. The movement of the diaphragm 704 is visible within the successive X-ray image frames 701.

One approach to extract the cardiac cycle information is illustrated by 702 of FIG. 7. Picture 702 represent the extracted coronary arteries and catheter from the image frames of 701. This can be achieved by applying a Frangi vesselness filter (Frangi et al., "*Multiscale Vessel Enhancement Filtering*", Medical Image Computing and Computer-Assisted Intervention—MICCAI 1998 Lecture Notes in Computer Science 1496/1998:130) followed by a non-maximum suppression (for example as taught by Li et al., "*Skeletonization of gray-scale image from incomplete boundaries*", Proceedings of the International Conference on Image Processing, ICIP 2008, Oct. 12-15). Next, the extracted coronary arteries between each successive frame are registered to each other (as for instance by means of a 2D registration technique as taught by Maintz et al., "*An overview of Medical Image registration Methods*") and from this information a function f(frame) is build that contains the displacement value between each successive frame. By applying a Fourier transform, both the cardiac motion can be separated from the breathing motion or patient motion.

Within FIG. 7, picture 703 illustrates another approach to extract the cardiac cycle information. In this situation, the images are processed in such a way that structures which does not represent cardiac motion are eliminated and vessels are enhanced. In this situation, cardiac motion becomes the major source of intensity change in the image sequence and can be further analyzed with methods having source decomposition capability such as principle component analysis. First, the image sequence 701 is processed in such a way that only vessels and devices such as catheters are enhanced (703). This can be performed by using a layer separation method as taught by Hao et al., "*Vessel Layer Separation in X-ray Angiograms with Fully Convolutional Network*", Proc. SPIE 10576, Medical Imaging 2018: Image-Guided Procedures, Robotic Interventions, and Modeling, or by Ma et al., "*Layer separation for vessel enhancement in interventional X-ray angiograms using morphological filtering and robust PCA*", Workshop on Augmented Environments for Computer-Assisted Interventions 2017, Springer. pp. 104-113 or by Ma et al., "*Automatic online layer separation for vessel enhancement in X-ray angiograms for percutaneous coronary interventions*", Med Image Anal. 2017 July; 39:145-161. Principal component analysis is typically used for dimension reduction. It transforms a multivariate dataset to a new orthogonal coordinate system such that most variance of this dataset could be represented by a few coordinates. Hence, reducing its dimension is normally achieved by preserving only a few coordinates in the new coordinate system without losing much information. Principal component analysis is used on the post processed images (703) to obtain principal components for the image sequence. Representing a frame of the sequence with an n×n matrix, each pixel in such matrix is concatenate into a single column vector $x^i$, whose size is D×1, where D=$n^2$. Thus, a sequence consisting of N frames is represented as a D×N matrix X=[$x^1$, ..., $x^N$]. Seeking the principal components of X is equivalent to computing the eigenvectors of covariance matrix $XX^T$, which is a D×D matrix. As D is usually a large number and in our case D>>N, eigen analysis is applied to the N×N matrix $X^TX$.

$$E = X\tilde{E}\nabla^{-1} \quad \text{(equation 2)}$$

where E is the D×N matrix of eigenvectors of $XX^T$, $\tilde{E}$ is the N×N matrix of eigenvectors, and $\nabla$ is the N×N diagonal matrix of eigenvalues of $X^TX$.

Next, the post processed sequence (703) is projected on the first principal component $e_1$ by computing $$p = X^T e_1 \quad \text{(equation 3)}$$

where $e_1$ is the first column of E representing the direction of the largest variance and p is a N×1 projection vector. So each frame in such sequence is represented by an element in vector p. The assumption underlying the described approach is that cardiac motion is the major source of variation in these sequences (703) where respiratory motion and patient motion are eliminated. Therefore, p is used as the cardiac motion surrogate representing the cardiac motion within the image sequence 701.

Referring back to FIG. 5, the next step is to detect the device within the X-ray angiographic image sequence. Within at least an amount of successive frames representing once cardiac cycle ($N_d$), the device location is detected. The device can be for example the catheter tip, pacemaker or anatomical landmarks or any other object within the image sequence in which its motion can be correlated to the breathing motion and possible patient motion. In a preferred embodiment the device is the catheter tip. One method to detect the device within the frames $N_d$ is by manually identifying the device, e.g. the catheter tip, within the frames $N_d$ by the clinician or a person who assists the intervention, such as a technician or a nurse.

Another method to detect the device (e.g. the catheter tip) within frames $N_d$ is by manually identifying the catheter tip in one frame, and propagate this location to the remaining frames within $N_d$ by means of image processing techniques for example as taught Zang et al., "*Cascade Attention Machine for Occluded Landmark Detection in 2D X-Ray Angiography*", Jan. 2019 IEEE Winter Conference on Applications of Computer Vision (WACV).

Another method to detect the device (e.g. the catheter tip) may be performed by model based detection, or use of convolution neural networks. Detection of the catheter tip might be improved by incorporating temporal information in the preprocessing or post processing. A fully automatic catheter segmentation technique based on convolutional neural network and including temporal information is taught by Ambrosini et al., "*Fully automatic and real-time catheter segmentation in X-ray fluoroscopy*", International Conference on Medical Image Computing and Computer-Assisted Intervention 2017, Springer. pp. 577-585.

Another method to detect the device (e.g. the catheter tip) is by first selecting an amount of successive frames representing once cardiac cycle before the frame in which the contrast enters the coronary artery (as described by step 501 of FIG. 5) from the angiographic image sequence ($N_{d\_before-contrast}$). Next, the catheter tip within frames $N_{d\_before-contrast}$ is automatically detected by the method as described further in detail at step 106 of FIG. 1.

Referring back to FIG. 1, the next step (103) is to create the roadmaps. Within step 103, the device location will be integrated in the created roadmaps to serve as reference point for the roadmap transformation (as described in more detail by step 107 of FIG. 1).

Step 103: Create Roadmaps

Within step 103, the X-ray angiographic image sequence is processed to create roadmaps of coronary arteries for multiple phases of the cardiac cycle after the frame in which the contrast liquids enters the coronary artery. Typically, the roadmaps are created for an amount of frames covering at least one cardiac cycle.

For example, the coronary artery roadmap can include a vessel model. The vessel model can represent the vessels centerlines, or the vessels boundary (contours), or a mask image which represents the vessels. Furthermore, the vessel model can also include clinically relevant information, such as for example location and percentage of vessel obstruction, and/or diameter, area, length of the vessel or the curvature of the vessel, and/or the location and amount of calcified plaque.

In embodiments, the coronary artery roadmap can be created for all frames within one cardiac cycle after contrast injection. For example, a full cardiac cycle can be selected within the X-ray angiography image sequence (as a result from step 101) after the frame in which the contrast liquids enters the coronary artery (as a result of step 501 of FIG. 5) and further referred to as $N_{after-contrast}$. Within frames $N_{after-contrast}$ a roadmap may be created using the layer separation method. A layer separation method uses for instance morphological filtering and principal component analysis to separate the X-ray angiographic image frame (801, FIG. 8) into three layers: 1) a large-scale breathing structure layer (802, FIG. 8), 2) an almost-static background layer (803, FIG. 8) and 3) a layer containing the vessel structures (804, FIG. 8).

Figure 8:
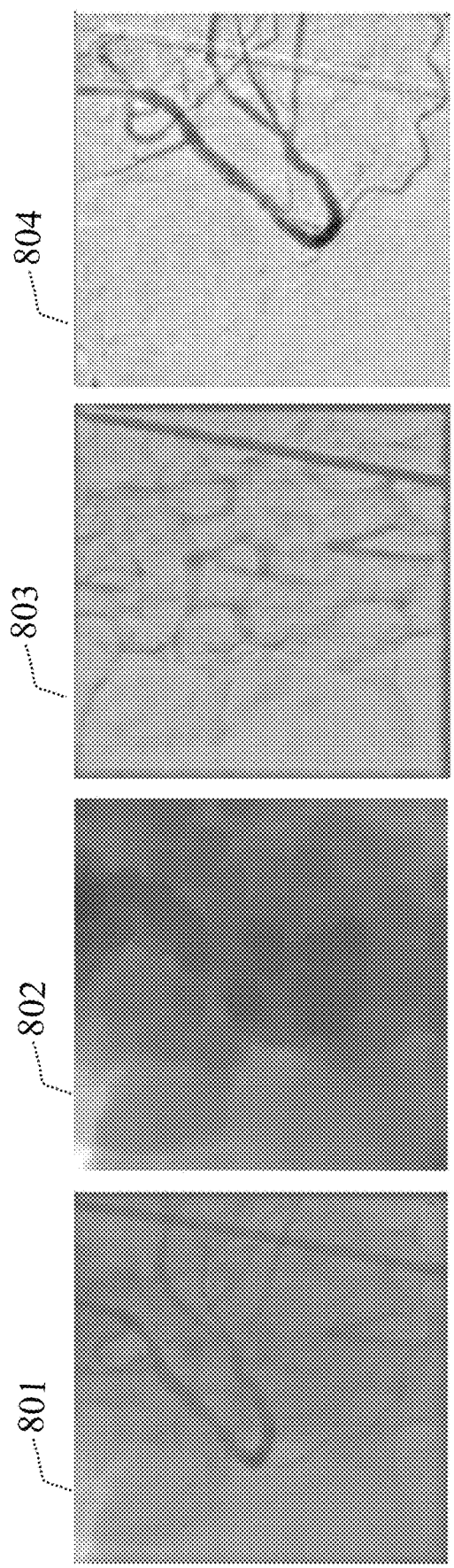
FIG. 8 shows an example of layer separation on an X-ray angiographic frame.

FIG. 8 shows an example of layer separation on an X-ray angiographic frame. It can be seen that, compared to the original X-ray angiographic image frame (801, FIG. 8), that the coronary arteries are significantly enhanced in the vessel layer (804, FIG. 8). Such layer separation method are for instance taught by Hao et al., "*Vessel Layer Separation in X-ray Angiograms with Fully Convolutional Network*", Proc. SPIE 10576, Medical Imaging 2018: Image-Guided Procedures, Robotic Interventions, and Modeling, or by Ma et al., "*Layer separation for vessel enhancement in interventional X-ray angiograms using morphological filtering and robust PCA*", Workshop on Augmented Environments for Computer-Assisted Interventions 2015, Springer. pp. 104-113 or by Ma et al., "*Automatic online layer separation for vessel enhancement in X-ray angiograms for percutaneous coronary interventions*", Med Image Anal. 2017 July; 39:145-161. Within FIG. 3, 302 provides an examples of the creation of a roadmap of the X-ray image 301 by means of layer separation.

Another approach to create the roadmap is by applying image processing skeleton techniques as for instance taught by Li et al., "*Skeletonization of gray-scale image from incomplete boundaries*", Proceedings of the International Conference on Image Processing, ICIP 2008, Oct. 12-15). Another approach to create the roadmap is by utilizing deep learning techniques as for instance taught by Nasr-Esfahani et al., "*Vessel extraction in X-ray angiograms using deep learning*", Conf Proc IEEE Eng Med Biol Soc. 2016 August; 2016:643-646 or as taught by Wang et al., "*Vessel extraction in coronary X-ray Angiography*", Conf Proc IEEE Eng Med Biol Soc. 2005; 2: 1584-1587.

Along with the $N_{after-contrast}$ ECG signals or the extracted cardiac cycle as a result from step 501 of FIG. 5 corresponding to the frames within $N_{after-contrast}$ are retrieved for later to allow selecting a temporal aligned roadmap to a given X-ray fluoroscopic frame during the online phase (110 of FIG. 1) and will be described in more detail at step 105 of FIG. 1. Optionally, the user identifies the vessel(s) of interest within one created roadmap or within one frame from the X-ray angiography image sequence.

Optionally, based on the generated roadmaps, quantitative image analysis can be performed to extract clinical relevant information, such as for example location and percentage of vessel obstruction, diameter and area, length of the vessel or the curvature of the vessel as for instance taught by Girasis et al., "*Advances in two-dimensional quantitative coronary angiographic assessment of bifurcation lesions: improved small lumen diameter detection and automatic reference vessel diameter derivation*", EuroIntervention 2012 March; 7(11):1326-35 or as taught by Wang et al., "*Vessel extraction in coronary X-ray Angiography*", Conf Proc IEEE Eng Med Biol Soc. 2005; 2: 1584-1587.

Figure 28:
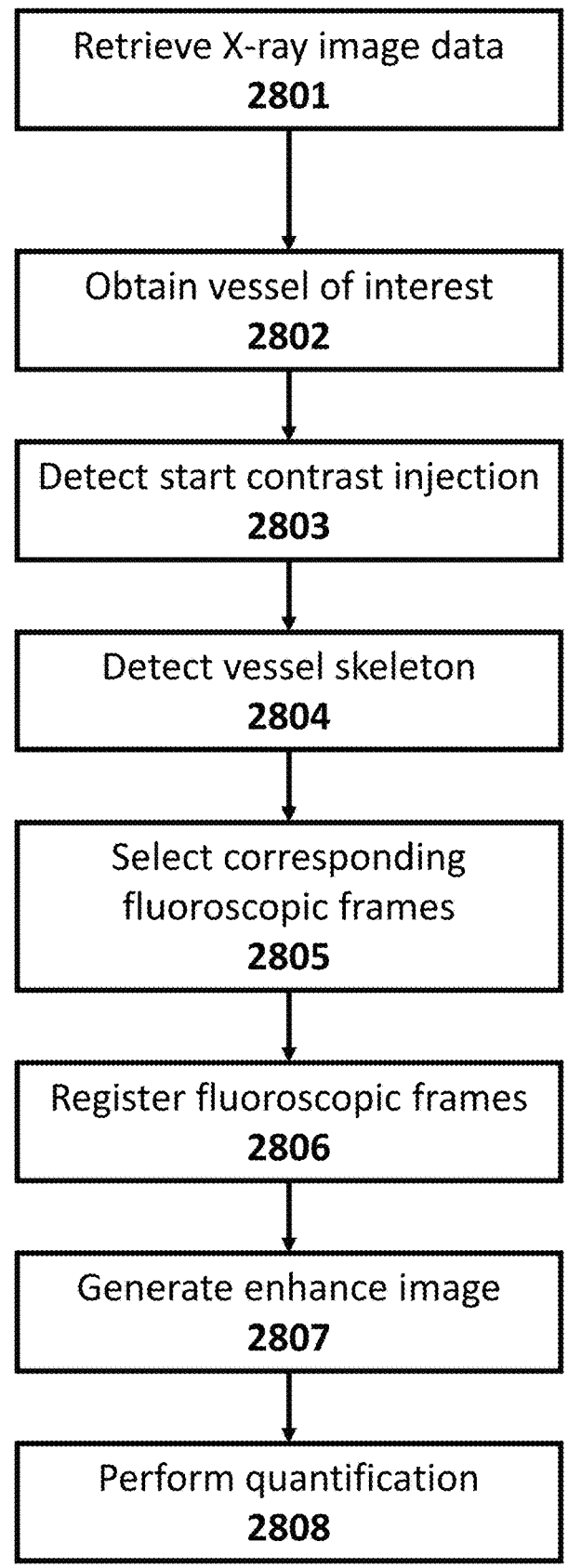
FIG. 28 shows a flow chart of a method for determining the location and amount of calcified plaque.

Optionally, the location and amount of calcified plaque can be extracted from the X-ray angiographic image sequence as for instance disclosed in detail by the flowchart description of FIG. 28 further within this application.

Figure 35:
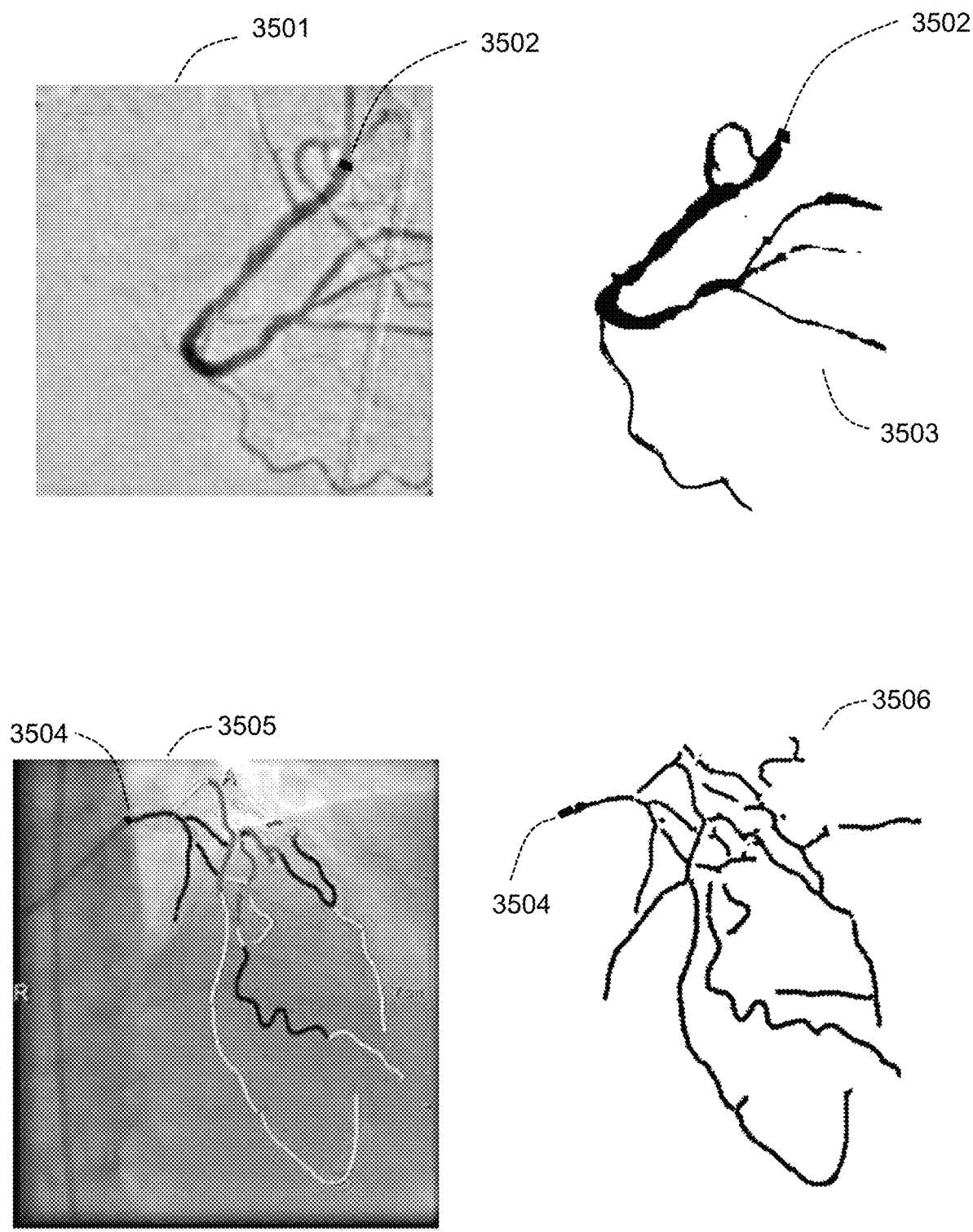
FIG. 35 shows an illustration of the integration of the device location into the roadmap.

Finally, in step 103 the obtained device location as a result of step 102 is integrated into the created roadmaps. FIG. 35 provides an illustration of the integration of the device location into the roadmap by means of examples. The first example, which represents the creation of the roadmap by means of layer separation (3501) as described before. Within 3501, the device location (3502) as a result of step 102 is integrated in the vessel layer (3501). The final roadmap, showing the vascular structures (3503) also contains the device location (3502). In the second example, which represents the creation of the roadmap by means of a skeletonization (3506, and for illustration purpose superimposed on an X-ray angiographic frame by 3505) as described before. Within 3505, the device location (3504) as a result of step 102 is shown.

Step 104: Retrieve Fluoroscopic Image Data

The first step in the online phase (110), is the retrieval of the X-ray fluoroscopic image data represented by step 104 of FIG. 1. Within a preferred embodiment the X-ray fluoroscopic image sequence is acquired real time as a live stream. Simultaneously, the ECG signal of the patient can be acquired in real time and time synchronized to the X-ray fluoroscopic image sequence. The X-ray fluoroscopic images are acquired sequentially with the same projection (view angle) as used during the offline phase (100) by step 101. Using the same projection guarantees that the object of interest and the roadmap have the same orientation as the X-ray angiographic image sequence (101), which was used to generate the roadmaps (103). FIG. 9 shows three X-ray fluoroscopic image frames (901, 902 and 904) from an X-ray fluoroscopic image sequence. The catheter is visible (904) within the X-ray fluoroscopic image frames and has been enhanced for illustration purpose. Each X-ray fluoroscopic frame is acquired within an arbitrary moment of the cardiac cycle, as illustrated by 906, 907 and 908 within an electrocardiogram (ECG) signal representing the cardiac cycle (909). The start of the cardiac cycle is for example the R-top (910) and all acquired X-ray frames (906, 907 and 908) represent a phase within the cardiac cycle (909), which is given by the time offset with respect to the start of the cardiac cycle (910) for the acquisition of the respective X-ray frame. It is preferred to acquire the ECG signal simultaneously with the acquisition of the X-ray frames. During the online phase (110), the ECG signal will be used to match the acquired frames with the corresponding roadmaps as extracted by step 103, to represent the same cardiac phase in the cardiac cycle. This is to compensate the change of vessel shape and position between X-ray fluoroscopic image frames due to cardiac motion and is further explained by step 105 of FIG. 1. Simultaneously, the device (e.g. the catheter tip location) in the acquired X-ray fluoroscopic image stream is tracked for instance by using a deep learning based Bayesian filtering method in as described further by step 106. The displacement of catheter tip between the current X-ray fluoroscopic image frame and the selected roadmap is then obtained and are applied to transform the roadmap and will be further described by step 107. Finally, the transformed roadmap is overlaid on the current X-ray fluoroscopic image frame to guide the procedure as describe by step 108.

Step 105: Select Roadmap

After retrieving fluoroscopic images including ECG signal as described by step 104, a roadmap from the selection of roadmaps (which are created in step 103) is selected for every single fluoroscopic image.

Roadmap selection represented by step 104 in FIG. 1 can be achieved by comparing the ECG signal associated with the online fluoroscopic image and the ECG of the offline angiographic sequence, such that the most suitable candidate roadmap is selected where the best match of the ECG signals is found. The selected roadmap has the same (or very similar) cardiac phase with the online X-ray fluoroscopic image, which compensates the difference of vessel shape and pose induced by cardiac motion.

To select roadmaps and images based on ECG, a temporal mapping between X-ray images and ECG signal points needs to be built first. It is assumed that ECG signals and X-ray images are well synchronized during acquisition.

In the offline phase (block 100 of FIG. 1), the beginning and the end of the image sequence are aligned with the start and end ECG signal points; the X-ray angiography frames in between are then evenly distributed on the timeline of ECG. This way, a mapping between the stored sequence images and its ECG signal can be set up: for each image, the closest ECG signal point to the location of the image on the timeline can be found; for each ECG point, an image that is closest to this point on the timeline can be similarly located. Once the mapping is available, all images with good vessel contrast filling and the ECG points that are associated to these images are selected from the X-ray angiography sequence for the pool of roadmaps. In this process, at least one heartbeat of frames should be acquired.

In addition to this, the method of step 501 can be applied to discard images prior to contrast liquid arrival in the vessel. This will speed up the process of mapping ECG data and the image sequence.

In the online phase (block 110 of FIG. 1), for acquisition of each image, a block of NECG latest ECG signal points is constantly stored. These NECG ECG signal points are considered as the ECG signal corresponding to the online fluoroscopic frame.

To compare the ECG signals associated with the offline angiographic sequence and the online fluoroscopic image, a temporal registration of the two signals using for example cross-correlation is applied, such as taught by Kim et al., "*Registration of angiographic image on real-time fluoroscopic image for image-guided percutaneous coronary intervention*", International journal of computer assisted radiology and surgery 2018:13, 203-213. The two ECG signals are first cross-correlated for every possible position on the signals, resulting in a one dimensional (1D) vector of correlation scores. The candidate frame for dynamic overlay and roadmap is then selected as the one associated with the point on the ECG of the offline angiographic sequence that is corresponding to the highest correlation score.

Step 106: Track Device

In the online phase (block 110 of FIG. 1) transformation of the object of interest or the roadmap is necessary to compensate for breathing motion or patient motion. Therefore, in step 102 a device location is obtained in the angiographic image data. Simultaneously, with the roadmap selection of step 105 in FIG. 1, the same device as is located in step 102 is tracked in the retrieved fluoroscopic images of step 106. The device could be for example be the catheter tip, pacemaker or anatomical landmarks or any other object in which its motion can be correlated to the breathing motion and possible patient motion.

Next a method for tracking a device is presented and as an example the tracked object is a catheter tip.

Exemplary Catheter Tip Tracking

The overall catheter tip tracking uses a deep learning based Bayesian filtering method and is summarized in FIG. 13. The method models the likelihood term of Bayesian filtering with a convolutional neural network, and integrates it with particle filtering in a comprehensive manner, leading to more robust tracking. In summary, for every position within an image, the new position (in new image) of the catheter tip (predict movement of catheter) can be predicted using the optical flow method (see line 6 in FIG. 13) and the addition of noise (see line 5 in FIG. 13). Further, update the weight (see line 8 in FIG. 13) by checking the likelihood of the position using the deep learning network. Next, all weights are normalized (see line 10 in FIG. 13). The real catheter tip position equals the weighted arithmetic mean of all positions and their weights. Finally, a resample of points is performed around the position with a high weight value (see line 12 in FIG. 13). Next, the tracking method is described in more detail.

Bayesian Filtering

Bayesian filtering is a state-space approach aiming at estimating the true state of a system that changes over time from a sequence of noisy measurement made on the system as for instance described by Arulampalam et al., "*A tutorial on particle filters for online nonlinear/non-Gaussian Bayesian tracking*", IEEE Transactions on signal processing 2002: 50, 174-188.

Bayesian filtering typically includes the following components: hidden system states, a state transition model, observations and an observation model. Let $x_k \in \mathbb{R}^2$ ($k=\{0, 1, 2, \ldots\}$) denote the state, the location of guiding catheter tip in the k-th frame, a 2D vector representing the coordinates in the X-ray image space. The transition of the system from one state to the next state is given by the state transition model $x_k = f_k(x_{k-1}, v_{k-1})$, where $v_{k-1} \in \mathbb{R}^2$ is an independent and identically distributed (i.i.d.) process noise, $f_k: \mathbb{R}^2 \times \mathbb{R}^2 \to \mathbb{R}^2$ is a possibly nonlinear function that maps the previous state $x_{k-1}$ to the current state $x_k$ with noise $v_{k-1}$. The observation $z_k$ in this work is defined as the k-th X-ray image of a sequence, so that $z_k \in \mathbb{R}^{w \times h}$, where w and h are the width and height of an X-ray image. We further define the observation model as $z_k = h_k(x_k, n_k)$, where $n_k \in \mathbb{R}^{n_k}$ is an i.i.d measurement noise ($n_k$ is the dimension of $n_k$), $h_k: \mathbb{R}^2 \times \mathbb{R}^{n_k} \to \mathbb{R}^{w \times h}$ is a highly non-linear function that generates the observation $z_k$ from the state $x_k$ with noise $n_k$. The state transition model $f_k$ and the observation model $h_k$, respectively, can also be equivalently represented using probabilistic forms, i.e. the state transition prior $p(x_k|x_{k-1})$ and the likelihood $p(z_k|x_k)$ from which $x_k$ and $z_k$ can be obtained by sampling.

With these definitions and $p(x_0)$, the initial belief of $x_0$, Bayesian filtering seeks an estimation of $x_k (k \geq 1)$ based on the set of all available observations $z_{0:k} = \{z_i, 0 \ldots, k\}$ up to time k via recursively computing the posterior probability $p(x_k|z_{0:k})$ as Equation 4:

$$p(x_k \mid z_{0:k}) \propto p(z_k \mid x_k) \int \frac{p(x_k \mid x_{k-1}) p(x_{k-1} \mid z_{0:k-1}) dx_{k-1}}{p(x_k \mid z_{0:k-1})} \quad \text{(Equation 4)}$$

Assuming the initial probability $p(x_0|z_0) = p(x_0)$ is known, based on Equation 4, Bayesian filtering runs in cycles of two steps: prediction and update. In the prediction step, the prior probability $p(x_k|z_{0:k-1})$, the initial belief of $x_k$ given previous observations, is estimated by computing the integral in Equation 4. In the update step, the prior probability is corrected by the current likelihood $p(z_k|x_k)$ to obtain the posterior $p(x_k|z_{0:k})$.

A Deep Learning Based Likelihood

Directly modelling the likelihood $p(z_k|x_k)$ is challenging due to (1) the complexity of the generation process $h_k$ and (2) the computational complexity of $p(z_k|x_k)$ for every value $x_k \in \mathbb{R}$. The problem is simplified by only computing the likelihood $p(z_k|x_k)$ in the image pixel space, i.e. the integer pixel coordinate. For a subpixel $x_{k_1}$ the value of $p(z_k|x_k)$ can possibly be approximated by interpolation. To this end, a deep neural network D is used to approximate $p(z_k|x_k)$ for integer pixel locations. The network takes an image $z_k$ as input and outputs a probability of observing the input $z_k$ for every pixel location $x_k$. Therefore, the approximated likelihood is a function of $x_k$, denoted as $D_{z_k}(x_k)$. Since $x_k$ is defined within the scope of the image pixel space, $D_{z_k}(x_k)$ is essentially a probability map having the same dimension and size with the input image $z_k$, in which the entry at each location $x_k^j = (j=1, 2, \ldots, wh)$ in the map represents the probability of observing $z_k$ given $x_k^j$. It is worth mentioning that the deep neural network is used for approximation of $p(z_k|x_k)$, which should be clearly distinguished from the generation model $h_k$ that maps an $x_k$ to $z_k$.

To obtain the training labels, we assume that there exists a mapping $h_k$, such that the training label can be defined as a distance-based probability map, i.e. the farther away $x_k$ is from the ground truth tip location in the image $z_k$, the less possible it is to observe $z_k$ given $x_k$ through the process $h_k$. This definition matches the intuition that from a location $x_k$ that is far from the ground truth tip location, the probability of observing a $z_k$ with the catheter tip being located at the ground truth position should be low. For simplicity, a 2D Gaussian probability density function (PDF) $N(x_k; x'_k, \sigma^2 I)$ centered at the ground truth tip location $x'_k$ with variance $\sigma^2 I$ in the image space is used as the label to train the network (1103, FIG. 11). Note that this training label makes the estimation of $p(z_k|x_k)$ equivalent to a catheter tip detection problem such that the deep neural network learns features of catheter tip and outputs high probability at locations where the features are present. Due to this reason, $p(z_k|x_k)$ is called "detection output" or "detection probability" and call the estimation of $p(z_k|x_k)$ "catheter tip detection".

The network that is used follows an encoder-decoder architecture with skip connections similar to a U-net as for instance described by Ronneberger et al., "*U-net: Convolutional networks for biomedical image segmentation*", International Conference on Medical image computing and computer-assisted intervention 2015, Springer. pp. 234-241. Additionally, similar to the work by Milletari et al., "*V-net: Fully convolutional neural networks for volumetric medical image segmentation*", 2016 Fourth International Conference on 3D Vision (3DV), IEEE. pp. 565-571, residual blocks are adopted at each resolution level in the encoder and decoder to ease gradient propagation in a deep network. Residual blocks are basically a special case of highway networks without any gates in their skip connections. Essentially, residual blocks allows the flow of memory (or information) from initial layers to last layers as for instance described by He et al., "*Deep residual learning for image recognition*", 2016 Proceedings of the IEEE conference on computer vision and pattern recognition, pp. 770-778.

Figure 12:
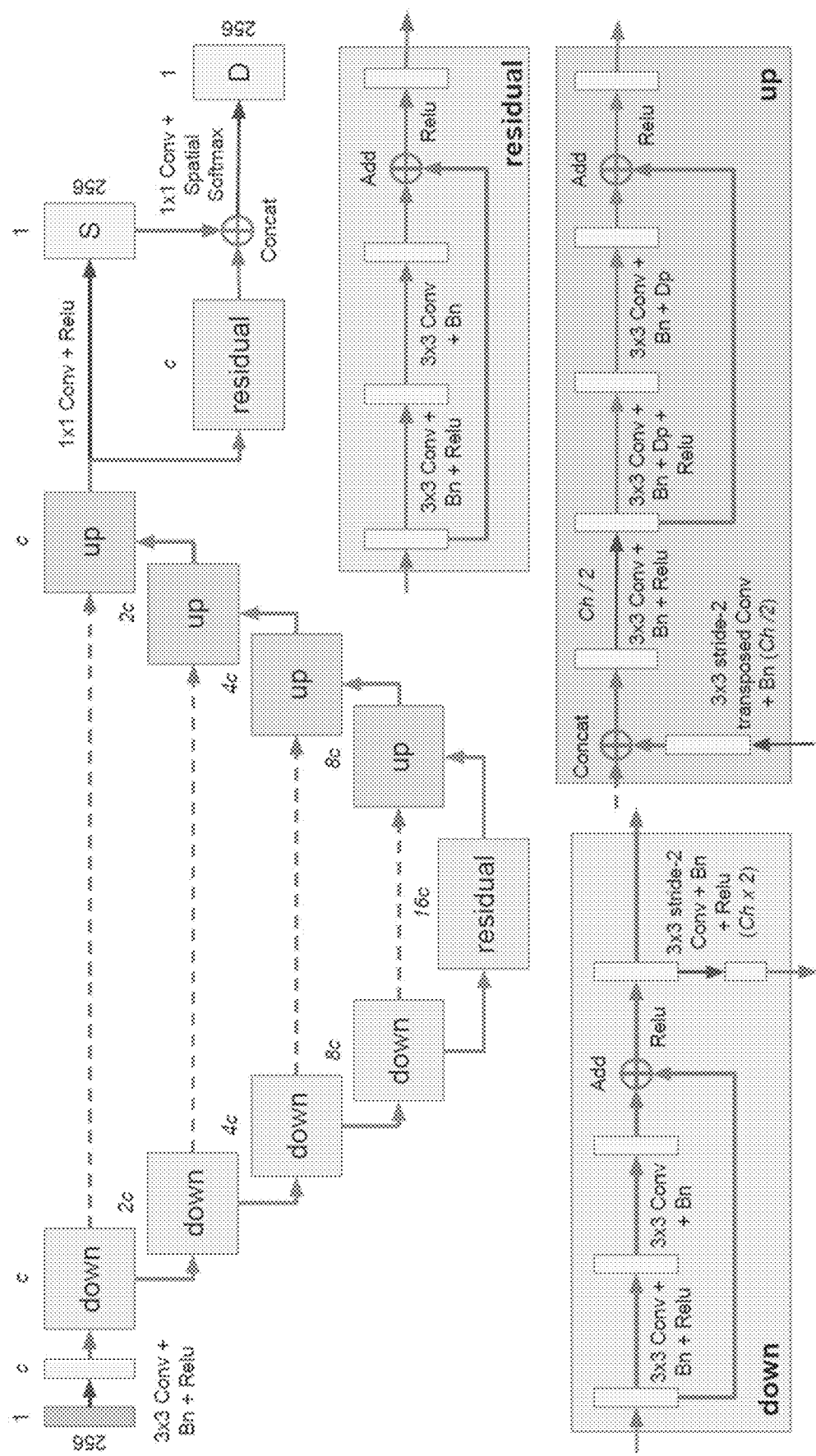
FIG. 12 shows a joint segmentation and detection network for the catheter tip detection.

The encoder consists of 4 down blocks in which a residual block followed by a stride-2 convolution is used for extraction and down-scaling of feature maps. The number of feature maps is doubled in each downsampling step. The decoder has 4 up blocks where a transposed convolution of stride-2 is used for upsampling of the input feature maps. Dropout is used in the residual unit of the up block for regularization of the network. Between the encoder and the decoder, another residual block is used to process the feature maps extracted by the encoder. The detailed network architecture is shown in FIG. 12. FIG. 12 shows a joint segmentation and detection network for the catheter tip detection and shows an example network with 4 levels of depth (the number of down or up blocks). Meaning of abbreviations within FIG. 12: Cony, 2D convolution; Bn, batch normalization; Relu, ReLU activation; Dp, dropout; Concat, concatenation; Ch, number of channels; S, segmentation output; D, detection output. Within FIG. 12, the number above an image or feature maps indicates the number of channels; the number of channels in the residual network in a block is shown above the block; c is the basic number of channels, the channel number in the first down block. The number next to a rectangle denotes the size of the image or feature maps. Red arrows indicate a change of number of channels.

Due to similar appearance between a guiding catheter tip and corners of a background structure, such as vertebral bones, lung tissue, stitches or guidewires, ambiguity may exist when the network is expected to output only one blob in the probability map. To alleviate the issue, a similar strategy is adopted as taught by Laina et al., "*Concurrent segmentation and localization for tracking of surgical instruments*", 2017 International conference on medical image computing and computer-assisted intervention, Springer. pp. 664-672, using a catheter mask (1102, FIG. 11) as an additional label to jointly train the network to output both the catheter segmentation heatmap and the likelihood probability map. The segmentation heatmap is obtained by applying a 1×1 convolution with rectified linear units (ReLU) activation on the feature maps of the last up block. To compute the likelihood probability map, a residual block is firstly applied on the feature maps of the last up block. The output feature maps are then concatenated with the segmentation heatmap as one additional channel, followed by a 1×1 convolution. Finally, to ensure the network detection output fits the definition of a probability map on image locations, following the 1×1 convolution, a spatial softmax layer is computed as Equation 5:

$$D_{k,l} = \frac{e^{A_{k,l}}}{\Sigma_{i,j} e^{A_{i,j}}}, \quad \text{(Equation 5)}$$

where A is the output feature map of the 1×1 convolution, $A_{i,j}$ denotes the value of A at location (i, j), D is the final output of the detection network, a 2D probability map representing $p(z_k|x_k)$. The details are shown in FIG. 12.

The training loss is defined as a combination of the segmentation loss and the detection loss. The segmentation loss Ls in this work is a Dice loss defined by Equation 6:

$$L_s = 1 - \frac{2\Sigma_{i,j} M_{i,j} S_{i,j}}{\Sigma_{i,j} M_{i,j}^2 + \Sigma_{i,j} S_{i,j}^2} \quad \text{(Equation 6)}$$

where M denotes the ground truth binary catheter masks, S is the segmentation heatmap. The loss function for detection Ld is mean square error given by Equation 7:

$$L_d = \frac{1}{w \times h} \Sigma_{i \leq w, j \leq h} |T_{i,j} - D_{i,j}|^2 \quad \text{(Equation 7)}$$

where T denotes the ground truth PDF, w and h are the width and height of an image. The total training loss L is defined as Equation 8:

$$L = L_s + \lambda L_d \quad \text{(Equation 8)}$$

where λ is a weight to balance $L_s$ and $L_d$.

Approximation of the Posterior with Particle Filter

Once the deep neural network is trained, its weights are fixed during inference for computing the posterior $p(x_k|z_{0:k})$ for new data. Ideally, the network detection output $p(z_k|x_k)$ should be a Gaussian PDF during inference, as it is trained with labels of Gaussian PDFs. However, due to similar appearance of background structures or contrast residual, the detection output is unlikely to be a perfect Gaussian (possibly non-Gaussian or having multiple modes), which prevents the posterior $p(x_k|z_{0:k})$ in Equation 4 being solved with an analytical method. In practice, the posterior can be approximated using a particle filter method as for instance described by Arulampalam et al., "*A tutorial on particle filters for online nonlinear/non-Gaussian Bayesian tracking*", IEEE Transactions on signal processing 2002:50, 174-188.

Particle filter methods approximate the posterior PDF by a set of Ns random samples with associated weights $\{x_k^i, w_k^i\}_{i=1}^{N_s}$. As $N_s$ becomes very large, this discrete representation approaches the true posterior and the approximation of the posterior $p(x_k|z_{0:k})$ is given by Equation 9:

$$P(x_k|z_{0:k}) \approx \Sigma_{i=1}^{N_s} w_k^i \delta(x_k - x_k^i) \quad \text{(Equation 9)}$$

where δ(•) is the Dirac delta function. The weight $w_k^i$ can be computed in a recursive manner as Equation 10 once $w_{k-1}^i$ is known:

$$w_k^i \propto w_{k-1}^i \frac{p(z_k|x_k^i) p(x_k^i|x_{k-1}^i)}{q(x_k^i|x_{k-1}^i, z_k)} \quad \text{(Equation 10)}$$

where $q(x_k|x_{k-1}^i, z_k)$ is an importance density from which it should be possible to sample $x_k^i$ easily. For simplicity, a good and convenient choice of the importance density is the prior $p(x_k|x_{k-1}^i)$, so that the weight update rule (Equation 10) becomes $w_k^i \in w_{k-1}^i p(z_k|x_{k-1})$.

A sample can be drawn from $p(z_k|x_{k-1}^i)$ in the following way. First, a process noise sample $v_{k-1}^i$ is sampled from $p_v(v_{k-1})$, the PDF of $v_{k-1}$; then $x_k^i$ is generated from $x_{k-1}^i$ via the state transition model $x_k^i = f_k(x_{k-1}^i, v_{k-1}^i)$. Where, $p_v(v_{k-1})$ is set to be a Gaussian $N(0, \sigma_v^2 I)$. The choice of motion model for $f_k$ is important for an accurate representation of the true state transition prior $p(x_k|x_{k-1})$. A random motion cannot characterize well the motion of catheter tip in X-ray image frames. In this application, the motion is estimated from adjacent frames using an optical flow method, as this approach 1) takes into account of the observation $z_k$, which results in a better guess of the catheter tip motion, and 2) enables estimation of a dense motion field where the motion of a sample $x_k^i$ can be efficiently obtained. Therefore, $f_k$ is defined as Equation 11:

$$x_k = x_{k-1} + u_{k-1}(x_{k-1}) + v_{k-1} \quad \text{(Equation 11)}$$

where $u_{k-1}(\bullet)$ is the motion from frame k−1 to frame k estimated with optical flow using the method as described as for instance by Farneback et al., "*Two-frame motion estimation based on polynomial expansion*", Scandinavian conference on Image analysis 2003, Springer. pp. 363-370, $u_{k-1}(x_{k-1}))$ is the motion from state $x_{k-1}$.

Once samples are drawn and their weights are updated, the so-called "resampling" of the samples should be performed to prevent the degeneracy problem, where all but one sample will have negligible weight after a few iterations. The resampling step resamples the existing samples according to their updated weights and then resets all sample weights to be $1/N_s$, so the number of effective samples which have actual contribution to approximate $p(x_k|z_{0:k})$ is maximized. If the resampling is applied at every time step, the particle filter becomes a sampling importance resampling (SIR) filter, and the weight update rule follows Equation 12.

$$w_k^i \propto p(z_k|x_k^i) \quad \text{(Equation 12)}$$

The final decision on catheter tip location in frame k can then be computed as the expectation of $x_k, \hat{x}_k = \int x_k \, p(x_k|z_{0:k}) \, dx_k$, which is in this case, the weighted sum of all samples:

$$\hat{x}_k = \sum_{i=1}^{N_s} w_k^i x_k^i. \quad \text{(Equation 13)}$$

Figure 14:
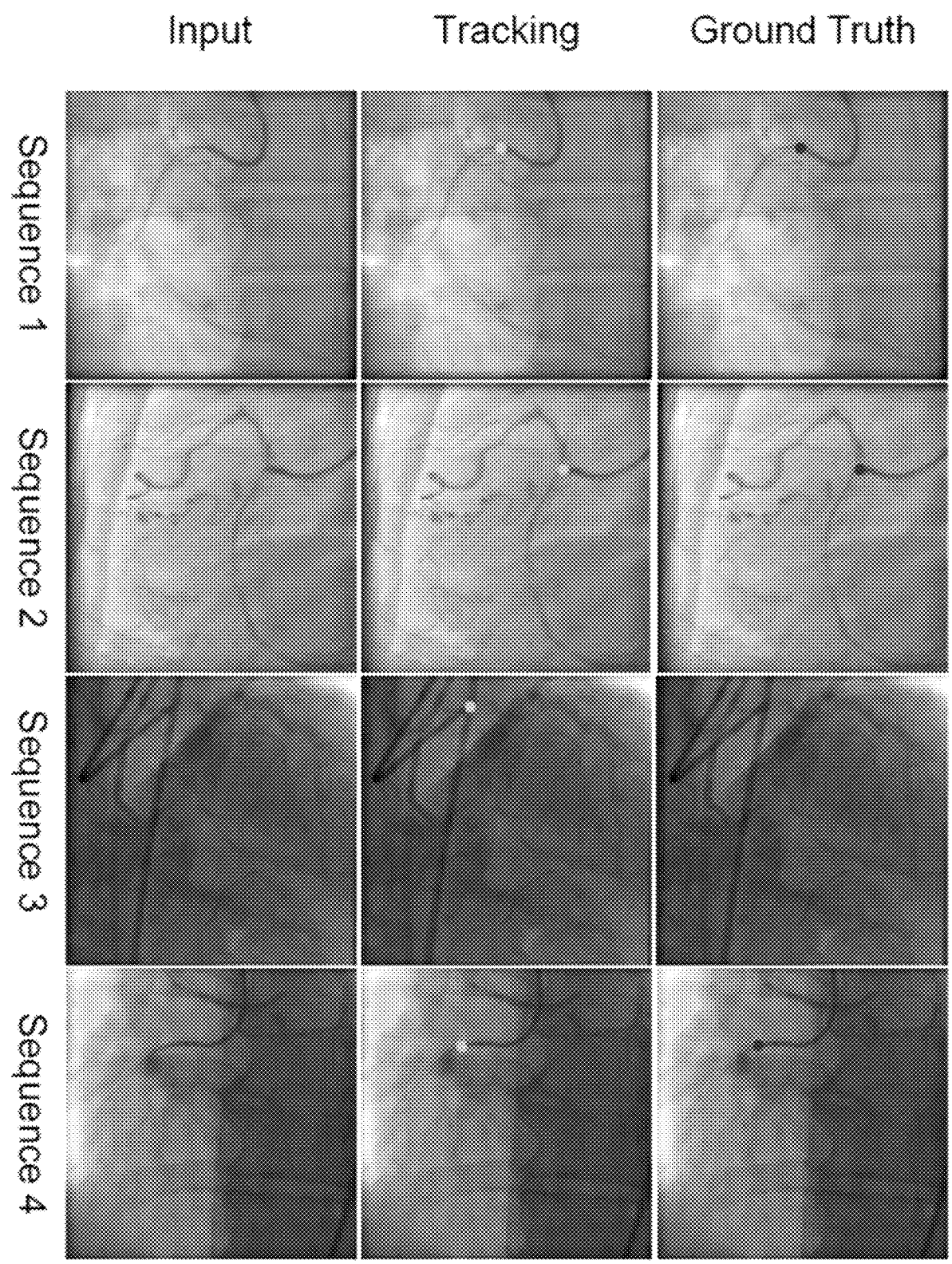
FIG. 14 shows four examples of the deep learning based Bayesian filtering catheter tip tracking method.

FIG. 14 presents four examples (Sequence 1 to 4) of the described catheter tracking method. In the first column, an online fluoroscopic image is shown, in the second column the catheter tip location resulting from the tracking method as described above is presented as a dot. In the last column on the right the catheter tip ground truth is presented.

The final catheter tip location as obtained from the tracking method is used in the next step 107 to determine the translation between the device location in the online fluoroscopic image and corresponding offline angiographic image of the selected roadmap.

In alternate embodiments, step 106 can be accomplished by the teachings of U.S. Pat. No. 9,256,936 "Method and apparatus for tracking objects in a target area of a moving organ". U.S. Pat. No. 9,256,936 employs the property of synchronized periodic motion to establish the dynamic geometric relationship between the positions of the tracked features. This is realized by learning the periodic motion of the individual features, such as from other visible devices generally present in the image view during percutaneous coronary interventions procedures. When one of the features is obscured, knowledge about the periodic motion patterns of both features, the position of one of the features, and the phase of the periodic motion can be used to derive the position of the obscured feature. If the first feature is the device target location itself (for instance the catheter tip), such location is immediately determined. If the first feature is not the target location, but a feature that experiences the same motion as the target location (for instance another visible devices), the position of the device target location can be derived from the position of the first feature, by using the fact that the first feature experiences the same motion as the target area. This requires knowledge about the geometric relation between the first feature and the target area.

Step 107: Transform Selected Roadmap to Generate Dynamic Roadmap

As described herein, a reference point can be used to compensate for motion between the roadmaps obtained from the X-ray angiographic image sequence (offline phase) with the X-ray fluoroscopic image stream (online phase). The reference point, which can be extracted from the device location, can be any object in which its motion can be correlated to the breathing motion and patient motion and the device can be for example the catheter tip, pacemaker or an anatomical landmarks. Within a preferred embodiment the device is a guiding catheter and the device location is the guiding catheter tip. Within step 107, the location of the device (e.g. catheter tip) in current X-ray fluoroscopic frame, as a result of step 106, and the device location (e.g. catheter tip) from the selected roadmap frame as a result of step 105 is used to obtain a transformation function to align the selected roadmap with the current X-ray fluoroscopic image frame. In embodiments, this transformation function might be a rigid transformation based on the displacement obtained from the catheter tip between the current frame and the catheter tip within the selected roadmap frame. Alternatively, the transformation function can be a non-rigid transformation.

For example, a rigid transformation of the roadmap can be performed by using a rigid transformation function. Considering the original roadmap as function $R(x,y)$ (as a result of step 105) and a transformation function T, then the transformation function can be as follows:

$$F(x,y) = T\{R(x,y)\} \quad \text{(equation 14)}$$

where $F(x,y)$ is the transformed roadmap. The transformation function T can be, for example, a displacement function, rotation function, scaling function, etc. For instance, when the roadmap represents the vessel model as centerlines, or contours, the above transformation can be applied to each two dimensional coordinate (x,y) of the centerlines or contours. In the case where the roadmap represents the vessel model as an image mask, the above transformation can be performed on the pixels of the image mask.

Step 108: Overlay Dynamic Roadmap on Fluoroscopic Image Data

The dynamic roadmap that results from the cardiac matching and transformation of the roadmap is rendered and integrated as an overlay on the corresponding X-ray fluoroscopic or angiographic image data frame of the live angiographic image data image data stream of the patient.

Examples of a dynamic roadmap overlaid on a non-contrast image are presented in FIG. 10a and FIG. 10b. Within FIG. 10a an example is shown of the dynamic roadmapping, in which the picture on the left shows the extraction of the coronary tree, and the picture on the right the coronary tree superimposed on a single frame within an X-ray fluoroscopic image sequence, were the dynamic motion such as breathing motion, patient motion and cardiac motion are corrected.

FIG. 10b shows another example, in which the picture on the left shows a single frame within an X-ray fluoroscopic image sequence and the picture on the right the same fluoroscopic X-ray image with dynamic roadmap superimposed in which dynamic motion such as breathing motion, patient motion and cardiac motion are corrected.

The method provides a real time dynamic overlay or roadmapping where a visual representation of the dynamic roadmap is rendered and superimposed on the live X-ray fluoroscopic or angiographic image stream/sequence and thereby providing support for the clinician in improved patient treatment.

Figure 34A:
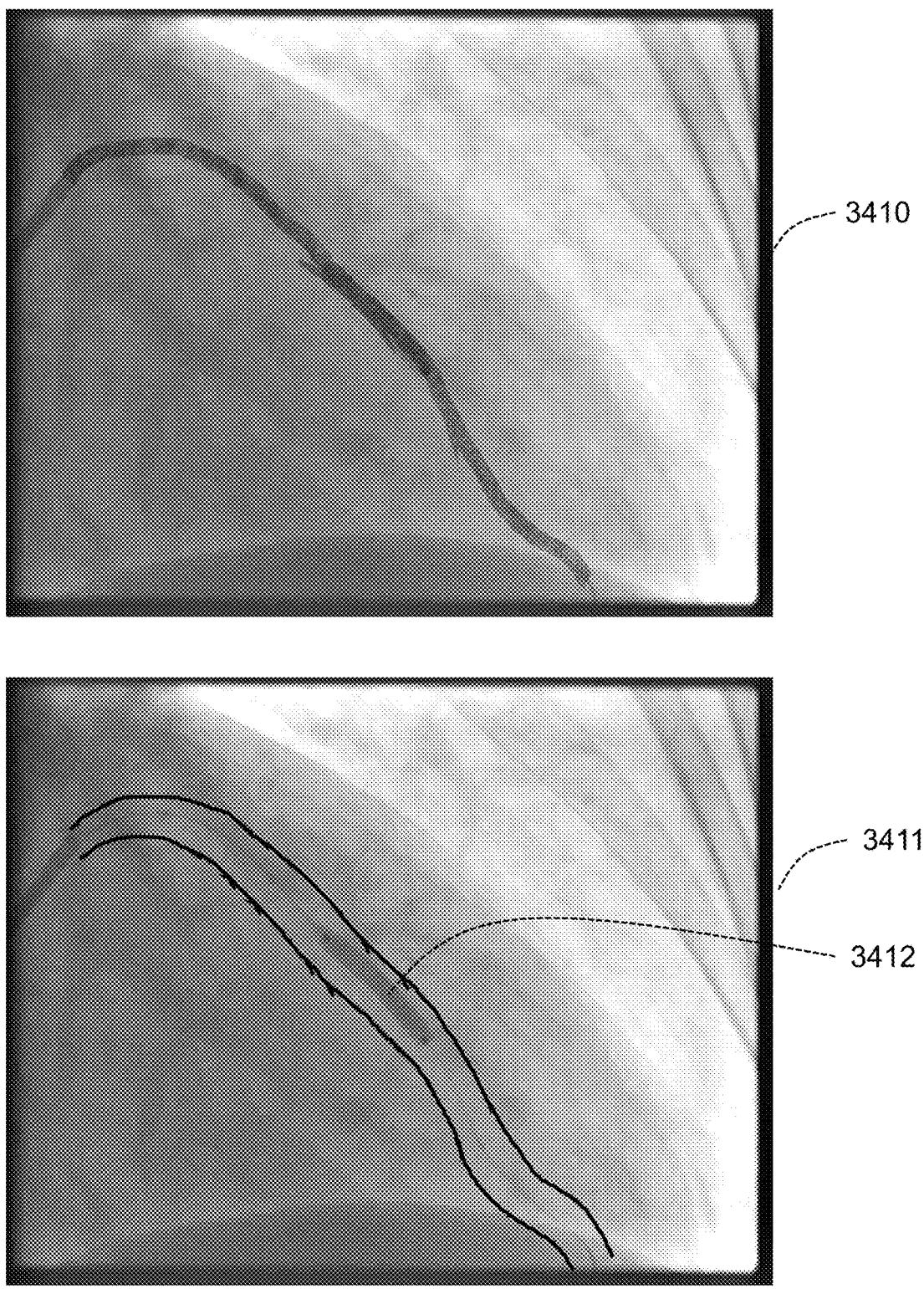
FIG. 34a shows some example of superimposing of the roadmap on X-ray fluoroscopic image data.

In embodiments, step 108 can be accomplished by rendering the transformed roadmap (dynamic roadmap) that results from step 103 according to the viewpoint of the current live image in the live image stream/sequence of the patient. The pixels of the rendering of the dynamic roadmap that correspond to the organ of interest (e.g., the coronary tree) can be assigned color values in a predefined range, such as a range of color values from red to white. Besides coloring the dynamic roadmap, also transparency of the rendered model can be applied. Transparency of the model provides a dual view, where the X-ray fluoroscopy image is visible as well as the dynamic roadmap. To allow visual appreciation of stents, balloons, or other devices or instruments to treat the diseased artery and allow visual appreciation of the projected overlay, the overlay may be projected on the X-ray fluoroscopic image data in transparent mode as illustrated by 3410 in FIG. 34a. The amount of transparency can obviously be adjusted. Within FIG. 34a, 3411 provides another example in which the overlay is projected without obscuring any treatment instrument used to treat a diseased artery and, in the example, the treatment instrument is a balloon (3412). This is accomplished by only showing the outer borders of the roadmap image, which may be generated by first dilating the roadmap by a predefined amount followed by extracting the boundaries of the dilated roadmap. Obviously, this can also be in transparent mode, in which the amount of transparency can be adjusted.

The mapping of the model (vessel layer image of FIG. 10a) to the dynamic roadmap overlay can be performed by translating the pixel intensities to color values (for instance from red to white, see example FIG. 10a); where white represents dark pixel intensity of the vessel (FIG. 10a, right image) and red represents light dark intensities of the vessel (FIG. 10a, right image).

The color scheme can also represent quantitative parameters. For instance geometrical parameters such as the local curvature of the vessel or the local diameter. These geometrical parameters can be derived for example from the vessel model created in step 103. Another example of quantitative parameters are pathological parameters such as the amount of calcified plaque in the lumen which is derived in step 103 and in more detail by the flowchart description of FIG. 28. After step 108, the method continues with step 104 to process the next X-ray fluoroscopic image frame and in case the retrieval of the X-ray fluoroscopic image data stops, as described by step 104, the flowchart as described by FIG. 1 ends.

Experimental Setup of the Dynamic Coronary Roadmapping

Within this section an example is provided to train the device tracking method as described by step 106 of FIG. 1, which includes training of the deep neural catheter detection network as described by FIG. 12 and tuning of the deep learning based Bayesian filtering tracking method as described by the algorithm of FIG. 13. Furthermore, some experiments are described using the dynamic coronary roadmapping workflow as described by the flowchart of FIG. 1. Four datasets are used, which include:

1. Training data set for catheter tip detection. This dataset consist of an amount of X-ray fluoroscopic image sequence, and further reference as $N_{training}$. This dataset is used to train the deep neural network as described by FIG. 12.
2. Validation data set for catheter tip detection. This dataset consist of an amount of X-ray fluoroscopic image sequence, and further reference as $N_{validation}$. This dataset is used to validate the deep neural network as described by FIG. 12.
3. Training data set for catheter tip tracking. This dataset is used to tune the parameters for the deep learning based Bayesian filtering tracking method as described by the algorithm of FIG. 13. This dataset consist of an amount of X-ray fluoroscopic image sequence, and further reference as $N_{tune}$.
4. Validation data set for catheter tip tracking. This dataset is used to evaluate the tuned deep learning based Bayesian filtering tracking method as described by the algorithm of FIG. 13. This dataset consist of an amount of X-ray fluoroscopic image sequence, and further reference as $N_{evaluate}$.

As images may be acquired with different X-ray systems and different X-ray imaging protocols, the image dimension (number of rows and number of columns) and the pixel depth (range of pixel intensities) might vary. Therefore, all images within the datasets are resampled to a grid p×p and its intensities are scaled to a range 0 to l. Typically, p is 256 and l is 1.0.

All conducted experiments in this section are outlined as follows. First a description of training the deep neural network to obtain the optimal detection is described. Next, the training (tune particle filter) of the catheter tip tracking is described. Finally, the evaluation of the trained catheter tracking is described.

Training the Deep Neural Network

Figure 11:
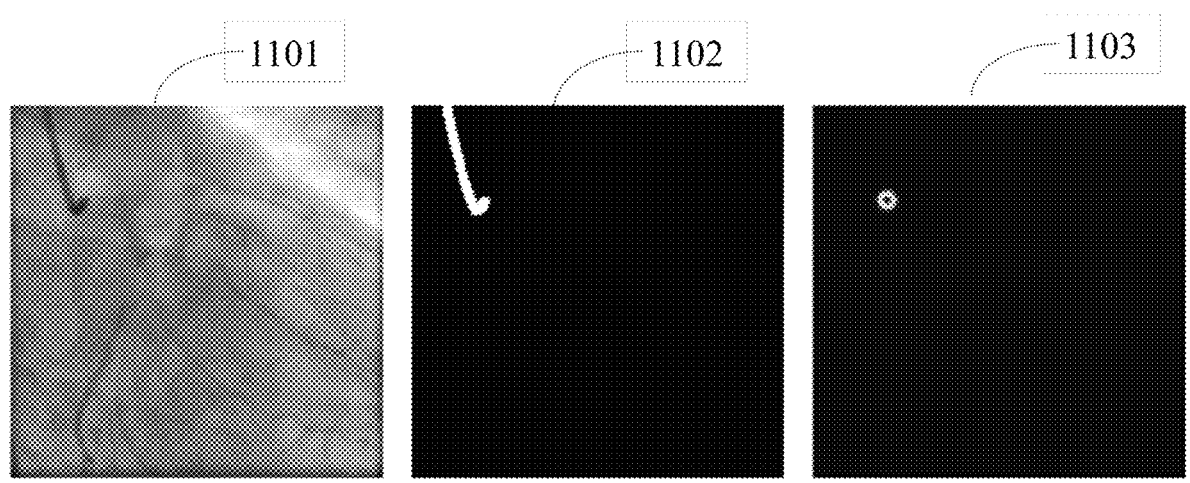
FIG. 11 shows an example of labels used to train the deep learning network.

In order to train the deep neural network to provide accurate likelihood probability map the datasets $N_{training}$ and $N_{training}$ are used. Both datasets includes labels identifying the object of interest in the datasets to be trained. FIG. 11 provides an example of the labels as used within the training of the deep neural network. Within FIG. 11, 1101 shows an example of an X-ray fluoroscopic image frame, and 1102 the binary catheter mask for catheter segmentation and 1103 the 2D Gaussian PDF for likelihood estimation for catheter tip location. The standard deviation σ of the Gaussian PDF for the training label 1103 of the detection network is set to the amount of pixels related to the dimension of the datasets, and this amount should correspond to the estimation of the maximal possible catheter tip radius in pixels. Typically, in case the dimensions of the datasets is 256×256, σ is set to 4 pixels.

Data augmentation is performed to increase the number of training samples and their diversity. The augmentation includes geometric transformation such as flipping (left-right, up-down), rotation of multiple of 90 degrees, random affine transformation (such as translation, scaling, rotation, shear), and random elastic deformation. To make the trained model robust to noise, in addition to the geometric transformations also data augmented can be performed by adding Gaussian noise to the pixel values.

During training, the λ value in the training loss (equation 8) is typically set to 10 to make the scale of the two terms similar ($L_s$ and $L_d$ of equation 8). Adam optimizer (Kingsma et al., "*Adam: A Method for Stochastic Optimization*", International Conference on Learning Representations, ICLR 2015) was used to minimize the loss function with a learning rate of typically 0.0001. The number of training samples in a batch is typically 4 and the network is trained with typically 100 epochs to ensure convergence.

Training the deep neural network to output reasonable likelihood probability map is performed by tuning the network hyperparameters. To select hyperparameters and model weights in training, an evaluation metric is required. As the deep network is essentially a catheter tip detector, accurate detection of the tip location is desired. For example, the mean Euclidean distance between the ground truth and the predicted tip location averaged over all validation frames, can be used as the validation criteria for selecting the optimal training epoch and the network hyperparameters.

Training the Catheter Tip Tracking

The catheter tip is tracked in X-ray fluoroscopy images using algorithm as described by FIG. 12 based on a trained network with the optimal hyperparameter setting from previous section 'Training the deep neural network'. The parameters of the optical flow method as used in the algorithm described by FIG. 12 and particle filtering (section 'Approximation of the Posterior with Particle Filter' within description of step 107 of FIG. 1) are tuned on the dataset $N_{tune}$.

In case the approach of Farneback et al., "*Two-frame motion estimation based on polynomial expansion*", Scandinavian conference on Image analysis 2003, Springer. pp. 363-370, was used as optical flow method (equation 11), a grid search to find the optimal parameter setting is done on the following parameters of the Farneback method: (1) the image scale to build the pyramids, (2) the number pyramid levels, (3) the averaging window size, (4) the number of iterations, (5) the size of the pixel neighborhood used to find polynomial expansion in each pixel, and finally (6) the standard deviation of the Gaussian that is used to smooth derivatives used as a basis for the polynomial expansion. The above parameters are tuned independently of the deep neural network, as optical flow directly estimates the catheter tip motion between two frames. To tune the parameters, we tracked the tracked catheter tip in X-ray fluoroscopy starting from the ground truth tip position in the first frame using the motion field between two adjacent frames estimated with optical flow. The average and median distance between the tracked tip position and the ground truth is than used as the evaluation criteria for the tuning.

The parameters to tune for the particle filter are the number of samples Ns (See FIG. 13) and the variance of process noise a (see section 'Approximation of the Posterior with Particle Filter' within description of step 107 of FIG. 1). When tuning them, the parameters of the trained network and the optical flow method are fixed. Following the algorithm by FIG. 13, the catheter tip from the ground truth position (probability map) in the first frame is tracked, and used the mean and median distance between the tracked and the true position as the validation metric.

Evaluating the Catheter Tip Tracking

The proposed tracking method in the algorithm described by FIG. 13 uses the ground truth tip probability map of the first frame as the initial PDF p(x0) to draw samples. This method is referred to as "Tracking". In addition, three alternatives are described and investigated within this section.

The first one tracks catheter tip using only the detection network as described by section 'A Deep Learning based Likelihood' within the description of step 107 of FIG. 1, and with the chosen network architecture and trained parameters as described by the above section 'Training the catheter tip tracking', therefore, no temporal information is used. This method is referred to as "Detection (Net)".

The other two methods in this experiment use only optical flow to track catheter tip starting from the ground truth tip position in the first frame. The motion field towards the current frame, estimated by the two methods, was based on the de-formation from the previous frame or the first frame in the sequence, respectively. They are called "Optical Flow (previous)" and "Optical Flow (first)".

The tracking accuracies of all methods reported in this section were obtained on the dataset $N_{evaluate}$. The tracking results of the 4 proposed methods on example image frames from the 4 X-ray fluoroscopic sequences are illustrated in FIG. 36, in which the (blue) dots indicates the predicted catheter tip location and the (red) dots (within column Ground Truth) indicates the ground truth location (labeled).

Figure 36:
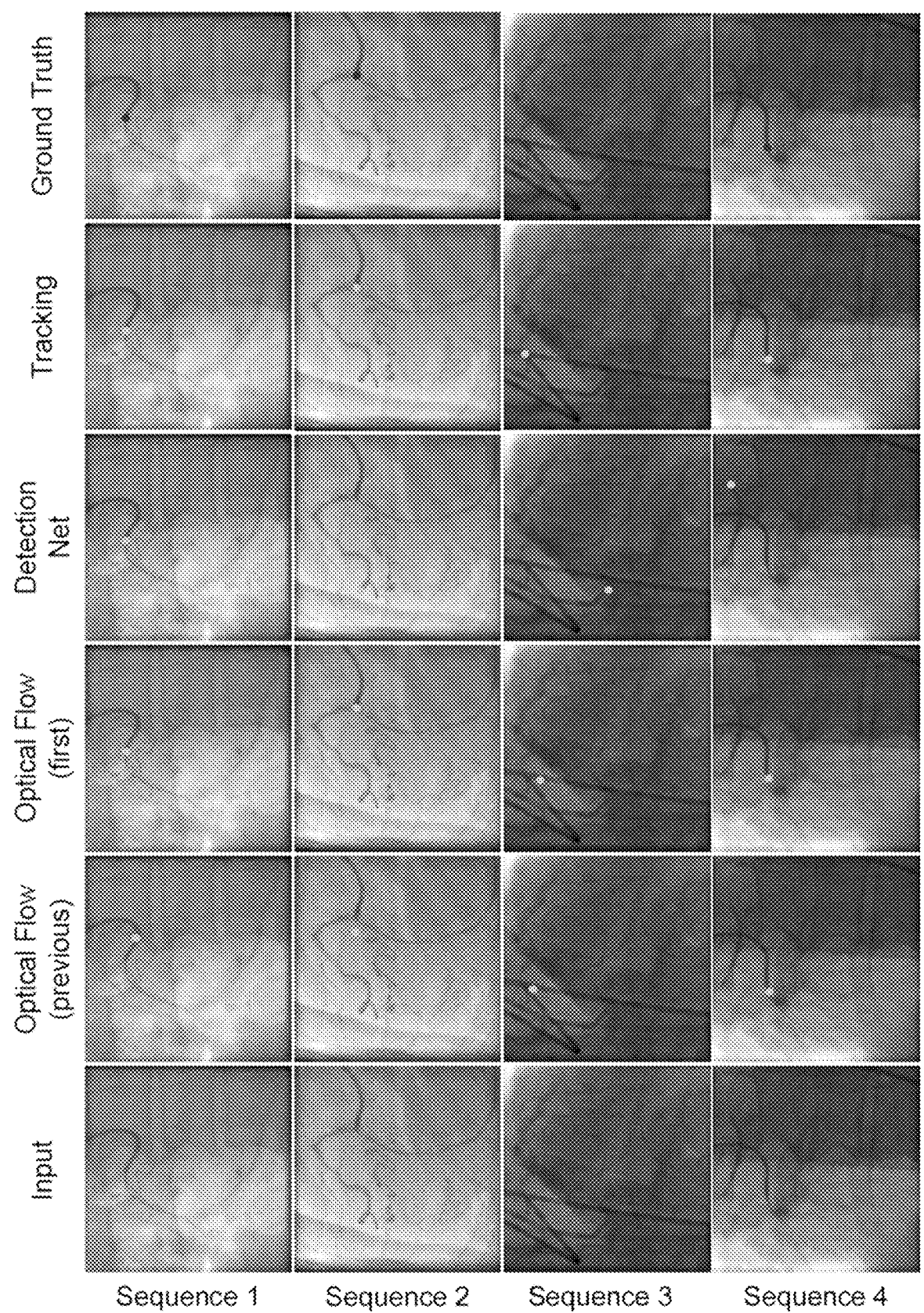
FIG. 36 shows an example of the tracking results of alternative proposed methods on example image frames.
Figure 37:
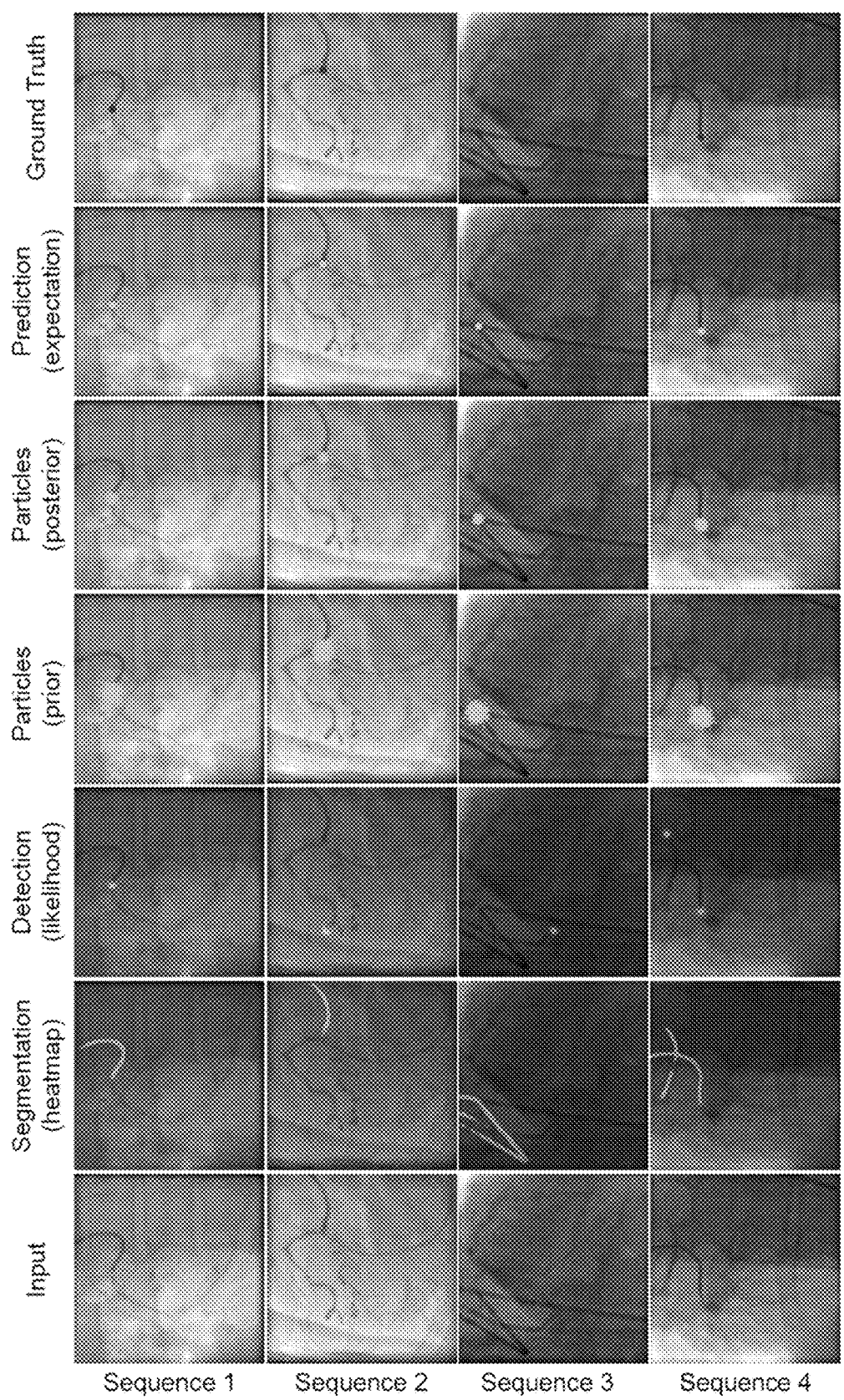
FIG. 37 shows an illustration of a proposed tracking method.

FIG. 37 illustrates how the proposed tracking method by step 107 of FIG. 1 works on the same 4 frames in FIG. 36. FIG. 37 shows the high probability as a bright color in the detection map, samples or particles are presented as green dots. The blue point indicates the predicted catheter tip location; the red point shows the ground truth location (labels). FIG. 37 also shows that the prior hypotheses (samples) assists to focus on the correct target location and results in reliable posterior estimation, especially when the detection produces ambiguity in cases of multiple catheters or contrast residual presented in images.

Figure 18:
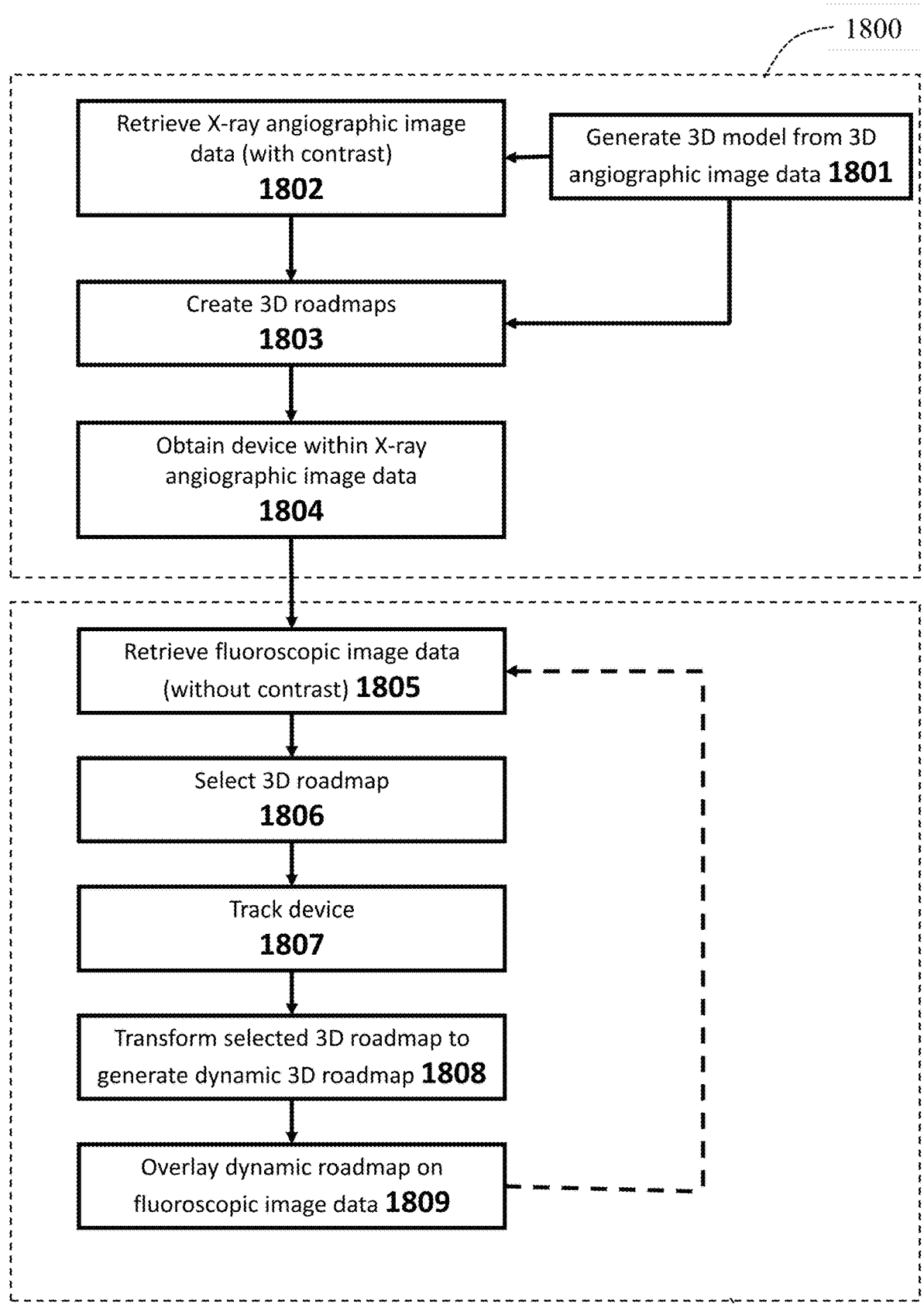
FIG. 18 shows a flow chart of a method for determining a dynamic 3D coronary roadmap.

Within an alternative embodiment, the set of roadmaps and dynamic roadmap generated by the process can be three-dimensional (3D) roadmaps as represented by the flowchart of FIG. 18. The advantage of using 3D roadmaps, resulting in a sequence of 3D roadmaps (3D+t), will be: a) the X-ray viewing angles as well as magnification and table position can be different between the offline phase (1800) and the offline phase (1810), which enables more freedom to the physician during the intervention procedure, and b) complementary information as obtained by non-invasive 3D imaging, such as plaque type, can be included in the 3D roadmap and c) advance quantitative analysis, such as computation of the coronary wall shear stress (WSS) or computation of fractional flow reserve (cFFR) either obtained from the non-invasive 3D imaging or obtained from 3D reconstruction of the vessel of interest from multiple X-ray angiographic sequence or a combination of those. In the following sections, the steps within FIG. 18 are explained in more detail.

Step 1801: Generate 3D Model from Data 3D Angiographic Image Data

First at step 1801, which is an optional step, a 3D model of (a large portion of) the coronary tree is generated. This is done using data acquired from a 3D angiographic imaging modality, for instance computed tomography (CT), X-ray rotational angiography, 3D Ultrasound, or magnetic resonance imaging (MRI). The 3D model can be for example in the form of 3D centerlines, 3D surface contours representing the luminal surface of the vessels and/or the outer vessel surface, plaque, 3D masks, or a combination of these.

The 3D centerlines can be created manually, for instance by indicating the vessel centerlines within the 3D volumetric image data, or automatically as taught for instance by Lesage et al, "*Bayesian Maximal Paths for Coronary Artery*

Segmentation from 3D CT Angiograms", MICCAI 2009, Part 1, LNCS 5761, pp 222-229.

The coronary lumen, arterial wall and detection of coronary plaque from CT angiographic image data can be for (semi) automatically detected as for instance taught by Kirissli et al. "*Standardized evaluation framework for evaluating coronary artery stenosis detection, stenosis quantification and lumen segmentation algorithms in computed tomography angiography*", Medical Image Analysis, vol. 17, no. 8, pp. 859-876, 2013, a methods are described to detect the coronary lumen, arterial wall and detection of coronary plaque from CT angiographic image data.

Coronary plaque can be detected as for instance disclosed in U.S. application Ser. No. 16/379,248 (Method and system for assessing vessel obstruction based on machine learning) or by for instance the method as taught by Dey et al., "*Automated 3-dimensional quantification of noncalcified and calcified coronary plaque from coronary CT angiography*", Cardiovasc Comput Tomogr. 2009; 3(6):372-382, or as taught by Gerretsen et al., "*Visualization of coronary wall atherosclerosis in asymptomatic subjects and patients with coronary artery disease using magnetic resonance imaging*", PLoS One. 2010 Sep. 29; 5(9), or as taught by Adame et al., "*Automatic segmentation and plaque characterization in atherosclerotic carotid artery MR images*", Magnetic Resonance Materials in Physics, Biology and Medicine 2004; 16 (5): 227-234.

FIG. 19 shows some example of the generation of the 3D model based on 3D angiographic image data. Picture 1901 shows the extracted coronary tree, both left coronary artery (LCA) as well the right coronary artery (RCA) including a part of the ascending aorta based on CT. Picture 1902 is similar to 1901, excluding the ascending aorta. Within picture 1903 a part of luminal vessel tree is visible as well as detected atherosclerotic plaque (1905) based on MRI, and 1906 shows the detected luminal border (inner vessel wall; representing the blood lumen) as well as the arterial border (outer wall) of a vessel. FIG. 25 provides two example of 3D segmentation of the coronary lumen including segmentation of coronary plaque. This can be extracted from 3D angiographic image data or by 3D coronary reconstruction based on x-ray angiography as described by step 1803 of FIG. 18 also calcified plaque can be extracted from X-ray image data as described by the flowchart of FIG. 28.

Figure 20:
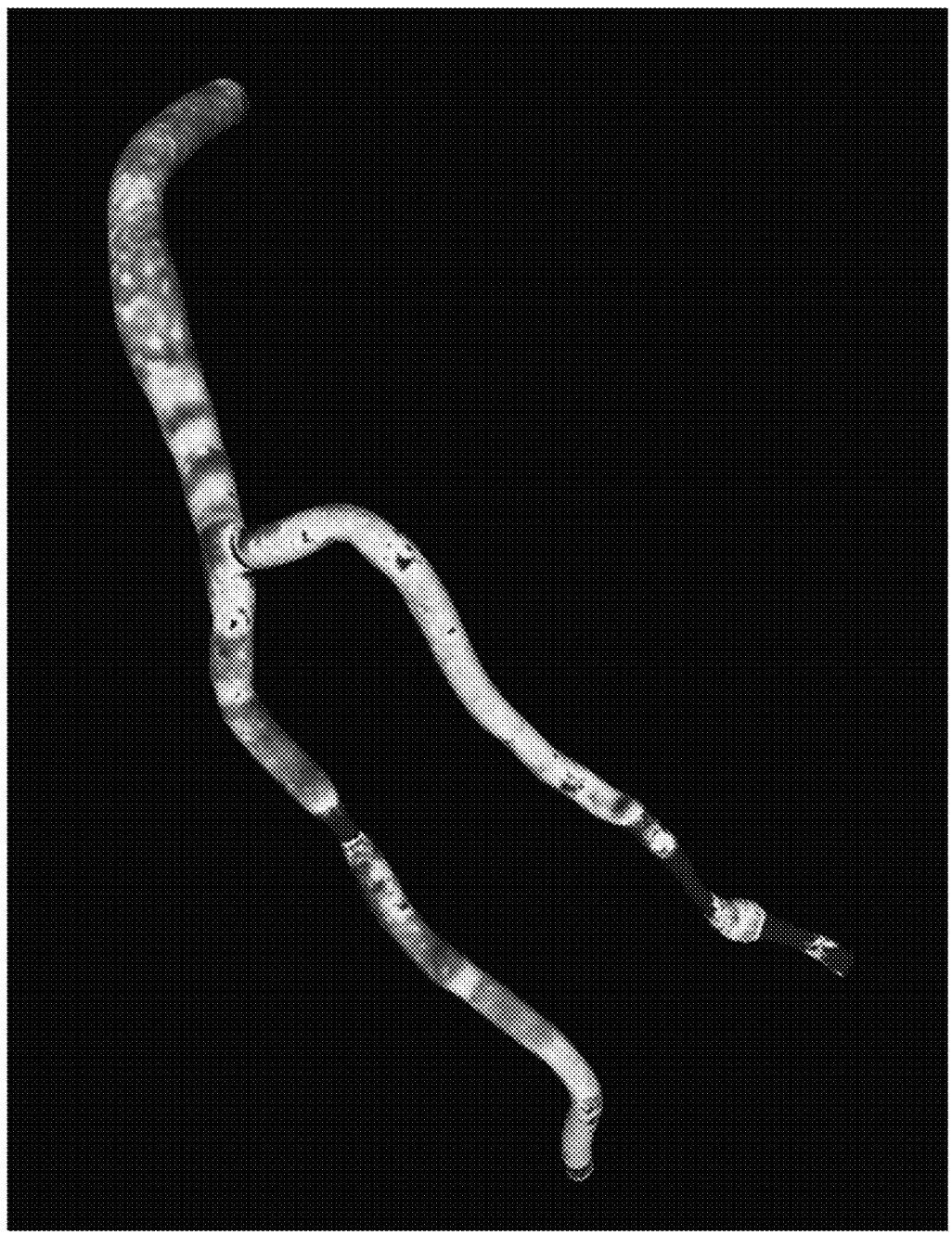
FIG. 20 shows an example of a coronary vessel in which the WSS is superimposed on the luminal surface.
Figure 21:
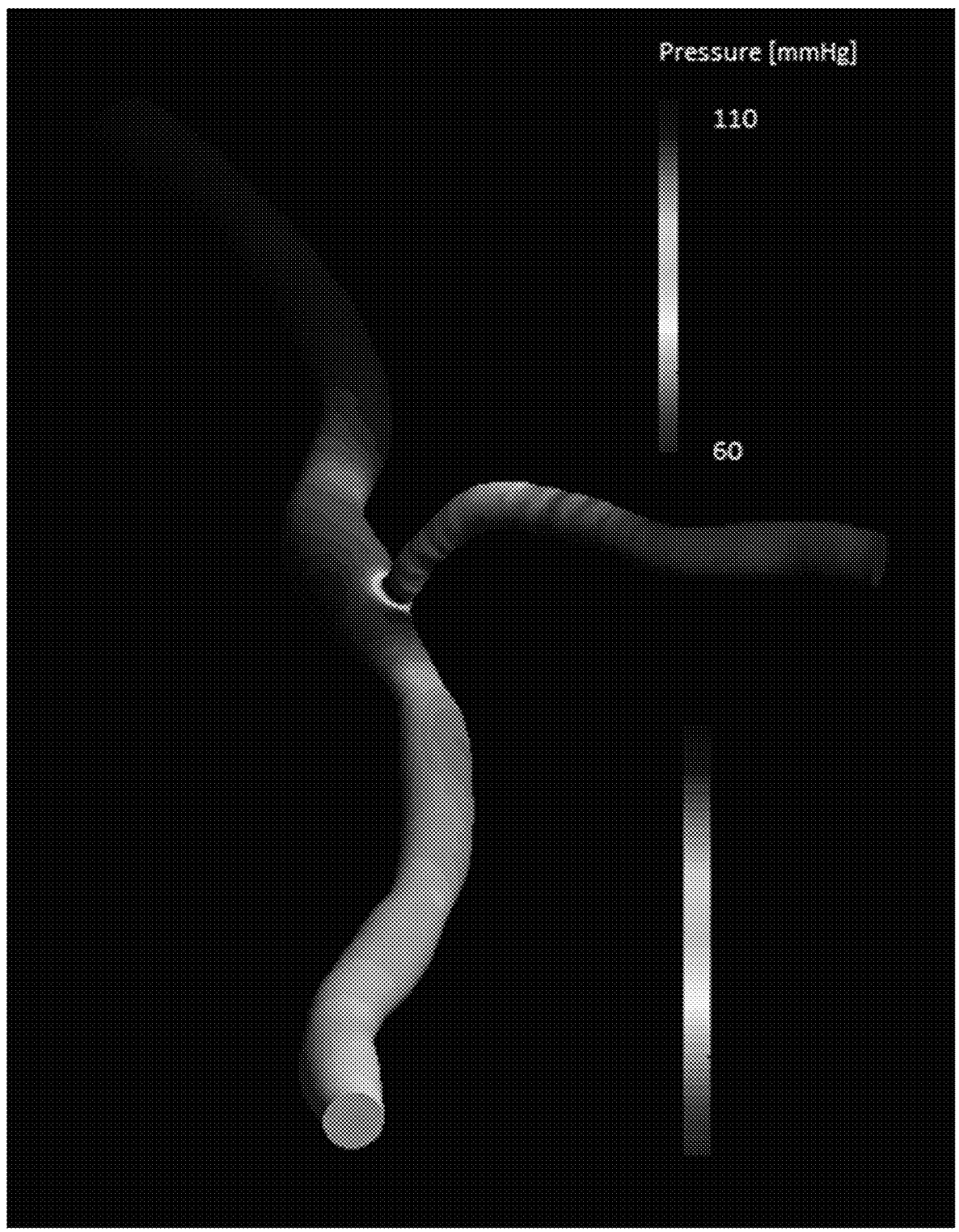
FIG. 21 shows an example of a coronary vessel in which the pressure and fractional flow reserve is superimposed on the luminal surface.

Optionally, the 3D angiographic CT image data can be used to compute the cFFR along the coronary tree as for instance disclosed by U.S. application Ser. No. 16/379,248, which discloses methods to compute the fraction flow reserve along a coronary artery. Optionally, the extracted 3D model either from CT, rotation angiography or MRI can be used to compute the coronary WSS, or time average WSS as for instance taught by Wentzel et al., "*Geometry guided data averaging enables the interpretation of shear stress related plaque development in human coronary arteries*", Journal of Biomechanics 2005, 1551-1555. FIG. 20 shows an example of a coronary vessel in which the WSS is superimposed on the luminal surface. FIG. 21, shows an example of a coronary vessel in which the pressure and fractional flow reserve is superimposed on the luminal surface. The generated 3D model may contain all the elements as described above within step 1801. The data obviously cannot be acquired or created during the intervention, with the exception of rotational angiography and biplane X-ray angiography. Therefore, this data needs to be available when starting the intervention, for instance on a server. This generated 3D model will be used later on.

Step 1802: Retrieve X-Ray Angiographic Image Data

Within step 1802, the X-ray angiographic image data is retrieved and is similar to step 101 of FIG. 1. Within a preferred embodiment the angiographic image data represents the acquisition of an object of interest by means of X-ray angiography, resulting in an X-ray angiographic image sequence. For example a single plane or bi-plane angiographic system can be used such as those manufactured, for example, by Siemens (Artis zee Biplane) or Philips (Allura Xper FD). The object of interest is for example the heart, a part of the coronary tree, or blood vessels and by means of a contrast medium the object of interest is visualized during the acquisition. Preferably, the electrocardiogram (ECG) is part of the angiographic image data and is simultaneously recorded during the X-ray angiography acquisition. The X-ray angiography image sequence is acquired in such a way that the object of interest is clearly visible. Therefore, the C-arm can be rotated and angulated by the clinician to obtain the best projection, also called optimal projection.

For the creation of the 3D roadmap as described by step 1803, it is important that the X-ray angiographic image sequence(s) are taken from a right perspective which is defined as the angulations of an X-ray system (both the system rotation and angulation) that contains as much information regarding the segment of interest as possible. In this perspective foreshortening and overlap of surrounding vessels are minimized. Foreshortening is the event when an object seems compressed when viewed from a certain perspective, causing distortion in the information. The perspectives in which an object of interest are visualized with minimum foreshortening are called optimal perspectives. In a preferred embodiment the 3D model as obtained from the 3D angiographic image data modality as described by step 1801 is used to suggest optimal perspectives to the user in terms of foreshortening and overlap of surrounding vessels. Of this 3D model the orientation is known relative to the X-ray system. An optimal perspective in terms of minimal foreshortening is determined as a perspective that is perpendicular to the orientation of the 3D model or a section thereof. Because the model can be looked at from different angles that are all perpendicular to it, a various number of optimal perspectives is possible.

However, an optimal perspective is not solely dependent on minimizing foreshortening but also on overlap of surrounding vessels. Therefore, a measure for this overlap is also taken into account. The overlap of surrounding vessels can be for one or multiple heart phases because due to movement, either of the heart itself or breathing motion, surrounding vessels can overlap the segment of interest during a certain time moment.

The 3D model extracted model as a result of step 1801 is back projected onto a 2D plane representing a certain perspective as taught by Lay, "*Linear algebra and its applications*", 2012, 4th edition, p142-143, Addison-Wesley Longman. Every point that is within the vessel of interest in the 3D model, is assigned a certain value. For every 3D point, its value is added to the corresponding 2D point in the back projected image. The plane with the maximum amount of 2D points containing a value, is the most desirable perspective in terms of minimal overlap.

Additionally, a perspective can be indicated in terms of minimal in-plane coronary motion. This perspective shows the vessel of interest with the least amount of in-plane coronary motion in the perspective. This allows the clinician to view the vessel of interest in a position where the vessel is as still as possible. A measure for the amount of in-plane coronary motion for each perspective can be determined for instance by back projecting the 3D model extracted from the CT data onto a 2D plane representing a certain perspective as taught by Lay, "*Linear algebra and its applications*", 2012, 4th edition, p142-143, Addison-Wesley Longman. For every centerline point of each vessel in the 3D model, a position is known. Then the 3D model extracted from CT data can be deformed using the motion model as taught by Baka et al, "3D+*t*/2D+*t* CTA-XA registration using population-based motion estimates", Demirci, Lee, Radeva, Unal (eds): MICCAI-STENT 2012, pp 64-71 to yield a 3D model at a different time moment. This deformed 3D model is then also back projected onto a 2D plane representing the certain perspective. Again the position of each centerline point is known but now for a different moment in time. For every centerline point the in-plane coronary motion can be determined by comparing the positions of each centerline point in both back-projections. The plane with the minimum amount of in-plane movement for all centerline points, is the most desirable perspective in terms of minimal in-plane coronary motion. This can be done for one or multiple heart phases.

Figure 22A:
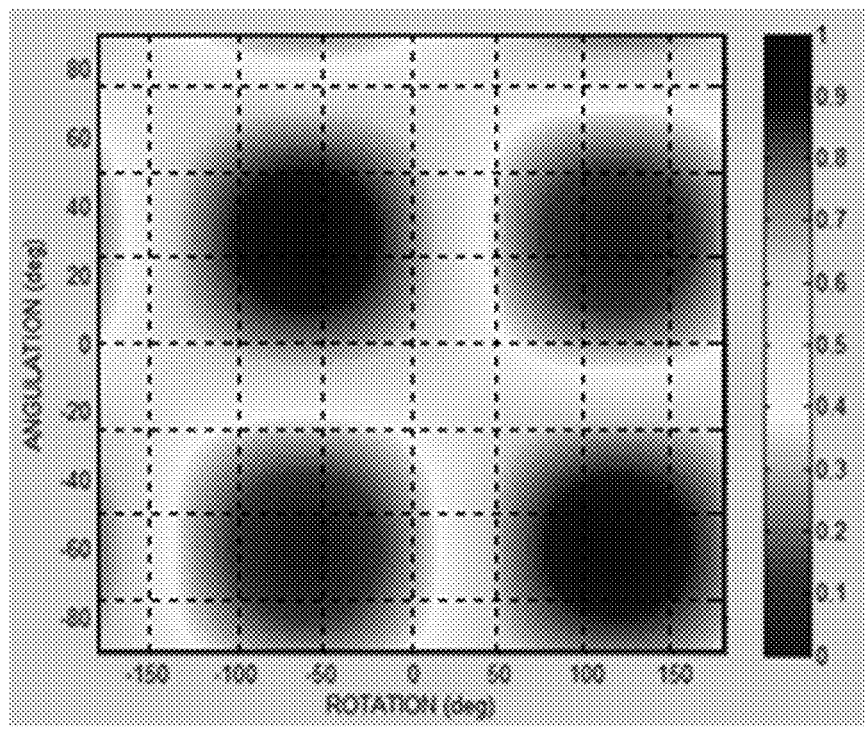
FIG. 22a shows a guidance map in terms of foreshortening, overlap and in-plane coronary motion of surrounding vessels for one heart phase.
Figure 22B:
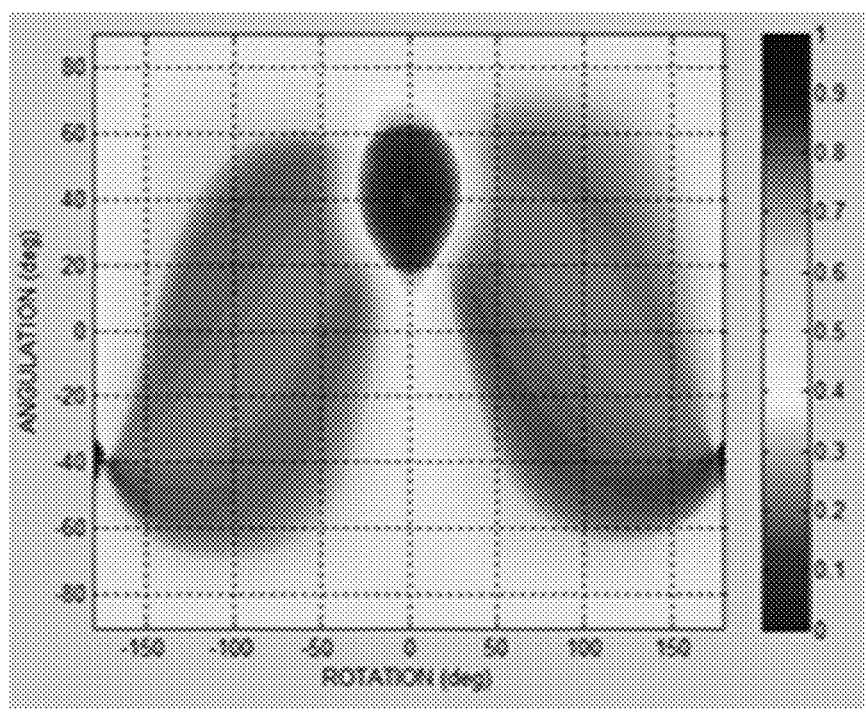
FIG. 22b shows a guidance map in terms of foreshortening, overlap of surrounding vessels and in-plane coronary motion including multiple heart phases.

Then for every combination of angulation and rotation (thus each perspective), it can be indicated how optimal the resulting perspective is. This indication is for instance a weighted sum of foreshortening, overlap of surrounding vessels and/or in-plane coronary motion for at least one heart phase. When multiple heart phases are taken into account, the calculations are done for each time moment that is for each frame. A weighted sum of all frames within the multiple heart phases is then made to obtain an overall indication of how optimal the perspectives are. This can be visualized for instance using a color map as shown in FIG. 22. FIG. 22*a* shows a color map in terms of foreshortening, overlap and in-plane coronary motion of surrounding vessels for one heart phase whereas FIG. 22*b* shows a grey scale map in terms of foreshortening, overlap of surrounding vessels and in-plane coronary motion including multiple heart phases. This map can obviously also be presented as a color map. Using this outcome the user can select a perspective from which the X-ray angiographic images sequence(s) can be acquired. In a preferred embodiment, two X-ray angiographic image sequence are acquired. However, in case the 3D model is available, at least one X-ray angiographic image sequence is required.

In case the 3D model is not available, two X-ray angiographic image sequence are required. The first X-ray angiographic image sequence is similar as described by step 101 of FIG. 1, and it is assumed that the physician selected an optimal projection to view the object of interest. The second projection can be acquired simultaneously while acquiring the first projection, and this is can be done with a bi-plane X-ray angiography system. Otherwise, the second projection can be acquired with in a mono-plane X-ray system, where the second projection is acquired after the first projection. The user can be supported in the selection of an optimal second projection with respect to the first projection. A projection map can be generated (2303 of FIG. 23) based on the first projection (2301) and the orientation of the object of interest in the first projection (2302). This method is described in full detail in EP3206183A1.

Step 1803: Create 3D Roadmaps

Within this step the sequence of 3D roadmaps (3D+t) will be created and is similar to step 103 of FIG. 1. This step (1803) results in the generation of 3D roadmaps of coronary arteries that cover multiple phases of at least one cardiac cycle. A 3D roadmap of a coronary arteries can be for example a vessel model. A vessel model might be in the form of centerlines, contours, masks, etc. Next to that, the vessel model might contain clinical relevant information, such as for example location and percentage of vessel obstruction, diameter and area, length of the vessel, pressure, blood velocity, fractional flow reserve, wall shear stress, the curvature of the vessel, the location and amount and type of coronary plaque, or the location and amount of calcified plaque. In contrast to the 2D roadmaps as used within the flowchart of FIG. 1, in current workflow 3D roadmaps are used. Since the 2D roadmaps are defined within the coordinate system of the X-ray image used to generate the 2D roadmap, 3D roadmaps are defined in a 3D world coordinate system, and therefore allowing arbitrary X-ray geometry. The 3D roadmaps are created from the frames within one cardiac cycle after contrast injection. Therefore, a full cardiac cycle is selected within the X-ray angiography image sequence(s) after the frame in which the contrast liquids enters the coronary artery. The frame within the X-ray angiographic image sequence in which the contrast liquid enters the coronary artery can be defined by the method as described before by step 501 of FIG. 5. Within step 1803, the 3D+t roadmaps can be generated by three different methods, and the method mainly depends on the available data from step 1801 and 1802.

Figure 24:
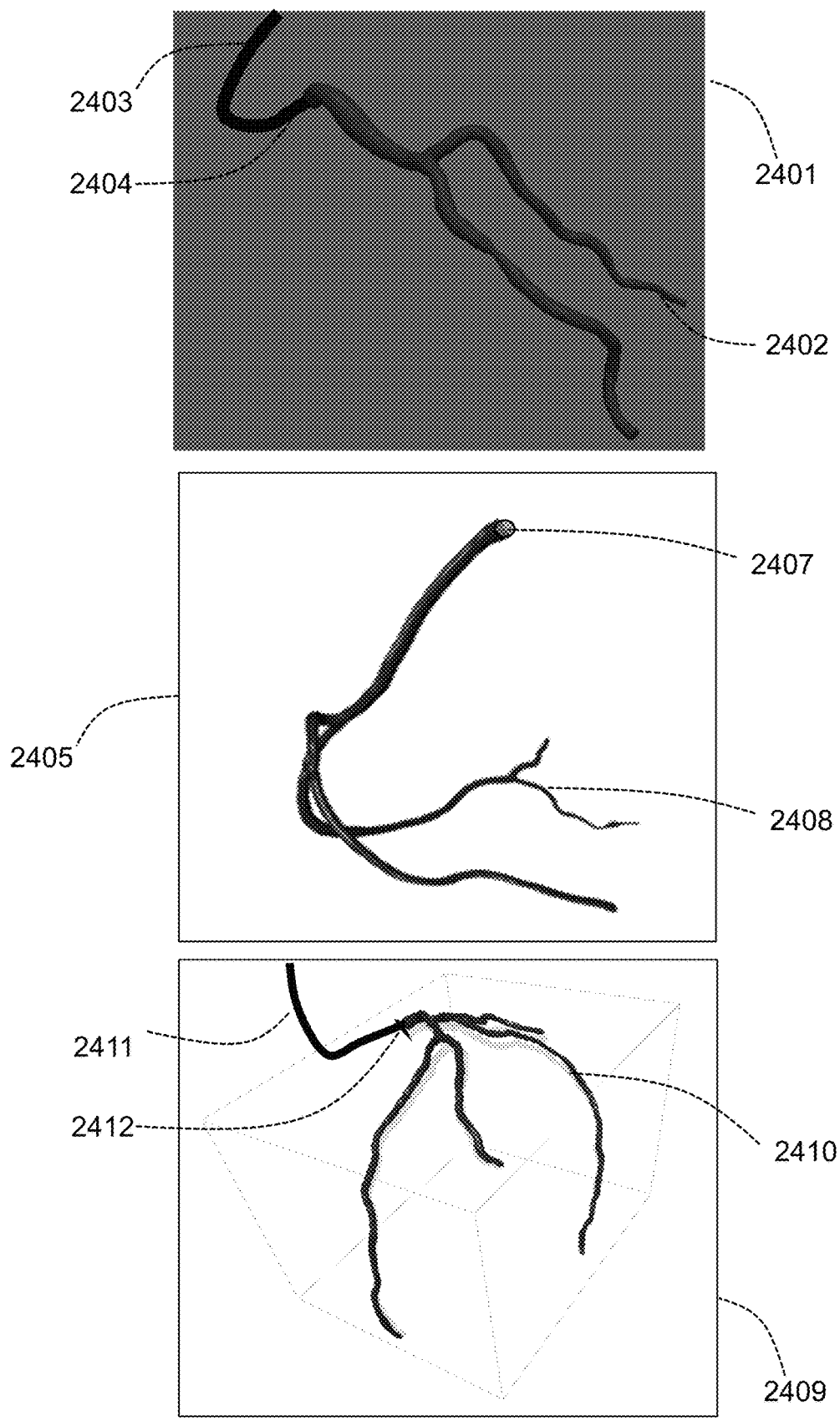
FIG. 24 shows some examples of a single 3D roadmap frame.

The first method (1803*a*) to create the 3D+t roadmaps is applicable in case step 1801 is not performed, and the 3D+t roadmaps are created by processing the two X-ray angiographic image sequences that result from step 1802. The 3D+t roadmap for all frames within one cardiac cycle after contrast injection can for instance be created by the method as taught by Chen et al, "*Kinematic and Deformation Analysis of* 4-*D Coronary Arterial Trees Reconstructed From Cine Angiograms*", IEEE Transactions on medical imaging, Vol. 22, No. 6, June 2003 pp 710-721, or as taught by Zheng et al, "*Sequential reconstruction of vessel skeletons from X-ray coronary angiographic sequences*", Computerized Medical Imaging and Graphics 34 (2010) 333-345. An example of a single 3D roadmap frame as a result of this step is provided by 2402 of FIG. 24. In case the X-ray angiographic image sequences are acquired with a biplane system, the temporal resolution of the 3D+t roadmaps can be improved by using the delay between each acquired frame with respect to frontal and lateral imaging source.

The second method (1803*b*) to create the 3D+t roadmaps is applicable when the 3D model is available as a result from step 1801 and one X-ray angiographic image sequence is available as a result from step 1802. Based on a method as taught by for instance Baka et al, "*Statistical coronary motion models for 2D+t/3D registration of X-ray coronary angiography and CTA*", Medical Image Analysis, Volume 17, Issue 6, August 2013, Pages 698-709. Within this work Baka et al proposed a method for building population based average and predicted motion from 4D CT datasets which is then used to perform 3D+t/2D+t registration based on distance minimization on one cardiac cycle. An example of a single 3D roadmap frame as a result of this step is provided by 2408 of FIG. 24.

The third method (1803*c*) to create the 3D+t roadmaps is applicable when the 3D model is available as a result from step 1801 and two X-ray angiographic image sequence are available as a result from step 1802. In this method both the 3D model resulting from step 1801 and a 3D reconstruction based on the X-ray angiographic image data as a result of step 1802 is combined to create the 3D+t roadmaps. This can be achieved as for instance by the methodology described in U.S. Pat. No. 10,229,516 "*Method and Apparatus to Improve a* 3D+Time Reconstruction", which describes a method for making a three-dimensional surface reconstruction over time of an object from two or more bi-dimensional x-ray images of the object. Alternatively, the 3D+t roadmaps can be created as for instance taught by Dibildox et al., "*3D/3D registration of coronary CTA and biplane XA reconstructions for improved image guidance*", Med Phys. 2014 Sep; 41(9), or as taught by Baka et al., "*Oriented Gaussian mixture models for nonrigid 2D/3D coronary artery registration*", IEEE Trans Med Imaging. 2014 May; 33(5):1023-34. An example of a single 3D roadmap frame as a result of this step is provided by 2410 of FIG. 24.

Optionally, based on the generated roadmaps, quantitative image analysis can be performed to extract clinical relevant information, such as for example location and percentage of vessel obstruction, diameter and area, length of the vessel or the curvature of the vessel as for instance taught by Girasis et al. in "*Advanced three-dimensional quantitative coronary angiographic assessment of bifurcation lesions: methodology and phantom validation*", EuroIntervention. 2013 Apr. 22; 8(12):1451-60 or as taught by Wang et al., "*Vessel extraction in coronary X-ray Angiography*", Conf Proc IEEE Eng Med Biol Soc. 2005; 2: 1584-1587.

Optionally, the generated roadmaps can be used to compute the cFFR along the coronary tree as for instance disclosed by U.S. application Ser. No. 16/438,955, which discloses methods to compute the fraction flow reserve along a coronary artery based on 3D coronary reconstruction obtained with X-ray angiography. The 3D+t model enables the calculation of the cFFR for every time point and takes into account the geometrical variation of the vessel tree part during a cardiac cycle and hemodynamic variation during the cardiac cycle. Optionally, the generated roadmaps can be used to compute the coronary WSS, or time average WSS as for instance taught by Wentzel et al., "*Geometry guided data averaging enables the interpretation of shear stress related plaque development in human coronary arteries*", Journal of Biomechanics 2005, 1551-1555. The time averaged WSS can be also be derived by calculating the WSS for all time points t within the 3D+t model. FIG. 20 shows an example of a coronary vessel in which the WSS is superimposed on the luminal surface. FIG. 21, shows an example of a coronary vessel in which the pressure and fractional flow reserve is superimposed on the luminal surface.

Optionally, the location and amount of calcified plaque can be extracted from the X-ray angiographic image sequence(s) as for instance disclosed in detail by the flowchart description of FIG. 28 further within this application.

Step 1804: Obtain Device within X-Ray Angiographic Image Data

Within step 1804 information is obtained to allow alignment (step 1808) of the 3D+t roadmap (as a result from step 1803) during the live overlay (1809) as part of the online phase (1810), and step 1804 is similar to step 102 of FIG. 1. As described by step 102, breathing motion, including possible patient motion, is compensated by identifying a reference point in the X-ray angiographic image sequence. The reference point (represented by a visible device in the image sequence) will be used for transformation of the object of interest or the roadmap during the online phase (1810). The reference point could be for example be the catheter tip, peacemaker or anatomical landmarks or any other object in which its motion can be correlated to the breathing motion and possible patient motion. Such a reference point can be obtained in every frame of the X-ray angiographic image sequence.

In case step 1801 is not performed, this step (1804) is identical to the steps 501, 502 and 503 as described by FIG. 5 and can be applied to both X-ray angiographic image sequences as a result from step 1802. Optionally the catheter-tip is reconstructed in 3D as for instance taught by Ambrosini et al., "*A Hidden Markov Model for 3D Catheter Tip Tracking With 2D X-ray Catheterization Sequence and 3D Rotational Angiography*", IEEE Trans Med Imaging. 2017 March; 36(3):757-768. Next, the obtained device location (e.g. catheter tip) are integrated in the 3D+t roadmap as created by the method 1803*a* as described by step 1803. Optionally, the device (e.g. catheter) is reconstructed in 3D and integrated in the 3D+t roadmap. As the 3D+t roadmaps are created within at least one cardiac cycle after start of contrast ($N_{after-contrast}$) and the device location is preferable extracted within at least one cardiac cycle before the start of contrast ($N_{before-contrast}$), temporal alignment needs to be established. This can be established by using the ECG signal. In case the X-ray angiographic image sequence(s) doesn't have a corresponding ECG signal, the extracted cardiac information is used as a result from step 502. An example of a single 3D roadmap frame as a result of this sub-step is provided by 2401 of FIG. 24, in which 2402 is a single 3D roadmap as a results of step 1803*a* and 2403 show the 3D reconstruction of the catheter and the catheter tip (2404) integrated in the 3D roadmap model as described above.

In case the 3D+t roadmap is created by the method 1803*b*, steps 501, 502 and 503 are applied to the single X-ray angiographic image sequence and no 3D reconstruction will be performed of the device. However, the device location as a result from step 503 is integrated in the 3D+t roadmap as created by the method 1803*b*. An example of a single 3D roadmap frame as a result of this sub-step is provided by 2405 of FIG. 24, in which 2408 represents a single 3D roadmap as a results of step 1803*b* and 2407 show the catheter tip (2407) integrated in the 3D roadmap model as described above.

In case the 3D+t roadmap is created by the method 1803*c* as described by step 1803 and at least two x-ray angiographic image sequences are available as a result from step 1802, the above described method is applicable as well. An example of a single 3D roadmap frame as a result of this sub-step is provided by 2409 of FIG. 24, in which 2410 represents a single 3D roadmap as a results of step 1803*c* and 2411 show the 3D reconstruction of the catheter and the catheter tip (2412) integrated in the 3D roadmap model as described above.

Step 1805: Retrieve Fluoroscopic Image Data

This step is identical to step 104 of FIG. 1, with the exception that in step 1805 arbitrary X-ray system geometry is allowed, such as arbitrary X-ray angulation and rotation, arbitrary X-ray magnification, arbitrary table position, etc., and the X-ray fluoroscopic image data may be either obtained from a single plane or bi-plane acquisition. Optionally, the X-ray fluoroscopy image data can be obtained with a bi-plane acquisition.

Optionally, since arbitrary X-ray system geometry is allowed within the flowchart of FIG. 18, a guidance map is visualized which support the physician in selecting the optimal X-ray fluoroscopic projection. Similar as described within step 1802 and based on the method as described in full detail in U.S. patent application Ser. No. 16/256,793 an optimal X-ray fluoroscopic projection is defined as a projection in which the X-ray viewing direction is perpendicular to the device (e.g. catheter). This device information is obtained based on the result of step 1804. Furthermore, such an optimal projection may include weighting of amount of foreshortening of the device, the less foreshortening the better the projection.

Step 1806: Select 3D Roadmap

This step is identical to step 105 of FIG. 1, where roadmap selection is based on ECG matching. The ECG signals associated with the online fluoroscopic image (see 1805 in FIG. 18) and the ECG of the offline angiographic sequence (see 1802 in FIG. 18), such that the most suitable candidate roadmap is selected where the best match of the ECG signals is found.

Alternatively, in the case that the X-ray fluoroscopy image data is obtained with a bi-plane acquisition, the images from both projections can be acquired shortly after each other with a small time delay, resulting in a high temporal resolution. Due to this high temporal resolution a more accurate roadmap selection takes place.

Step 1807: Track Device

This step is identical to step 106 in FIG. 1, where a device in the online fluoroscopic image data is tracked using for example deep learning based Bayesian filtering method.

Alternatively, in the case that the X-ray fluoroscopy data is obtained with a bi-plane acquisition, the tracking of the device can be performed in both X-ray fluoroscopy image projections separately according to the technique described in step 106 of FIG. 1. This results in two translations of the device with respect to the device location obtained in step 1804 in both bi-plane projections. Moreover, the catheter-tip can be reconstructed in 3D as for instance taught by Ambrosini et al., "*A Hidden Markov Model for* 3D *Catheter Tip Tracking With* 2D *X-ray Catheterization Sequence and* 3D *Rotational Angiography*", IEEE Trans Med Imaging. 2017 March; 36(3):757-768 and used to in the next step to transform the 3D roadmap.

Step 1808: Transform Selected 3D Roadmap to Generate Dynamic 2D Roadmap

This step is similar to step 107 in FIG. 1, which describes that a reference point is used to compensate for motion between the generated roadmaps obtained from the X-ray angiographic image sequence (offline phase) with the X-ray fluoroscopic image stream (online phase). Within step 1808, the same goal is obtained as described by step 107, with as difference that a) the roadmaps are 3D roadmaps, and b) the device can, besides a 2D location as the case in step 107, also be a 3D location or a 3D.

Within step 1808, the location of the device in current X-ray fluoroscopic frame, as a result of step 1807, and the device location (e.g. catheter tip) from the selected 3D roadmap frame as a result of step 1804 is used to obtain a transformation function to align the selected roadmap with the current X-ray fluoroscopic image frame. In embodiments, this transformation function might be a rigid transformation based on the displacement obtained from the catheter tip between the current frame and the catheter tip within the selected roadmap frame. Alternative the transformation function is a non-rigid transformation.

For example, a rigid transformation of the roadmap can be performed by using a rigid transformation function. Considering the original 3D roadmap as function R(x,y,z) (as a result of step 1806) and a transformation function T, then the transformation function can be as follows:

$$F(x,y,z)=T\{R(x,y,z)\} \quad \text{(equation 15)}$$

where F(x,y,z) is the transformed 3D roadmap. The transformation function T can be for example a displacement function, rotation function, scaling function, etc. Since arbitrary X-ray system geometry is allowed during the acquisition of the X-ray fluoroscopic frames by step 1805, the transformation function can take into account X-ray angulation, magnification and table movement and creates a 2D roadmap representing an imaging plane of the current X-ray fluoroscopic image frame. For instance, when the roadmap represents the vessel model as centerlines, or contours, the above transformation can be applied to each three-dimensional coordinate (x,y,z) of the centerlines or contours. In the case where the roadmap represents the vessel model as an image mask, the above transformation can be performed on the voxels (which map to three-dimensional coordinates x,y,z) of the volumetric image mask.

Alternatively, in the case that the X-ray fluoroscopy data is obtained with a bi-plane acquisition, the tracking of the device can be performed in both X-ray fluoroscopy image projections. In this case, the transformation as described above can be performed for each fluoroscopic projection and two 2D dynamic roadmaps are created.

Step 1809: Overlay Dynamic Roadmap on Fluoroscopic Image Data

This step is similar to step 108 in FIG. 1, with the transformed roadmap being rendered to produce a visual representation of the transformed roadmap which is overlaid on the respective live fluoroscopic image frame. In the case that the X-ray fluoroscopy data is obtained with a bi-plane acquisition, the visual representations of the two 2D dynamic roadmaps can be rendered and overlaid on the respective live fluoroscopic projections.

In embodiments, step 1809 can be accomplished by rendering the transformed model that results from step 1808 according to the viewpoint of the current live image in the live image stream/sequence of the patient. The pixels of the rendering of the model that correspond to the organ of interest (e.g., the coronary tree) can be assigned color values in a predefined range, such as a range of color values from red to white. Besides coloring the model, also transparency of the rendered model can be applied. Transparency of the model provides a dual view, where the X-ray fluoroscopy image is visible and the The mapping of the model to the dynamic roadmap overlay can be performed by translating the pixel intensities to color values where the color scheme represent quantitative parameters as described within step 1804.

Additionally, multiple overlays are rendered and integrated as an overlay on the live X-ray fluoroscopic or angiographic image stream. The overlay can exist of the 3D roadmap and in addition to the roadmap for example a 3D volumetric data or quantitative parameters. The 3D volumetric data needs to be back projected on the current X-ray fluoroscopic image frame based on the projection (view angle) in the same way as the 3D roadmap.

Obviously, step 1808 and 1809 might be performed in a slightly different order, in which in step 1808, results in a 3D transformed roadmap based on the information from step 1808 and 1807, and that in step 1809, this transformed 3D roadmap is back projected onto the current X-ray fluoroscopic image frame in which step 1809 handles the current X-ray fluoroscopic angulation, magnification and table movement during the back projection.

After step 1809, the method continues with step 1805 to process the next X-ray fluoroscopic image frame(s) and in case the retrieval of the X-ray fluoroscopic image data stops, as described by step 1805, the flowchart as described by FIG. 18 ends.

Within an alternative embodiment, subtraction is used as an image enhancement technique to improve the identification and processing of the object of interest. Image enhancement is a useful tool to improve the identification of an object of interest. An example of image enhancement is subtraction, where static objects and background are removed from the image of interest by subtracting this image with a baseline image.

Figure 15:
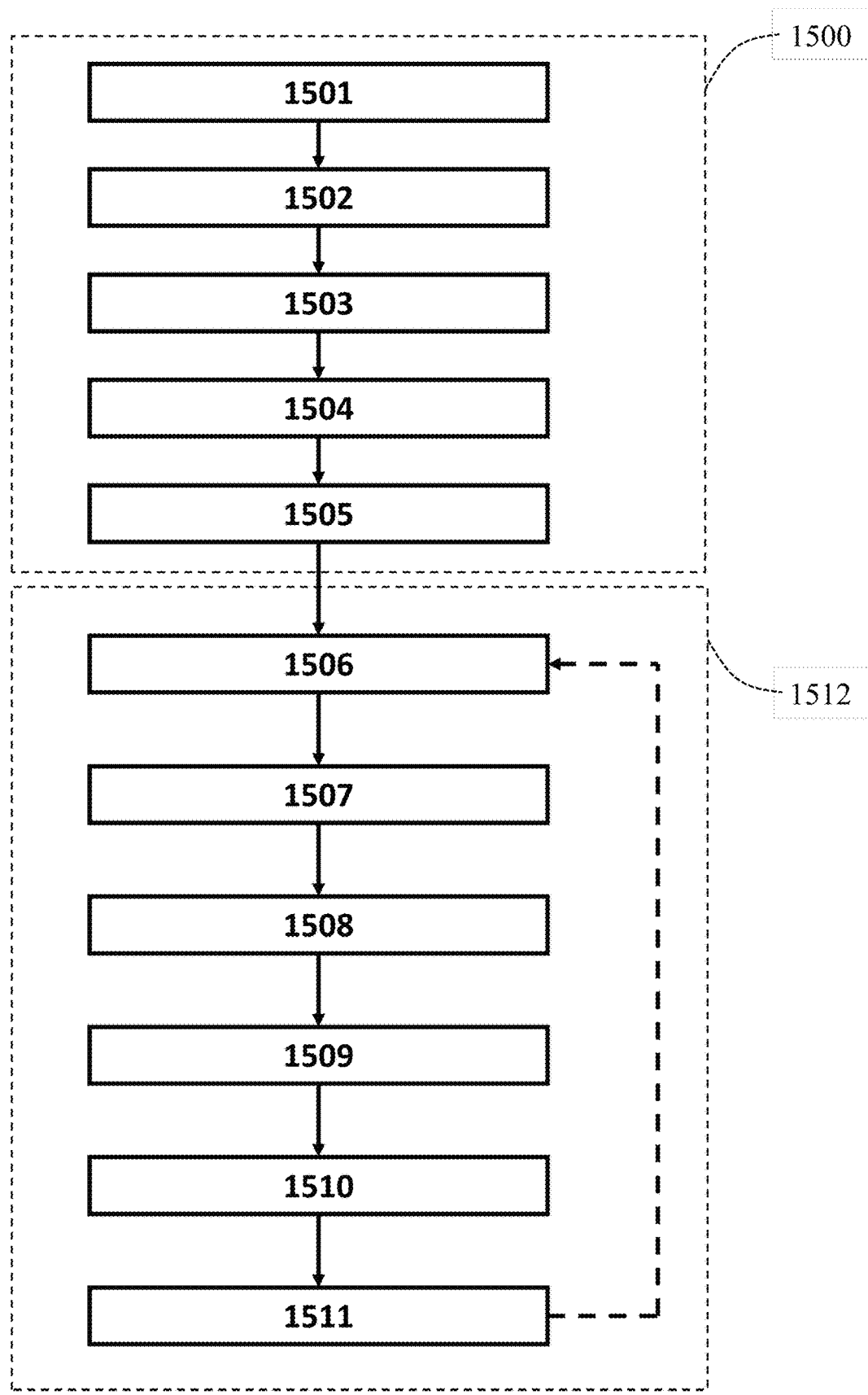
FIG. 15 shows a flow chart of a method for determining a dynamic coronary roadmap in which image enhancement is used to improve the identification and processing of the object of interest.

FIG. 15 presents the workflow similar to the workflow in FIG. 1 in which subtraction is used as an image enhancement technique to improve the identification and processing of the object of interest. There is an offline phase 1500 and an online phase 1512. Only an additional baseline image data set is retrieved, and image enhancement is performed by for example subtraction.

First the X-ray angiographic image data is retrieved 1501 including ECG, identical to 101 in FIG. 1. Next, an X-ray fluoroscopic image data (1502) is obtained including ECG with an identical projection (view angle) as in 1501 and where the catheter is pulled back from the ostium. The X-ray fluoroscopic image data of 1502 should contain one complete cardiac cycle and this image data is the baseline image sequence, where only the background and static objects are visible.

Figure 16:
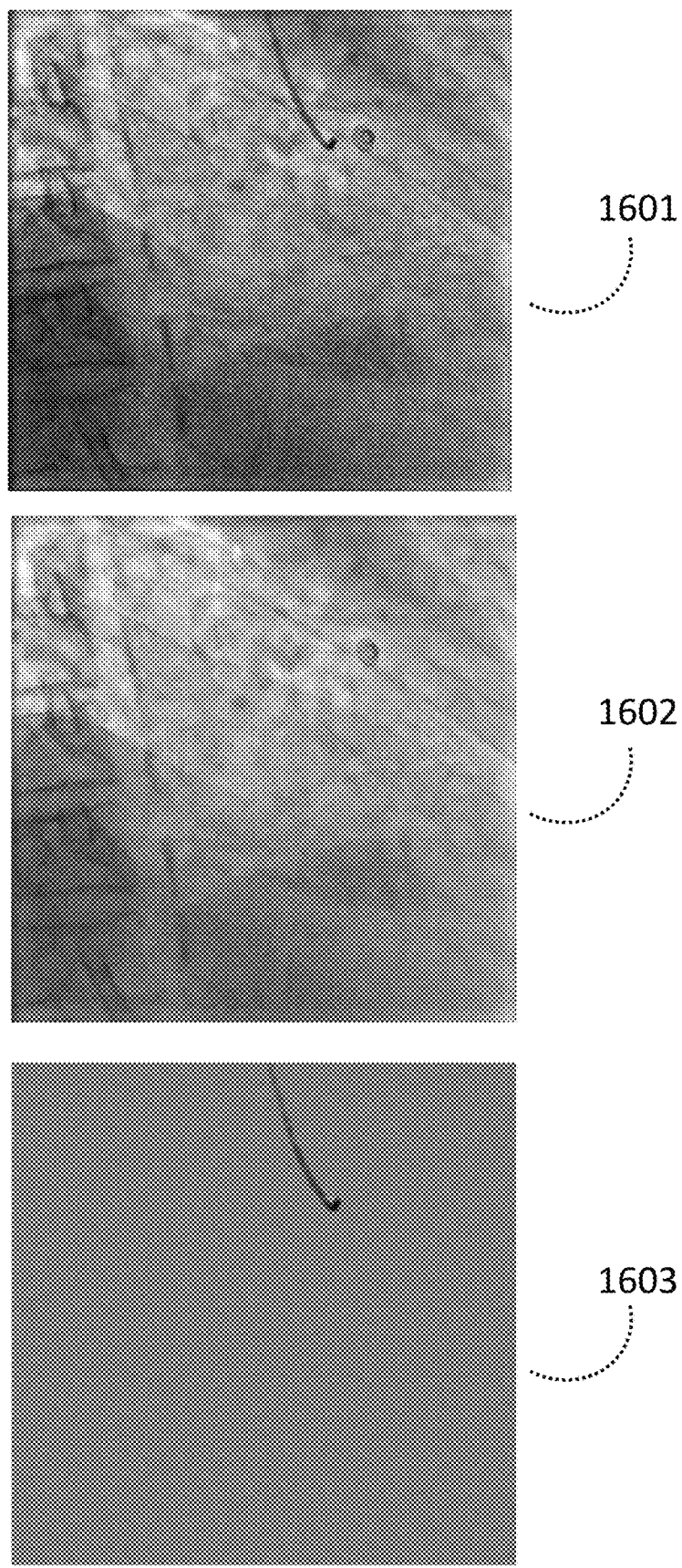
FIG. 16 shows an example of the image enhancement by means of subtraction.

Next in step 1503, one whole cardiac cycle of the X-ray fluoroscopic image data of 1502 is selected. For every frame of the X-ray angiographic image data of 1501 a baseline image frame of 1502 is selected based on ECG matching. The ECG matching can be performed as described in 105 of FIG. 1. After matching the X-ray angiographic image data and the baseline image data. The X-ray angiographic image data (see 1601 in FIG. 16) is subtracted with the baseline image data (see 1602 in FIG. 16) and results in an enhanced image (see 1603 in FIG. 16). In this enhanced image dynamic objects become clearly visible. Additionally, image processing techniques such as edge enhancement can be applied to improve the outline the object of interest.

The enhanced image resulting from 1503 is used to obtain the device location in step 1504. Step 1504 is identical to step 102 in FIG. 1. Next, roadmaps are created in step 1505 identical to step 103 in FIG. 1.

In the online phase 1512, the fluoroscopic image data is retrieved 1506 including ECG, identical to 104 with the same projection (view angle) as 1501 and 1502. Next in step 1507, image enhancement is applied to the x-ray fluoroscopic image of 1506, and the same process as in step 1503 is executed. This includes ECG matching of the X-ray fluoroscopic image data 1506 and the baseline data 1502. Subtraction of the X-ray fluoroscopic image data 1506 and the matched the baseline data 1502, resulting in enhanced x-ray fluoroscopic image data. Additionally, image processing techniques such as edge enhancement can be applied to improve the outline the object of interest.

Subsequently in step 1508, roadmap selection takes place identical to step 105 in FIG. 1. The enhanced X-ray fluoroscopic image step from step 1507 is used to track the device in step 1509. The device tracking is performed identical to step 106 in FIG. 1. Then in step 1510, the selected roadmap of step 1508 is transformed identical to step 107 in FIG. 1. Finally in step 1511, the roadmap is presented as an overlay on the X-ray fluoroscopic image data retrieved in step 1506. After step 1511, the method continues with step 1506 to process the next X-ray fluoroscopic image frame and in case the retrieval of the X-ray fluoroscopic image data stops, as described by step 1506, the flowchart as described by FIG. 15 ends.

Figure 26:
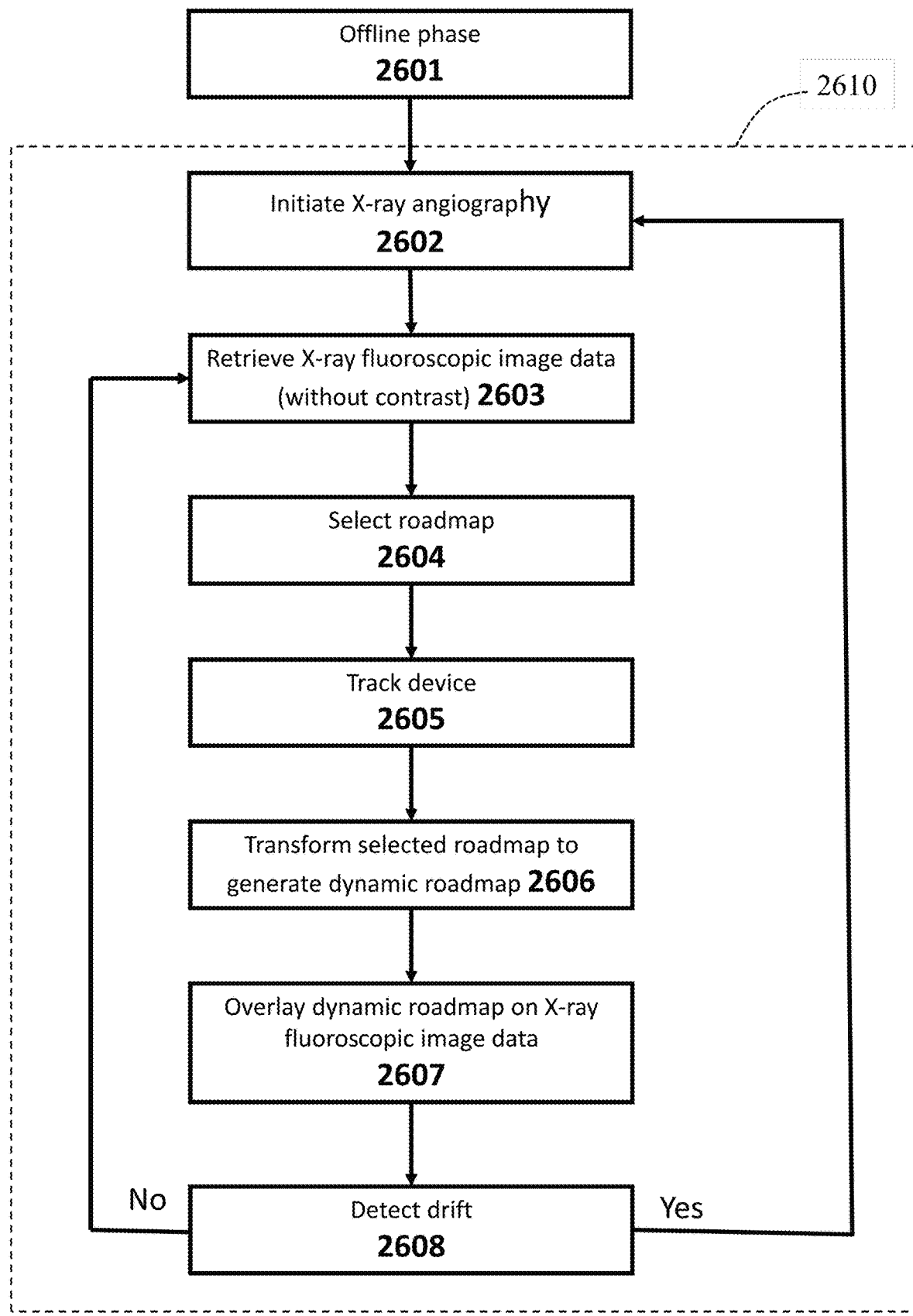
FIG. 26 shows a flow chart of an alternative method for determining a dynamic coronary roadmap.

Within an alternative embodiment, the online phase of the dynamic roadmapping can be reinitiated by means of an X-ray angiographic image stream and is represented by the flowchart of FIG. 26. Such an X-ray angiographic image stream is obtained during the live X-ray fluoroscopic image acquisition in which the physician injects a limited amount of contrast liquid, where after the roadmap is realign.

The flowchart of FIG. 26 is an alternative method either to the flowchart of FIG. 1 (2D roadmaps) or to the flowchart of FIG. 18 (3D roadmaps). The advantage of this alternative embodiment is: a) table movement is allowed during the online phase, b) additional devices which are introduced during the (live) procedure can be used for realignment an during the tracking phase; c) the physician is informed if the projected roadmap on the lice x-ray fluoroscopic image is misaligned. In the following sections, the steps within FIG. 26 are explained in more detail.

Step 2601: Offline Phase

Within step 2601, the sequence of roadmaps are created, and the steps are identical to the offline phase (100) represented by step 101, 102 and 103 of FIG. 1 incase the sequence of roadmap represents 2D roadmaps. In case 3D roadmaps are created, step 2601 is identical to the offline phase (1800) represented by step 1801, 1802, 1803 and 1804 of FIG. 18.

Step 2602: Initiate on X-Ray Angiography

Within this step, the roadmap is realigned to the current situation. With the term current situation refers to a true live status during the online phase (2610). Such a realignment may be useful for instance after table movement during the online phase (2610) or any other situation in which it plausible that the roadmap is misaligned to the current situation, or when additional devices which are introduced during the online phase to allow more accurate alignment. This step may be omitted when the system make the first transition from step 2601 to the online phase (2610). Step 2602 may be initiated from a signal triggered by the X-ray system, or another external system, after a contrast bolus injection was initiated. Alternatively, a contrast bolus injections is automatically detected by analyzing the X-ray fluoroscopic image stream (2603) as for instance taught by Ma et al., *Fast prospective detection of contrast inflow in x-ray angiograms with convolutional neural network and recurrent neural network*", International Conference on Medical Image Computing and Computer-Assisted Intervention, Springer (2017) 453-461, or as described by step 501 of FIG. 5.

The first sub-step within 2602 is the retrieval an X-ray angiographic image stream, which can be either obtained from a single plane or bi-plane acquisition. Once an amount of X-ray angiographic image frames are available, preferable an amount of frames covering at least one cardiac cycle, the roadmap is realigned to the current situation. Simultaneous with the X-ray angiographic image stream, the ECG signal is obtained as well.

Figure 27:
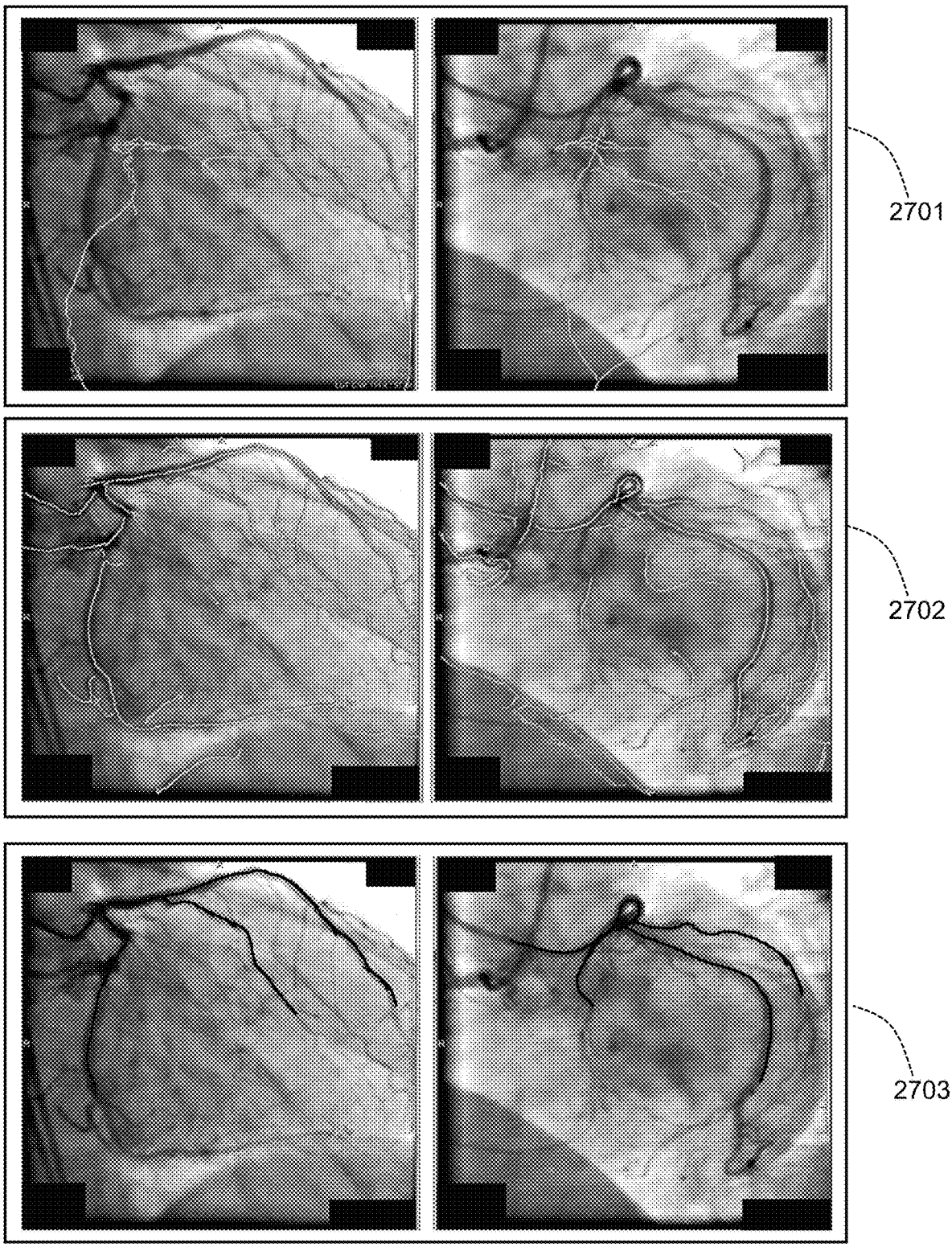
FIG. 27 shows an illustration of the realignment step.

In case the offline phase represents a 2D roadmap, the second sub-step within 2602 deals with update (recreation, or realignment) of the 2D roadmap sequence, and is identical to step 102 and 103 of FIG. 1. In case the offline phase represents a 3D roadmap, the second sub-step within 2602 is recreation of the 3D roadmap sequence, and is identical to step 1803 and 1804 of FIG. 18. FIG. 27 provides an illustration of the realignment step 2602 in case of a 3D roadmap. Picture 2701 shows the roadmap backprojected (2608) on the X-ray angiographic biplane as obtained within the first sub-step of 2602. Within 2701, the misalignment is visible which is for illustration purpose extremely misaligned. Picture 2702 shows the result of extracting of the 2D vasculature of the biplane image, which will be used to create a 3D model as described by step 1803 and 1804 of FIG. 18, and 2703 shows the aligned backprojected roadmap.

Alternatively, in the case that the image data is retrieved from acquiring multiple mono-plane images with different projections or a bi-plane acquisition in the offline phase, the device location can be determined according to step 102 in FIG. 1 or 1804 in FIG. 18 for every individual image data projection. Additionally, to the individual location of the device in every separate projections, a 3D device location can be determined based on the projection information of the image data.

Step 2603: Retrieve X-Ray Fluoroscopic Image Data

Within step 2601, the X-ray fluoroscopic image data is retrieved, and this step is identical to step 104 of FIG. 1. In case the offline phase represents a 3D roadmap (step 2601) an arbitrary X-ray system geometry is allowed, such as arbitrary X-ray angulation and rotation, arbitrary X-ray magnification, arbitrary table position, etc., and the X-ray fluoroscopic image data may be either obtained from a single plane or bi-plane acquisition. Moreover, as described by step 1805 of FIG. 18, a guidance map may be visualized which support the physician in selecting the optimal X-ray fluoroscopic projection.

Step 2604: Select Roadmap

Within step 2604 the current roadmap from the sequence of roadmaps as a result of step 2601 or in case updated, as a result from step 206 is selected. When the offline phase represents a 2D roadmap, this step is identical to step 105 of FIG. 1, or in case the offline phase represents a 3D roadmap, this step is identical to step 1806 of FIG. 18.

Alternatively, the X-ray fluoroscopy data is obtained with a bi-plane acquisition. With a bi-plane system the images from both projections are acquired shortly after each other with a small time delay, resulting in a high temporal resolution. Due to this high temporal resolution a more accurate roadmap selection takes place.

Step 2605: Track Device

Inn step 2605 the device is tracked within the live X-ray fluoroscopic image steam. When the offline phase represent a 2D roadmap, this step is identical to step 106 of FIG. 1, and in case the offline phase represents a 3D roadmap, this step is identical to step 1807 of FIG. 18.

Alternatively, the X-ray fluoroscopy data can be obtained with a bi-plane acquisition. In this case, the tracking of the device can be performed in both X-ray fluoroscopy image projections separately according to the technique described in step 106 of FIG. 1. This results in two translations of the device with respect to the device location obtained in step 2601 in both bi-plane projections.

Next to that, the device location can be determined as a 3D location based on both projections from the bi-plane acquisition as for instance taught by Ambrosini et al., "*A Hidden Markov Model for* 3*D Catheter Tip Tracking With* 2*D X-ray Catheterization Sequence and* 3*D Rotational Angiography*", IEEE Trans Med Imaging. 2017 March; 36(3):757-768. This enables a 3D tracking of the device.

Step 2606 Transform Selected Roadmap to Generate Dynamic Roadmap

In step 2606 the selected roadmap is transformed to create a dynamic roadmap for the current live X-ray fluoroscopic image frame. In the case that the offline phase represents a 2D roadmap, this step is identical to step 107 of FIG. 1. In the case that the offline phase represents a 3D roadmap, this step is identical to step 1808 of FIG. 18.

Alternatively, the X-ray fluoroscopy data can be obtained with a bi-plane acquisition. In this case, two translations are obtained in step 2605. These two translations and the 3D orientation of both image projections, results in a 3D transformation of the selected roadmap.

Step 2607: Overlay Dynamic Roadmap on X-Ray Fluoroscopic Image Data

When the offline phase produces 2D roadmaps, this step is identical to step 107 of FIG. 1. And, in the case that the offline phase produces 3D roadmaps, this step is identical to step 1808 of FIG. 18. Optionally, the way the roadmap is visualized on the X-ray image data may be altered. Since as a result of the contrast agent administrated within step 2602, the vessel structures will be enhanced as long as the contrast agent is in the vascular system, which depends on the amount and duration of the contrast injection and is on average around 5 cardiac cycles. To allow visual appreciation of the vascular structures as well as the projected overlay, the overlay may be projected on the X-ray image data in transparent mode as illustrated by 3401 in FIG. 34*b*. The amount of transparency can obviously be adjusted. Within FIG. 34*b*, 3402 provides another example in which the overlay is projected without obscuring the vascular structures of interest. This is accomplished by only showing the outer borders of the roadmap image, which may be generated by first dilating the roadmap by a predefined amount followed by extracting the boundaries of the dilated roadmap. Obviously, this can also be in transparent mode, in which the amount of transparency can be adjusted.

Step 2608: Detect Drift

During step 2608, the system detects if a realignment of the roadmap is required. For instance the X-ray systems triggers a signal incase the table is adjusted during the online phase (2610) or after a contrast administration was initiated. Optionally, within step 2608, misalignment of the roadmap can be detected by image processing of the X-ray fluoroscopic image stream. For instance comparison of the current image frame with the image frame at the same cardiac phase of the previous cardiac cycle. The comparison between both images can be performed by for example image registration, cross correlation or (minimum) difference. When applying image registration, the displacement resulting from the image registration is a measure of variation between both images and a threshold value can be defined to detect drift. In case of cross correlation, the cross correlation value represents the similarity between both images and for example a threshold value can be defined to detect drift. Alternatively, one image is shifted with respect to the other image and the cross correlation between both images is calculated for multiple shifts. Next, the maximum cross correlation value might correspond with a certain shift of the image. The magnitude of the shift is a magnitude of the drift. In case of the difference between both images, the difference value is a measure for the drift. A threshold value might be defined for drift detection. Alternatively, one image is shifted with respect to the other image and the difference between both is images calculated. The minimum difference can be calculated for multiple shifts and the shift that corresponds with the minimum difference is a measure for the drift.

Another method for drift detection is evaluation of the ECG signal. The ECG is a cyclic signal. In case of for example arrhythmia, the heartbeat is irregular and causes abnormal cardiac motion and the ECG signal deviates from a normal cycle. Deviations in the ECG signal may hamper the roadmap selection and may thereby cause incorrect overlaying of the roadmap. Therefore, evaluation of the ECG signal is useful to detect drift.

During regular respiration the diaphragm contracts, so called eupnea. For example, in case the patient suffers from hiccups, the diaphragm motion is irregular and therefore the motion of the object of interest might be irregular as well. The diaphragm contraction might be visible in the X-ray angiographic images. Tracking of the diaphragm in the X-ray image sequence can help to detect irregular respiration and the necessity for drift correction. Tracking the motion of the diaphragm can be performed as for instance taught by Ma et al., "*PCA-derived respiratory motion surrogates from X-ray angiograms for percutaneous coronary interventions*", Int J Comput Assist Radiol Surg. 2015 June; 10(6):695-705. Therefore, evaluation of the diaphragm contraction (motion) is useful to detect drift.

In case that step 2610 indicates that misalignment is present, step 2602 is initiated, otherwise the system continues with step 2603. In case the retrieval of the X-ray fluoroscopic image data as described by step 2603 stops, the flowchart described by FIG. 26 ends.

Figure 30:
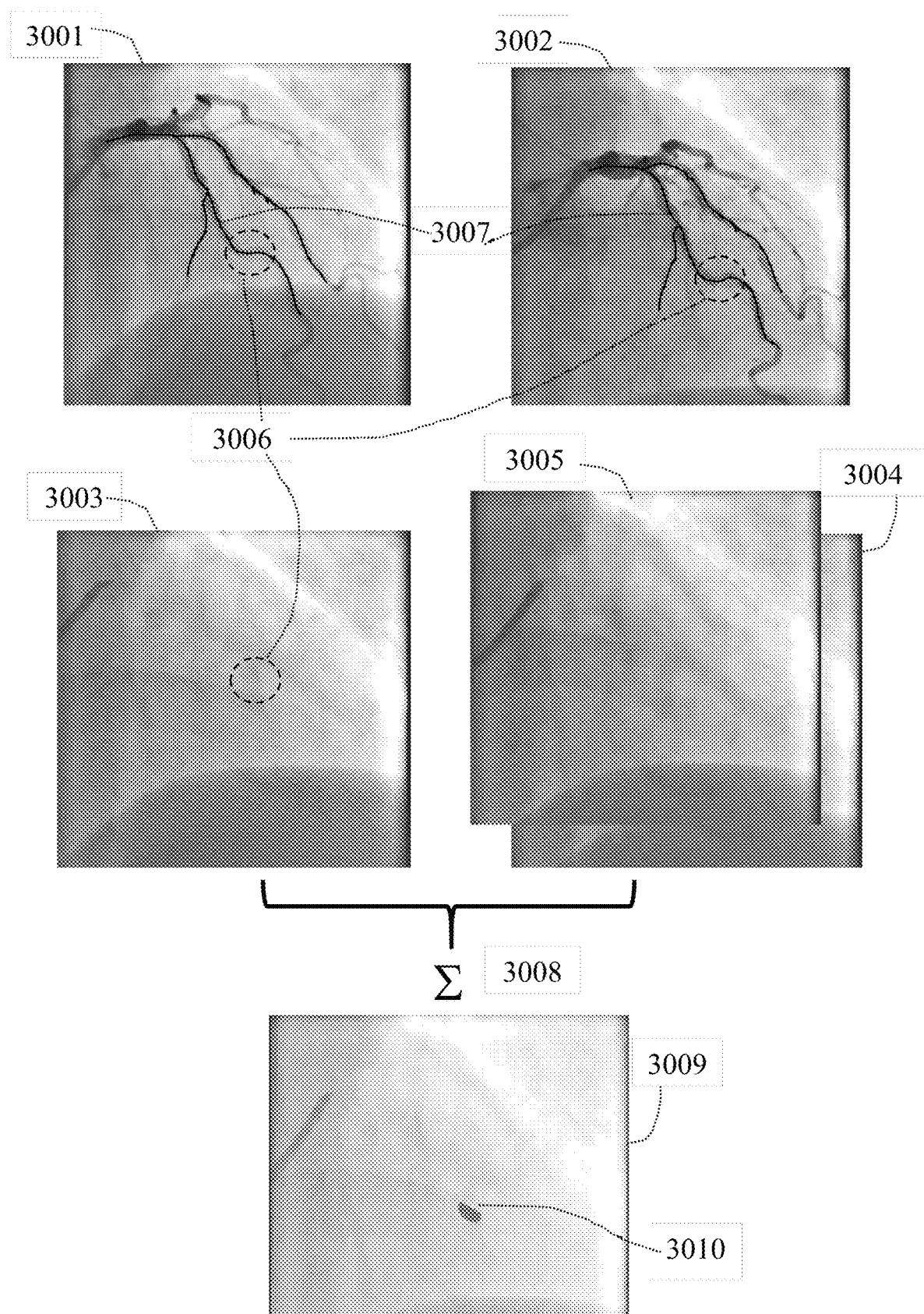
FIG. 30 shows the high-level method for determining the location and amount of calcified plaque.

Although calcified plaque is radiopaque, its presents cannot be appreciated on a single X-ray image frame, and is hardly visible when assessing a sequence of X-ray images. FIG. 28 represents a flowchart that illustrates an embodiment that's extract the location and amount of calcified plaque by means of X-ray image data. The X-ray image data may represent an X-ray fluoroscopic image sequence or an X-ray angiographic image sequence in which the X-ray angiographic image sequence contains image data before and after the administration of a contrast agent. On both cases, the ECG signal is considered to be part of the X-ray image data. FIG. 30 illustrates the challenge in identifying calcified plaque. Within FIG. 30 the high-level method as described by the flowchart of FIG. 28 is illustrated. Within the dashed circle (3006) calcified plaque is present, however this is hardly assessable within the images (3001, 3002, 3003 and 3005). By adding the image information, after registering the images, into a single image (3009), the calcified plaque (3010) is enhanced and visible. Furthermore, quantitative analysis can be performed on the enhanced calcified plaque. In the following sections, the steps within FIG. 28 are explained in more detail.

First at step 2801, the X-ray image data is retrieved. As described before this can be either an X-ray fluoroscopic image sequence or an X-ray angiographic image sequence which contains image data before and after the administration of a contrast agent. First the steps will be described in case the X-ray image data represents X-ray angiographic image data, and afterwards the method is explained in case the X-ray image data represents X-ray fluoroscopic image data. In all cases it is assumed that the ECG signal is part of the X-ray image data.

Figure 29:
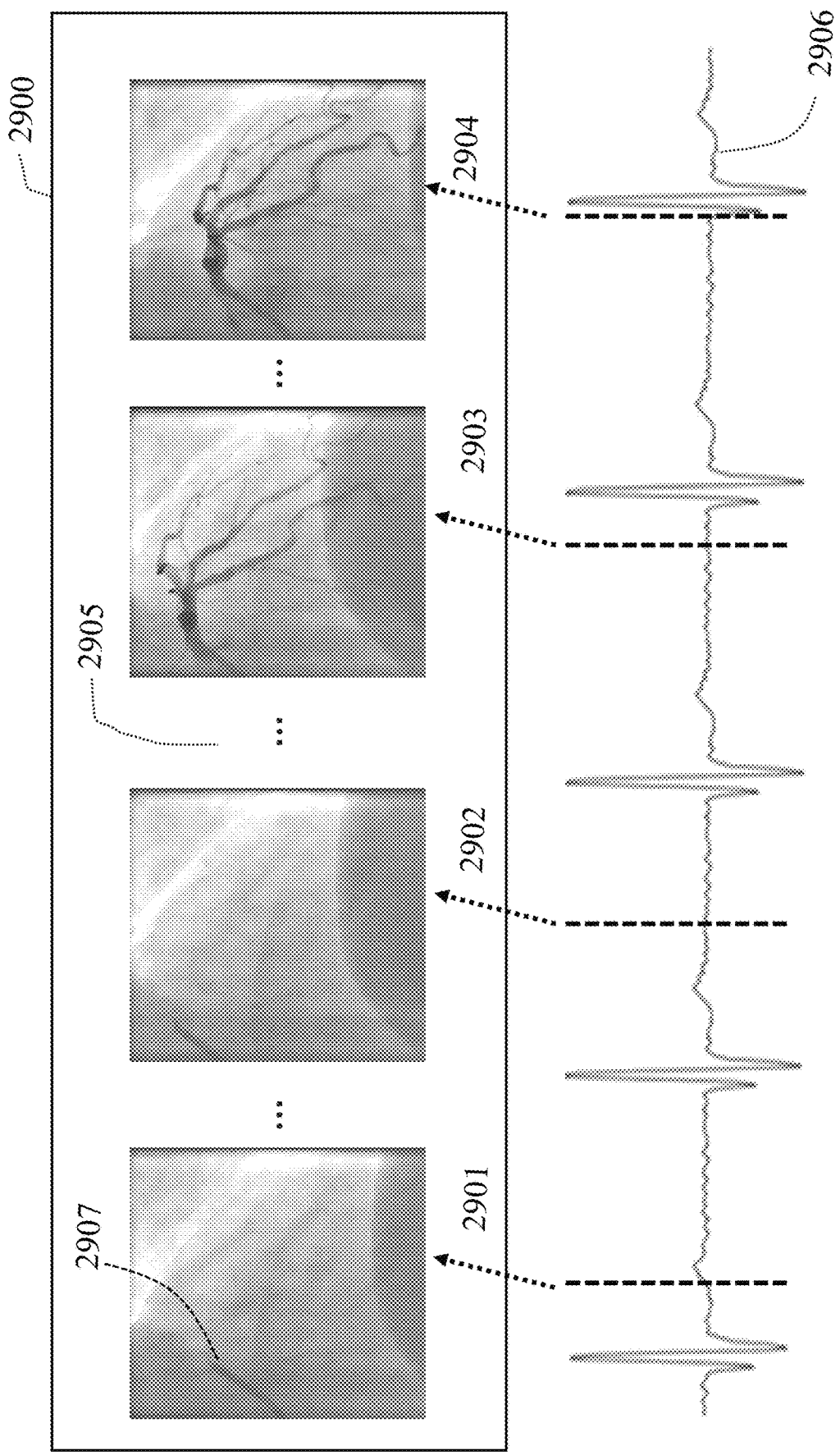
FIG. 29 shows a typical example of an X-ray angiographic image sequence in which contrast agent is administered during the sequence.

FIG. 29 shows a typical example of an X-ray angiographic image sequence, in which 2900 illustrates a number of sequential X-ray image frames within such a sequence, and 2906 shows the corresponding ECG signal. Within FIG. 28, the moment of administration of the contrast agent is presented by 2905 and the frame before (2901, 2902) shows the X-ray image data without enhancement of vascular structures beside the catheter (2907). After the administration of the contrast agent, the frames also represent the vascular structures (2903, 2904), and in current example the left coronary artery. Furthermore, the moment in which each X-ray frame was obtained with respect to the ECG signal is visualized (2901, 2902, 2903 and 2904).

Alternatively, the properties of the X-ray beam may be changes in such a way that calcified tissue absorbs X-ray more efficient than its surrounding tissue. In applications for assessment of vascular structures, the properties of the X-ray beams are defined in such a way that there is an optimal X-ray absorption of the iodine rich contrast liquid with respect to its surrounding tissues. There are two primary means that define the properties of the X-ray beam produced by the tube: a) altering the current (mA) and b) altering the voltage (kV). The current (measured in and often referred to as mA, or milliamperes) across the tube determines how many electrons are released to strike the anode. Increasing the mA will increase the number of electrons that strike the anode, with a consequent linear increase in the number of photons produced by the tube. The voltage across the X-ray tube (measured in and often referred to as kV, or kilovolts) affects the velocity of the electrons as they strike the anode; this affects the energy of the photons that can be produced by the tube. Additionally, higher velocity electrons will produce more photons, something on the order of $(kV)^3$. There are two major ways in which X-ray beams interact with tissue. The first is the photoelectric effect, where a photon uses up all of its energy to eject an electron from an atom; while the electron will move around and ionize neighboring atoms, there are no scatter photons. The second major effect is Compton (incoherent) scatter, where a photon hits an atom and ionizes an electron but does not use up all of its energy. The photon then scatters in a different direction with a bit less energy, and the free electron goes about doing damage. Scattered photons can travel back towards the tube, pass through the patient and hit the detector from any odd angle, or scatter again within the patient. As the X-ray beam passes through tissue, photons get absorbed so there is less energy; this is known as attenuation. Higher energetic photons travel through tissue more easily than lower energetic photons (this means that the higher energy photons are less likely to interact with matter). Much of this effect is related to the photoelectric effect; the probability of photoelectric absorption is approximately proportional to $(Z/E)^3$, where Z is the atomic number of the tissue atom and E is the photon energy. As E gets larger, the likelihood of interaction drops rapidly. Compton scattering is about constant for different energies although it slowly decreases at higher energies. So alternatively, the X-ray fluoroscopic image sequence or the X-ray angiographic image sequence is acquired in which the tube properties (tube voltage and/or tube current) of the X-ray system is optimized in such a way that calcified tissue absorbs X-ray more efficient than its surrounding tissue.

Next at step 2802, the vessel of interest is obtained. This can be either by methods as described by step 103 of FIG. 1 or the outcome of step 103, or by methods as described by step 1803 of FIG. 18 or the outcome of step 1803, or the user manual identifies the vessel of interest.

At step 2803 the frame from the X-ray angiographic image sequence in which the contrast liquid enters the coronary arteries is identified and identified as $f_{start\text{-}contrast}$. This step can be accomplished for instance by the methods as described by step 501 of FIG. 5.

Figure 31:
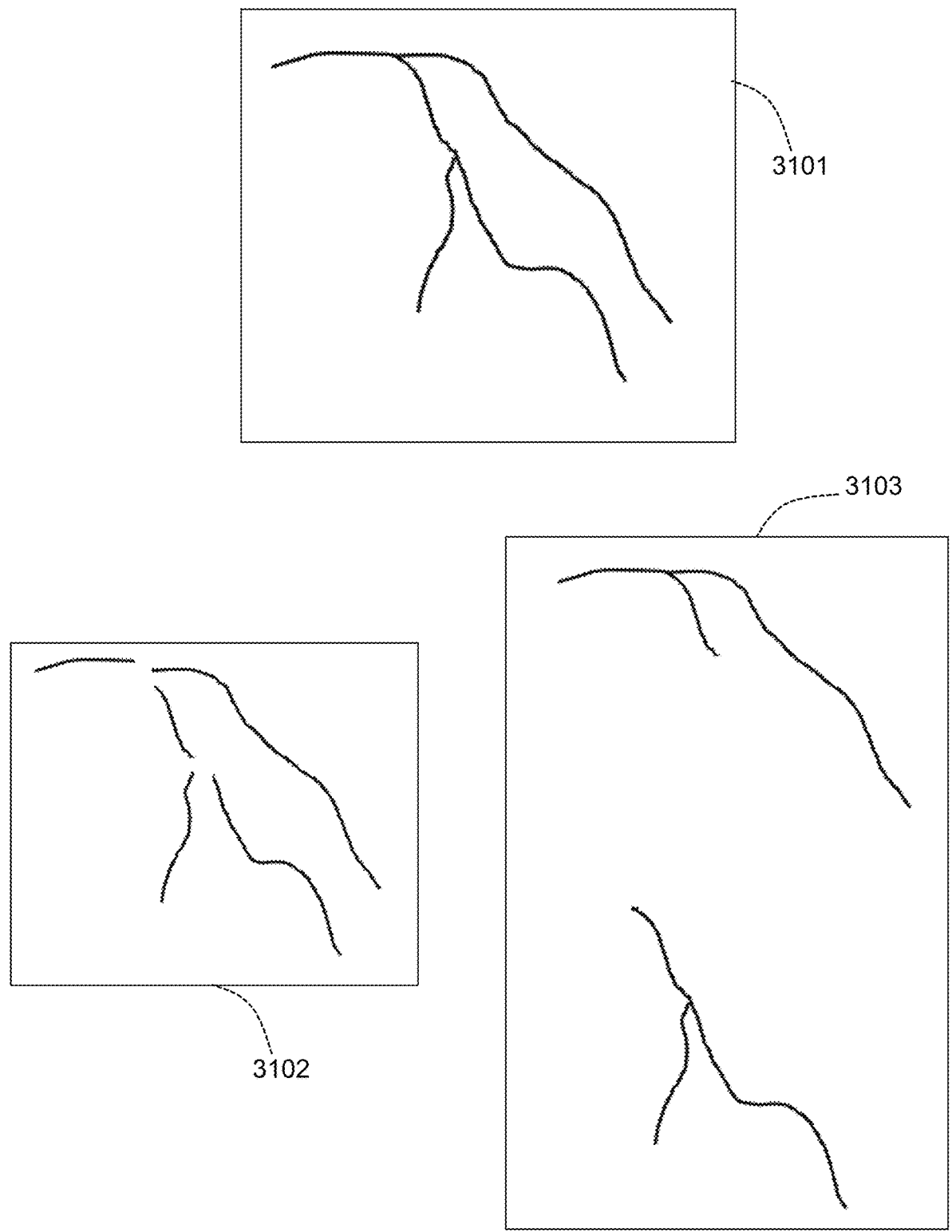
FIG. 31 shows the skeleton is decomposed into separate vessel branches.

Next, at step 2804 the vessel skeleton is detected in each frame within the sequence after the start of contrast ($f_{start\text{-}contrast}$) as a result of step 2803, and preferably the vessel skeleton is detected in an amount of sequential frames representing at least one cardiac cycle. Preferable at least three cardiac cycles are available. The vessel skeleton can be detected for instance as taught by Zheng et al., "*Sequential reconstruction of vessel skeletons from X-ray coronary angiographic sequences*", Computerized Medical Imaging and Graphics 34 (2010) 333-345. An example of is such a vessel detection within two X-ray angiographic image frames is provided by 3001 and 3002 within FIG. 30, in which the skeleton is indicated by 3007. Next, the skeleton is decomposed into separate vessel branches, as illustrated by FIG. 31. This decomposition can be either on branch level (3102) or on bifurcation level (3103). Furthermore, all detected skeletons which were not part of the vessel of interest (2802) are removed. This can be accomplished by identifying the frame from the sequence of detected skeletons which best matches the cardiac phase as used in step 2802, as for instance described within step 105 of FIG. 1 (section ECG matching for roadmap selection), and remove the skeletons (in all frames) which were not part of the vessel of interest.

Within step 2806, the selected corresponding fluoroscopic images as a result of step 2805 are registered to each other. The registration is performed on each decomposed vessel branch as described by step 2804. Optionally, landmarks are automatically identified from the skeleton and/or decomposed skeleton to improve the performance of the registration, such landmarks can for instance be the point of bifurcation (3104) or start/end position (3105) or high local curvature (3106). The 2D to 2D registration can be performed for instance as taught by Maintz et al., "*An overview of Medical Image registration Methods*", In symposium of the Belgian hospital physicists association, 1996, or as taught by Rohr at al., "*Landmark-based elastic registration using approximating thin-plate splines*", IEEE Trans Med Imaging. 2001 June; 20(6):526-34.

Within step 2807, the image in which the calcified plaque is enhanced is generated. Before generating the enhanced image, the registered X-ray fluoroscopic images (as a result of step 2806) are preprocessed. X-ray images typically suffer from a transparent background layer potentially obscuring the calcified plaque. In order to enclose the influence of this effect, background subtraction is performed. A simple and effective method for removing a static transparent layer uses the assumption that each individual layer can only add mass. Taking for each pixel the maximum intensity over time (lower pixel intensities absorbs x-ray) will yield an image showing the least amount of mass over time. Assuming that all pixels will not contain any contributions from moving mass layers at some point in time, the maximum intensity image is equal to the static background layer. Often, a single general mask image is created for each frame, for instance based on the maximum intensity of each pixel through all frames like discussed before. However, such a single mask image suffers from artifacts due to large, slow moving objects in the background (like for instance the diaphragm, ribs and/or lungs). Therefore, the background subtraction performed determines a more local background mask of x amount of successive frames symmetrically around the respective frame, in which x is typically 5 frames. Alternatively, the static background layer can be generated as taught by Ma et al., "*Layer separation for vessel enhancement in interventional X-ray angiograms using morphological filtering and robust PCA*", Workshop on Augmented Environments for Computer-Assisted Interventions 2017, Springer. pp. 104-113 or by Ma et al., "*Automatic online layer separation for vessel enhancement in X-ray angiograms for percutaneous coronary interventions*", Med Image Anal. 2017 July; 39:145-161.

Next, the preprocessed frames are combined into a single image frame. This is performed by adding (3008 of FIG. 30) the preprocessed frames, and optionally a weighting factor is introduced which correlates to the likelihood of non-rigid deformation of each frame, for instance due to foreshortening. An example of a result of this process is presented by 3009 of FIG. 30. Within picture 3009, the calcified plaque is enhanced (3010).

Figure 32:
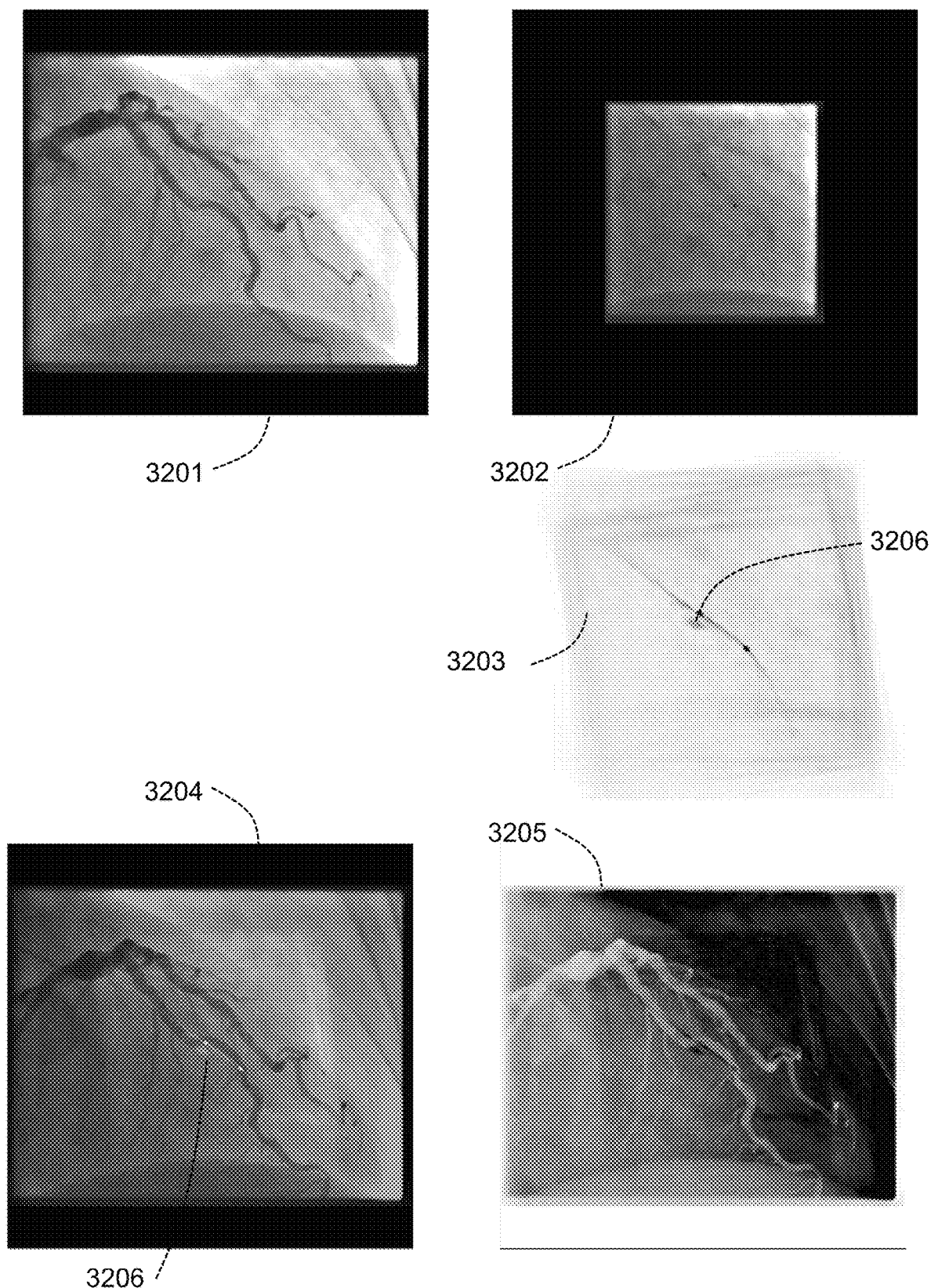
FIG. 32 shows an example of the calcified plaque enhancement.

Before continuing with step 2808, the method of FIG. 28 will now be described in case the X-ray image data represents X-ray fluoroscopic image sequence (as a result from step 2801). In this case it is assumed that a device is present inside the vessel of interest which contains radiopaque markers. This can be for instance an un-deployed stent, a measurement guidewire, or any other device which moves synchronic with the movement of the vessel of interest. Within FIG. 32, 3202 an example is provided of an un-deployed stent. Step 2803 is not applicable for X-ray fluoroscopic image sequence and step 2804 now detect and traces the radiopaque markers within the X-ray fluoroscopic image sequence. Since all image frames within the X-ray fluoroscopic image sequence are fluoroscopic image frames, step 2805 is not applicable. Within step 2806, the traced radiopaque markers are used to register the images to each other, and step 2807 is identical as described before. FIG. 32 provides a visual illustration, in which the enhanced calcified plaque image is superimposed on an x-ray angiographic image frame aligned by means of ECG with the enhanced calcified plaque image. Image 3202 shows a single image frame within the X-ray fluoroscopic image sequence, and image 3203 is shows the result of the enhanced calcified plaque image. Image 3201 shows an x-ray angiographic image frame aligned by means of its ECG with the image 3203. Image 3204 shows the result of subtraction the enhanced calcified plaque image from the x-ray angiographic image frame, and image 3205 shows the result of dividing the enhanced calcified plaque by the x-ray angiographic image frame. In both images 3204 and 3205, the calcified plaque location and amount of visible with respect to the vessel lumen.

Referring back to FIG. 28, the final step 2808 involves quantitative analysis of the enhanced calcified plaque. The area of the calcified plaque (3010, 3206) can be calculated by manual and/or (semi)automatic detection of the calcified plaque (calcified plaque region) with the enhanced image (3009, 3204). Videodensitometric analysis can also be performed. The volume and/or mass of the calcified plaque can be derived by comparing the density of the calcified plaque region to another radiopaque region within the enhanced image or the X-ray image data (2801). When knowing the properties of the radiopaque region, such as geometry and its (mass) attenuation coefficient, the volume and/or mass of the calcified plaque region can be computed by using the Beer-Lambert law. The radiopaque region can also be a region of the vessel as obtained from the X-ray angiographic image sequence. In this situation, the (mass) attenuation coefficient of the contrast agent needs to be known to be able to compute the volume and/or mass of the calcified plaque region by using the Beer-Lambert law. Alternatively, videodensitometric analysis can be performed as for instance disclosed by U.S. Pat. No. 9,576,360.

In general, the X-ray image data contains corresponding ECG signal recording. In case the X-ray image data does not contain ECG information, cardiac phase matching of the contrast and non-contrast images based on the ECG signal is not possible. To overcome this problem, a heart model can be used that mimics the cardiac motion. Such a heart model might be generated from for example CT acquisitions of a number of hearts. The cardiac motion is extracted from the image data and a model is generated that mimics the cardiac motion.

The cardiac motion model provides the cardiac motion in 3D+t. Based on the X-ray angiography acquisition, the expected cardiac motion of the heart in a specific projection can be extracted from the cardiac motion model.

The cardiac motion model is applied to both the contrast and non-contrast image and for example the correlation between both images is calculated to identify the best match between both images as for instance taught by Metz et al., "*Patient Specific 4D Coronary Models from ECG-gated CTA Data for Intra-operative Dynamic Alignment of CTA with X-ray Images*", Med Image Comput Assist Interv. 2009; 12(Pt 1):369-76.

Other Applications

The embodiments described above are associated to provide a real time dynamic overlay or dynamic coronary roadmap which can be superimposed on the live X-ray fluoroscopic or angiographic image stream/sequence.

In embodiments, the methods described within the current application can also be used to provide static guidance, meaning selecting of only one roadmap within the sequence of roadmaps. Preferably, a roadmap is selected in which the coronary artery has the least cardiac motion. Furthermore, the 3D model as created from 3D angiographic image data as described by step 1801 of FIG. 18 can be used as a static roadmap to be superimposed in the x-ray image data. Optionally, a registration to the x-ray Image data can be performed by for instance techniques as describes before or as disclosed by current application. For instance, the model as presented by FIG. 25 which also includes coronary plaque information may be used as static guidance.

In other embodiments, the described method can be used as pre-procedural planning, and optionally X-ray angiographic image can be simulated as for instance described by U.S. Pat. No. 10,192,352 for improved preparation for the actual PCI procedure.

Alternatively, a single roadmap can be selected. The image related to the selected roadmap can be used as reference image. The relation between the roadmap and the reference image can be determined, for example, using the ECG signal of the patient. Next, all images of the live X-ray fluoroscopic or angiographic image stream/sequence are registered with the reference image. Due to the image registration, the images of the live X-ray fluoroscopic or angiographic image stream/sequence are "freezed" and are aligned with the static roadmap. The image registration can be performed by methods known in the art, which are taught by for example Maintz et al., "An overview of Medical Image registration Methods", In symposium of the Belgian hospital physicists association, 1996.

The embodiments described above are associated to provide a real time dynamic overlay or dynamic coronary roadmap which can be superimposed on the live X-ray fluoroscopic or angiographic image stream/sequence. Alternatively, the embodiments, with special focus on the extract roadmaps as described by FIG. 1, FIG. 15, FIG. 18 and FIG. 26 may also be used in the field of robotic assisted percutaneous coronary interventions (PCI) or peripheral vascular interventions.

From the first introduction of PCI in the 1970s, interventional cardiology has undergone significant evolution in device technology, treatment procedures and pharmacotherapy, which have mean treatment of the most complex lesion (such as total coronary occlusion) possible. Despite the steady growth of progress in nearly all facets of the coronary intervention field, the mechanical aspects of PCI, such as manipulating of coronary guidewires, balloons and stents and the occupational hazards for operators and catheterization laboratory staff remains largely unchanged since its introduction in the 1970s. The interventional cardiologist works under the guidance of direct fluoroscopy to manipulate intravascular devices, and this requires dress in heavy protective garments. Over the course of an interventional cardiology career, operators are subject to the adverse consequences of cumulative radiation exposure and an increased prevalence of orthopedic injuries.

A robotic system that takes over the manipulations of the intravascular devices would significantly decrease the above mentioned short comes and hazards and could revolutionize percutaneous coronary intervention procedures. Such a robotic assisted PCI system, although still in its infancy, is for instance manufactured by Corindus vascular robotics.

One of the requirements of such a robotic system is to manipulate at submillimeter level the intravascular device and requires knowledge of the 3D geometry and morphology of the vasculature. This also involves knowledge during the procedure on changes in 3D shape of the vasculature as for instance due to cardiac motion, breathing motion and/or patient motion. Using the methods as described in current application integrated in a robotic system that takes over the manipulations of the intravascular devices can potentially improve patient outcomes and allows an advanced pre-procedure planning tool with robotic precision to bring a new revolutionary standard of care to patients.

Figure 17:
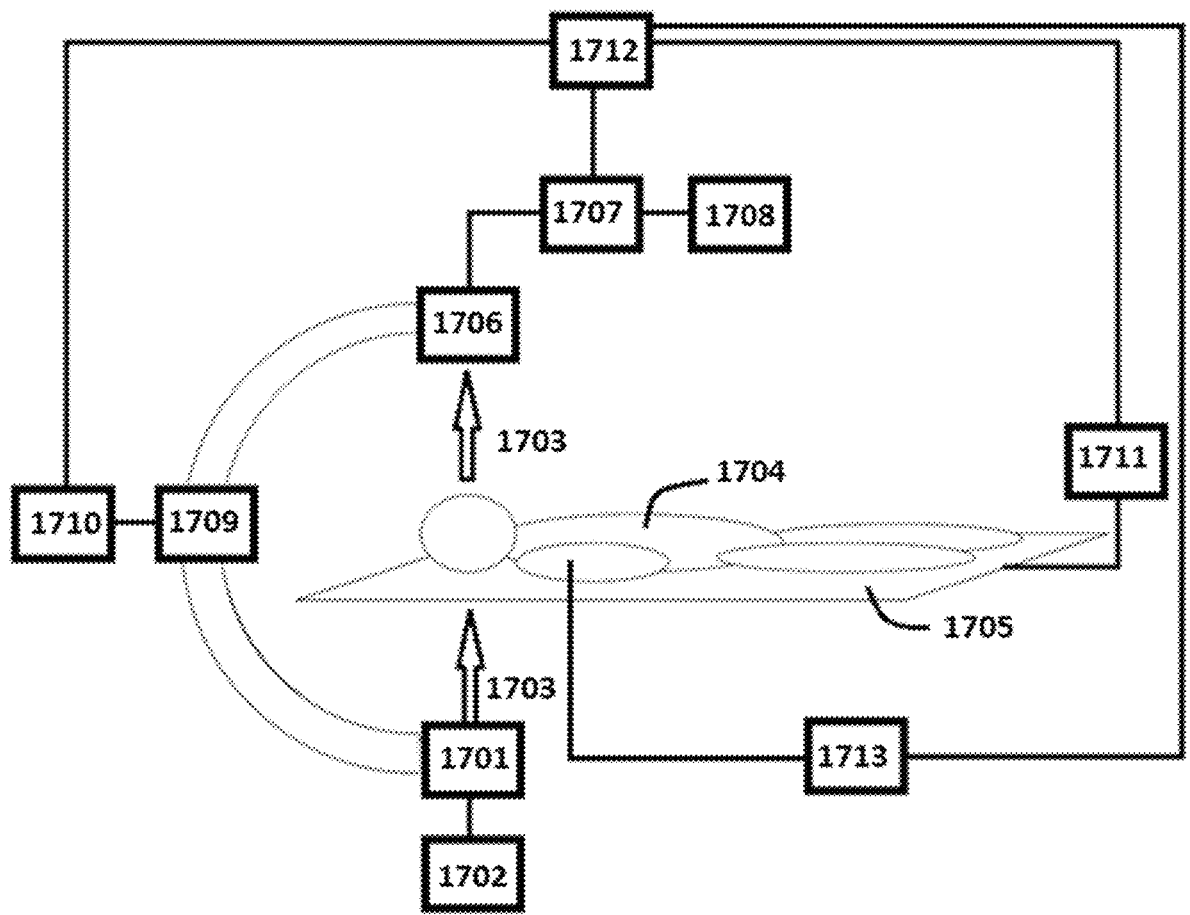
FIG. 17 shows an example of an X-ray cinefluorographic unit block diagram in accordance with embodiments herein.
Figure 33:
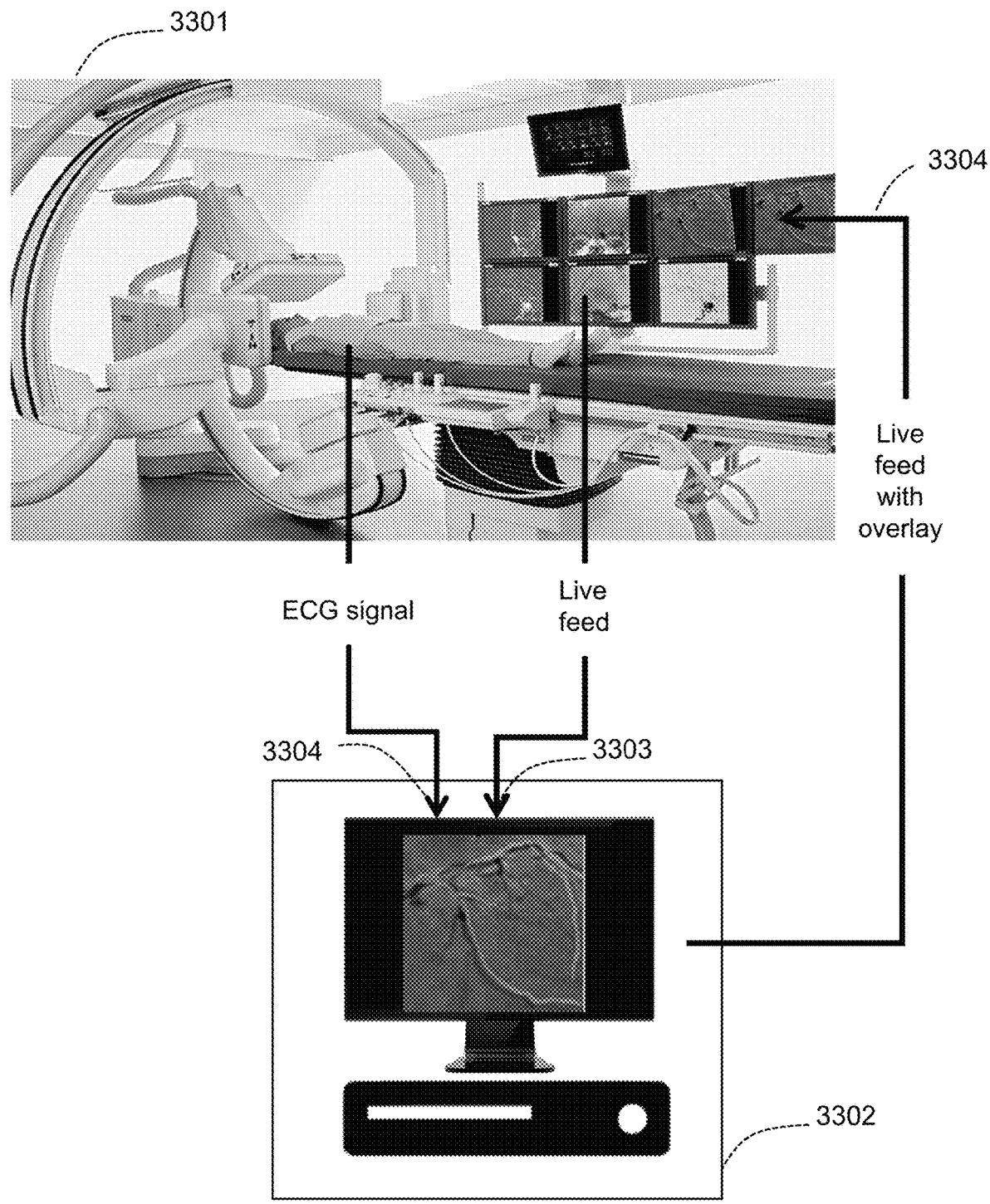
FIG. 33 shows a setup in which the operations are performed in accordance with embodiments herein by a processor unit of a system which is connected to an X-ray system.

Operations can be performed by processor unit on a standalone system, or a semi-standalone system which is connected to the X-ray system (FIG. 2*b*) and described in more detail with reference to FIG. 33, or included directly in, for instance, an x-ray fluorographic system or any other image system to acquire two dimensional angiographic image sequences (FIG. 2*a*). FIG. 17 illustrates an example of a high-level block diagram of an x-ray cinefluorograpic system. In this block diagram an example is shown on how embodiments could integrate in such a system.

Portions of the system (as defined by various functional blocks) may be implemented with dedicated hardware, analog and/or digital circuitry, and/or one or more processors operating program instructions stored in memory.

The X-ray system of FIG. 17 includes an X-ray tubes 1701 with a high voltage generator 1702 that generates an X-ray beam 1703. The high voltage generator 1702 controls and delivers power to the X-ray tube 1701. The high voltage generator 1702 applies a high voltage across the vacuum gap between the cathode and the rotating anode of the X-ray tube 1701. Due to the voltage applied to the X-ray tube 1701, electron transfer occurs from the cathode to the anode of the X-ray tube 1701 resulting in X-ray photon-generating effect also called Bremsstrahlung. The generated photons form an X-ray beam 1703 directed to the image detector 1706.

An X-ray beam 1703 comprises of photons with a spectrum of energies that range up to a maximum determined by among others the voltage and current submitted to the X-ray tube 1701. The X-ray beam 1703 then passes through the patient 1704 that lies on an adjustable table 1705. The X-ray photons of the X-ray beam 1703 penetrate the tissue of the patient to a varying degree. Different structures in the patient 1704 absorb different fractions of the radiation, modulating the beam intensity. The modulated X-ray beam 1703' that exits from the patient 1704 is detected by the image detector 1706 that is located opposite of the X-ray tube. This image detector 1706 can either be an indirect or a direct detection system.

In case of an indirect detection system, the image detector 1706 comprises of a vacuum tube (the X-ray image intensifier) that converts the X-ray exit beam 1703' into an amplified visible light image. This amplified visible light image is then transmitted to a visible light image receptor such as a digital video camera for image display and recording. This results in a digital image signal. In case of a direct detection system, the image detector 1706 comprises of a flat panel detector. The flat panel detector directly converts the X-ray exit beam 1703' into a digital image signal. The digital image signal resulting from the image detector 1706 is passed through a digital image processing unit 1707. The digital image processing unit 1707 converts the digital image signal from 1706 into a corrected X-ray image (for instance inverted and/or contrast enhanced) in a standard image file format for instance DICOM. The corrected X-ray image can then be stored on a hard drive 1708.

Furthermore the X-ray system of FIG. 17 comprises of a C-arm 1709. The C-arm holds the X-ray tube 1701 and the image detector 1706 in such a manner that the patient 1704 and the adjustable table 1705 lie between the X-ray tube 1701 and the image detector 1706. The C-arm can be moved (rotated and angulated) to a desired position to acquire a certain projection in a controlled manner using the C-arm control 1710. The C-arm control allows for manual or automatic input for adjustment of the C-arm in the desired position for the X-ray recording at a certain projection.

The X-ray system of FIG. 17 can either be a single plane or a bi-plane imaging system. In case of a bi-plane imaging system, multiple C-arms 1709 are present each consisting of an X-ray tube 1701, an image detector 1706 and a C-arm control 1710.

Additionally, the adjustable table 1705 can be moved using the table control 1711. The adjustable table 1705 can be moved along the x, y and z axis as well as tilted around a certain point.

Furthermore a measuring unit 1713 is present in the X-ray system. This measuring unit contains information regarding the patient, for instance information regarding ECG, aortic pressure, biomarkers, and/or height, length etc.

A general unit 1712 is also present in the X-ray system. This general unit 1712 can be used to interact with the C-arm control 1710, the table control 1711, the digital image processing unit 1707, and the measuring unit 1713.

An embodiment is implemented by the X-ray system of FIG. 17 as follows. A clinician or other user acquires at least two X-ray angiographic image sequences of a patient 1704 by using the C-arm control 1710 to move the C-arm 1709 to a desired position relative to the patient 1704. The patient 1704 lies on the adjustable table 1705 that has been moved by the user to a certain position using the table control 1711.

The X-ray image sequences are then generated using the high voltage generator 1702, the X-ray tube 1701, the image detector 1706 and the digital image processing unit 1707 as described above. These images are then stored on the hard drive 1708. Using these X-ray image sequences, the general processing unit 1712 performs the methods as described by present application, as for instance as described by FIG. 1, FIG. 15, FIG. 18, FIG. 26 or FIG. 28 using the information of the measuring unit 1713, the digital image processing unit 1707, C-arm control unit 1710 and the table control unit 1711.

As mentioned before the operations can also be performed by a processor unit of a semi-standalone system which is connected to the X-ray system (FIG. 2b). FIG. 33 illustrates such a setup. Within FIG. 33, 3301 represents the X-ray system and 3302 the semi-standalone system in which the operations and described by current application are performed. To obtain the live X-ray image data streams, which can be either an X-ray angiographic image data stream or a X-ray fluoroscopic image data stream, the semi-standalone system 3302 is equipped with a frame grabber (3303) that allows digitalization of live X-ray image data as obtained of the video output from the X-ray system. The live access to the ECG signal is obtained by an analog to digital converted (3304) which is connected to the ECG signal output of the X-ray system or to another system that measures the ECG of the patient. The roadmap overlay that is produced by the methodology presented and described with respected to the flow chart(s) of FIG. 1, FIG. 15, FIG. 18, FIG. 26 or FIG. 28 is supplied to the X-ray system video input (3304) and visualized on the X-ray system monitor.

There have been described and illustrated herein several embodiments of a method and apparatus for quantitative flow analysis. While particular embodiments have been described, it is not intended that the invention be limited thereto, as it is intended that the invention be as broad in scope as the art will allow and that the specification be read likewise. For example, the data processing operations can be performed offline on images stored in digital storage. This is typically done in a universal language (vendor independent) such as DICOM (Digital Imaging and Communications in Medicine). The storage can be a hard disk or a PACS (picture archiving and communications system) server or a VNA (vendor neutral archive) or other picture archiving and communication systems commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

While the disclosed embodiments are described with respect to a single or biplane X-ray imaging modality, variations within these embodiments are also applicable for 3D reconstructions for instance based on rotational angiography, computed tomography, magnetic resonance imaging and the like. The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for generating an image of an object of interest of a patient, the object of interest comprising a heart, a part of the coronary tree, blood vessels or other part of the vasculature of the patient, the method comprising:
   i) obtaining first image data of the object of interest, wherein the first image data is acquired using an X-ray imaging modality with a contrast agent and an interventional device is present in the first image data, the interventional device being used in a procedure to treat the object of interest, wherein the first image data covers at least one cardiac cycle of the patient;
   ii) using the first image data to generate a plurality of roadmaps of the object of interest;
   iii) determining a plurality of reference locations of a tip of the interventional device in the first image data, wherein the plurality of reference locations correspond to the plurality of roadmaps of the object of interest;
   iv) obtaining second image data of the object of interest, wherein the second image data is acquired using an X-ray imaging modality without a contrast agent and the interventional device is present in the second image data;

v) selecting a roadmap from the plurality of roadmaps;

vi) determining a location of the tip of the interventional device in the second image data;

vii) using the reference location of the tip of the interventional device corresponding to the roadmap selected in v) and the location of the tip of the interventional device determined in vi) to transform the roadmap selected in v) to generate a dynamic roadmap of the object of interest; and viii) overlaying a visual representation of the dynamic roadmap of the object of interest as generated in vii) on the second image data for display;

wherein, in vi), the location of the tip of the interventional device in the second image data is determined by inputting the second image data to a trained machine learning network that outputs a posterior probability distribution that estimates likelihood of the location of the tip of the interventional device in the second image data given the second image data as input and using a Bayesian filtering method that equates location of the tip of the interventional device to a weighted arithmetic mean of a plurality of positions and their associated weights derived from the posterior probability distribution output by the trained machine learning network.

2. A method according to claim 1, wherein:
the plurality of roadmaps of the object of interest as generated in ii) covers different phases of the cardiac cycle of the patient.

3. A method according to claim 2, wherein:
the phases of the cardiac cycle of the patient are offset in time relative to a predefined reference part of the cardiac cycle of the patient.

4. A method according to claim 2, further comprising:
acquiring an ECG signal while acquiring the second image data, and processing the ECG signal to determine a phase of the cardiac cycle of the patient that corresponds to the second image data; and
selecting the roadmap in v) by matching the phase of the cardiac cycle of the patient for the second image data to the phase of the cardiac cycle of the patient for the selected roadmap.

5. A method according to claim 4, further comprising:
processing the first image data to determine a phase of the cardiac cycle of the patient for an image frame and associating the phase of the cardiac cycle to a roadmap corresponding to the image frame.

6. A method according to claim 1, wherein:
the plurality of roadmaps of the object of interest comprise a plurality of three-dimensional roadmaps.

7. A method according to claim 6, wherein:
the plurality of three-dimensional roadmaps are derived from a three-dimensional model of the object of interest.

8. A method according to claim 7, wherein:
the three-dimensional model of the object of interest is extracted from at least one image modality selected from the group consisting of computed tomography (CT), X-ray rotational angiography, 3D Ultrasound, or magnetic resonance imaging (MRI).

9. A method according to claim 6, wherein:
the plurality of three-dimensional roadmaps are derived from two X-ray angiographic image sequences of the object of interest acquired with a contrast agent.

10. A method according to claim 6, wherein:
the plurality of three-dimensional roadmaps are derived from a three-dimensional model of the object of interest and at least one X-ray angiographic image sequence of the object of interest acquired with a contrast agent.

11. A method according to claim 10, wherein:
the three-dimensional model of the object of interest is extracted from at least one image modality selected from the group consisting of computed tomography (CT), X-ray rotational angiography, 3D Ultrasound, or magnetic resonance imaging (MRI).

12. A method according to claim 1, wherein:
the plurality of roadmaps include information that characterizes properties of the object of interest.

13. A method according to claim 1, wherein:
the plurality of roadmaps include at least one measurement for the object of interest selected from the group consisting of location and extent of vessel obstruction, diameter and area, pressure, blood velocity, fractional flow reserve, wall shear stress, vessel curvature, amount of foreshortening, location and extent and type of coronary plaque, location and extent of coronary total occlusion, or location and extent of coronary obstruction.

14. A method according to claim 1, wherein:
the Bayesian filtering method involves resampling points around a position with a high weight value.

15. A method according to claim 1, wherein:
the selection of the roadmap in v) is configured to compensate for cardiac motion.

16. A method according to claim 1, wherein:
the operations of vii) apply a transformation to the roadmap selected in v) in order to compensate for motion between the first image data and the second image data.

17. A method according to claim 16, wherein:
the motion includes breathing motion and/or cardiac motion and/or patient motion and/or table motion.

18. A method according to claim 16, wherein:
the transformation comprises a rigid transformation or a non-rigid transformation to the roadmap selected in v) based on a displacement obtained from the reference location of the device corresponding to the roadmap selected in v) and the location of the device determined in vi).

19. A method according to claim 1, wherein:
the visual representation of the dynamic roadmap is generating by
projecting the overlay of the dynamic roadmap onto the second image data using a transparent mode, and/or
dilating the dynamic roadmap and projecting the boundaries of the resultant dynamic roadmap onto the second image data;
whereby the visual representation of the dynamic roadmap is configured to not obscure any instrument used to treat the object of interest.

20. A method according to claim 1, wherein:
the plurality of reference locations is stored as part of the plurality of roadmaps of the object of interest.

21. A method according to claim 1, wherein:
the roadmap selected in v) comprises a three-dimensional roadmap that is transformed to generate at least one dynamic roadmap for overlay on the second image data.

22. A method according to claim 21, wherein:
the three-dimensional roadmap is transformed according to the viewpoint used to acquire the second image data.

23. A method according to claim 21, wherein:
the second image data is acquired from a viewpoint different from the first image data.

24. A method according to claim 1, wherein:
the roadmap selected in v) comprises a two-dimensional roadmap that is transformed to generate at least one dynamic roadmap for overlay on the second image data; and
the first image data and the second image data are acquired from a common viewpoint.

25. A method according to claim 1, wherein:
the first image data is derived by subtraction of a baseline image; and
the second image data is derived by subtraction of the baseline image.

26. A method according to claim 1, wherein:
the operations of iv) to viii) are repeated for successive frames of a live image sequence acquired without a contrast agent.

27. A method according to claim 1, wherein:
the interventional device is selected from the group consisting of a guiding catheter, a guide wire, or other intraluminal device or instrument.

28. A method according to claim 1, further comprising:
displaying the overlay of the visual representation of the dynamic roadmap of the object of interest on the second image data.

29. A method according to claim 1, wherein:
the posterior probability distribution is represented in the image pixel space of the second image data.

30. A method according to claim 1, further comprising:
training the machine learning network using a probability distribution derived from a known location of a tip of an interventional device in a training image dataset.

31. A method according to claim 30, wherein:
the training of the machine learning network uses a catheter segmentation heatmap in combination with the probability distribution derived from a known location of a tip of an interventional device in a training image dataset.

32. A method according to claim 1, wherein:
the Bayesian filtering method further involves determining random samples and associated weights that approximate the posterior probability distribution output by the trained machine learning network by applying a motion model to the random samples, wherein the motion model is estimated from adjacent image frames.

33. A method according to claim 32, wherein:
the motion model is estimated using an optical flow method.

34. A method according to claim 32, wherein:
the Bayesian filtering method further involves resampling the random samples and updating the associated weights in a manner that maximizes the number of effective random samples that have an actual contribution in approximating the posterior probability distribution output by the trained machine learning network.

35. A method according to claim 1, wherein:
the machine learning network comprises a convolutional neural network.

36. A system for generating an image of an object of interest of a patient, the object of interest comprising a heart, a part of the coronary tree, blood vessels or other part of the vasculature of the patient, the system comprising:
at least one processor that, when executing program instructions stored in memory, is configured to i) obtain first image data of the object of interest, wherein the first image data is acquired using an X-ray imaging modality with a contrast agent and an interventional device is present in the first image data, the interventional device being used in a procedure to treat the object of interest, wherein the first image data covers at least one cardiac cycle of the patient;

ii) use the first image data to generate a plurality of roadmaps of the object of interest;

iii) determine a plurality of reference locations of a tip of the interventional device in the first image data, wherein the plurality of reference locations correspond to the plurality of roadmaps of the object of interest;

iv) obtain second image data of the object of interest, wherein the second image data is acquired using an X-ray imaging modality without a contrast agent and the interventional device is present in the second image data;

v) select a roadmap from the plurality of roadmaps;

vi) determine a location of the tip of the interventional device in the second image data;

vii) use the reference location of the tip of the interventional device corresponding to the roadmap selected in v) and the location of the tip of the interventional device determined in vi) to transform the roadmap selected in v) to generate a dynamic roadmap of the object of interest; and viii) overlay a visual representation of the dynamic roadmap of the object of interest as generated in vii) on the second image data for display;

wherein, in vi), the location of the tip of the interventional device in the second image data is determined by inputting the second image data to a trained machine learning network that outputs a posterior probability distribution that estimates likelihood of the location of the tip of the interventional device in the second image data given the second image data as input and using a Bayesian filtering method that equates location of the tip of the interventional device to a weighted arithmetic mean of a plurality of positions and their associated weights derived from the posterior probability distribution output by the trained machine learning network.

37. A system according to claim 36, further comprising:
an imaging acquisition subsystem configured to acquire the first image data and the second image data, wherein the imaging acquisition subsystem uses an X-ray imaging modality.

38. A system according to claim 37, further comprising:
a display subsystem configured to display the overlay of the visual representation of the dynamic roadmap of the object of interest as generated in viii) on the second image data.

39. A non-transitory program storage device tangibly embodying a program of instructions that are executable on a machine to perform operations for generating an image of an object of interest of a patient, the object of interest comprising a heart, a part of the coronary tree, blood vessels or other part of the vasculature of the patient, the operations comprising:

i) obtaining first image data of the object of interest, wherein the first image data is acquired using an X-ray imaging modality with a contrast agent and an interventional device is present in the first image data, the interventional device being used in a procedure to treat the object of interest, wherein the first image data covers at least one cardiac cycle of the patient ii) using the first image data to generate a plurality of roadmaps of the object of interest
iii) determining a plurality of reference locations of a tip of the interventional device in the first image data, wherein the plurality of reference locations correspond to the plurality of roadmaps of the object of interest
iv) obtaining second image data of the object of interest, wherein the second image data is acquired using an X-ray imaging modality without a contrast agent and the interventional device is present in the second image data;
v) selecting a roadmap from the plurality of roadmaps;
vi) determining a location of the tip of the interventional device in the second image data;
vii) using the reference location of the tip of the interventional device corresponding to the roadmap selected in v) and the location of the tip of the interventional device determined in vi) to transform the roadmap selected in v) to generate a dynamic roadmap of the object of interest and
viii) overlaying a visual representation of the dynamic roadmap of the object of interest as generated in vii) on the second image data for display;
wherein, in vi), the location of the tip of the interventional device in the second image data is determined by inputting the second image data to a trained machine learning network that outputs a posterior probability distribution that estimates likelihood of the location of the tip of the interventional device in the second image data given the second image data as input and using a Bayesian filtering method that equates location of the tip of the interventional device to a weighted arithmetic mean of a plurality of positions and their associated weights derived from the posterior probability distribution output by the trained machine learning network.

* * * * *